United States Patent
Rivera

(10) Patent No.: US 11,986,516 B2
(45) Date of Patent: May 21, 2024

(54) COMPOSITIONS AND METHODS FOR TREATMENT OF SARS-COV-2

(71) Applicant: Phenom Pharmaceuticals, LLC, Miami Beach, FL (US)

(72) Inventor: Michelle Lorraine Rivera, Charlotte, NC (US)

(73) Assignee: Phenom Pharmaceuticals, LLC, Miami Beach, FL (US)

( * ) Notice: Subject to any disclaimer, the term of this patent is extended or adjusted under 35 U.S.C. 154(b) by 0 days.

(21) Appl. No.: 18/160,950

(22) Filed: Jan. 27, 2023

(65) Prior Publication Data

US 2023/0302101 A1 Sep. 28, 2023

Related U.S. Application Data

(63) Continuation of application No. PCT/US2022/073456, filed on Jul. 6, 2022.

(60) Provisional application No. 63/234,949, filed on Aug. 19, 2021.

(51) Int. Cl.
| | |
|---|---|
| *A61K 38/48* | (2006.01) |
| *A61K 47/10* | (2017.01) |
| *A61K 47/12* | (2006.01) |
| *A61K 47/26* | (2006.01) |
| *A61K 47/38* | (2006.01) |
| *A61P 31/14* | (2006.01) |

(52) U.S. Cl.
CPC .......... *A61K 38/4813* (2013.01); *A61K 47/10* (2013.01); *A61K 47/12* (2013.01); *A61K 47/26* (2013.01); *A61K 47/38* (2013.01); *A61P 31/14* (2018.01)

(58) Field of Classification Search
CPC ................................................. A61K 38/4886
See application file for complete search history.

(56) References Cited

U.S. PATENT DOCUMENTS

| | | | |
|---|---|---|---|
| 9,320,799 B2 | 4/2016 | Schmitt et al. |
| 9,453,081 B2 | 9/2016 | Sprehe et al. |
| 10,314,893 B2 | 6/2019 | Daniell et al. |
| 2010/0273989 A1 | 10/2010 | Acton et al. |
| 2010/0310546 A1 | 12/2010 | Schuster et al. |

FOREIGN PATENT DOCUMENTS

WO WO 2021191436 9/2021

OTHER PUBLICATIONS apeiron-biologics.com [Online], "Apeiron's APN01 shows clinical benefits for severely ill COVID-19 patients in phase 2 trial," Mar. 12, 2021, [Retrieved on Apr. 17, 2023], retrieved from: URL<https://www.apeiron-biologics.com/wp-content/uploads/20210312_PR_APN01-topline-data_ENG.pdf>, 4 pages.
Ashland.com [Online], "Klucel™ hydroxypropylcellulose—Physical and Chemical Properties," 2017, [Retrieved on Mar. 13, 2023], retrieved from: URL<https://www.ashland.com/file_source/Ashland/Product/Documents/Pharmaceutical/PC_11229_Klucel_HPC.pdf>, 24 pages.

(Continued)

*Primary Examiner* — Rosanne Kosson
(74) *Attorney, Agent, or Firm* — Fish & Richardson P.C.

(57) ABSTRACT

Disclosed herein are formulations comprising recombinant human angiotensin converting enzyme 2 (rhACE-2) and a cellulose derivative for the prevention and treatment of a coronavirus infection. Methods and kits are also provided herein.

14 Claims, 53 Drawing Sheets
Specification includes a Sequence Listing.

(56) References Cited

OTHER PUBLICATIONS

Bourgonje et al., "Angiotensin-converting enzyme 2 (ACE2), SARS-CoV-2 and the pathophysiology of coronavirus disease 2019 (COVID-19)," The Journal of pathology, 2020, 251:228-248.

covid.cdc.gov [Online], "COVID Data Tracker," updates Mon-Fri by 8 pm ET, [Retrieved on Apr. 17, 2023], retrieved from: URL<https://covid.cdc.gov/covid-data-tracker/#datatracker-home>, 5 pages.

Davidson et al., "Interaction of SARS-CoV-2 and Other Coronavirus With ACE (Angiotensin-Converting Enzyme)-2 as Their Main Receptor: : therapeutic implications," Hypertension, 2020, 76(5):1339-1349.

Donoghue et al., "A novel angiotensin-converting enzyme-related carboxypeptidase (ACE2) converts angiotensin I to angiotensin 1-9," Circulation Research, 2000, 87(5):e1-e9.

Haschke et al., "Pharmacokinetics and pharmacodynamics of recombinant human angiotensin-converting enzyme 2 in healthy human subjects," Clinical Pharmacokinetics, 2013, 52:783-792.

Hou et al., "SARS-CoV-2 reverse genetics reveals a variable infection gradient in the respiratory tract," Cell, 2020, 182:429-446.

International Search Report and Written Opinion in International Appln. No. PCT/US2022/073456, dated Oct. 14, 2022, 9 pages.

Kamel et al., "Pharmaceutical significance of cellulose: A review," eXPRESS Polymer Letters, 2008, 2(11):758-778.

Li et al., "Structure of SARS coronavirus spike receptor-binding domain complexed with receptor," Science, 2005, 309:1864-1868.

Lipworth et al., "COVID-19: Start with the nose," the Journal of Allergy and Clinical Immunology, 2020, 146(5):1214.

Marian, "The discovery of the *ACE2* gene," Circulation Research, 2013, 112:1307-1309.

mattek.com [Online], "EpiAirway | Data Sheet," updated on or before Apr. 17, 2023 [Retrieved on Apr. 17, 2023], retrieved from: URL<https://www.mattek.com/wp-content/uploads/EpiAirway_DataSheet.pdf>, 2 pages.

Peacock et al., "SARS-CoV-2 one year on: evidence for ongoing viral adaptation," The Journal of General Virology, 2021, 102:001584.

Sims et al., "Severe acute respiratory syndrome coronavirus infection of human ciliated airway epithelia: role of ciliated cells in viral spread in the conducting airways of the lungs," Journal of Virology, 2005, 79(24):15511-15524.

Tiboni et al., "Nasal vaccination against SARS-CoV-2: Synergistic or alternative to intramuscular vaccines?," International Journal of Pharmaceutics, 2021, 603:120686.

Turner et al., "ACEH/ACE2 is a novel mammalian metallocarboxypeptidase and a homologue of angiotensin-converting enzyme insensitive to ACE inhibitors," Abstract, Canadian Journal of Physiology and Pharmacology, 2002, 80(4):346-353, [Retrieved on Apr. 11, 2023], retrieved from: URL<https://cdnsciencepub.com/doi/10.1139/y02-021>, 2 pages.

Vofo et al., "Nasal lavage containing Angiotensin-Converting Enzyme-2 agonist can prevent and reduce viral load in COVID-19," Medical Hypotheses, 2020, 144:110207.

Zoufaly et al., "Human recombinant soluble ACE2 in severe COVID-19," The Lancet Respiratory Medicine, 2020, 8:1154-1158.

FIG. 51

SARS-1 REM

FIG. 53

COMPOSITIONS AND METHODS FOR TREATMENT OF SARS-COV-2

CROSS-REFERENCE TO RELATED APPLICATIONS

This application is a continuation of International Patent Application No. PCT/US2022/073456, filed Jul. 6, 2022, which claims the benefit of U.S. Provisional Application Ser. No. 63/234,949, filed Aug. 19, 2021, the entire contents of which are incorporated by reference herein.

SEQUENCE LISTING

This application contains a Sequence Listing that has been submitted electronically as an XML file named 51193-0002001_SL_ST26.xml. The XML file, created on Jan. 27, 2023, is 4,307 bytes in size. The material in the XML file is hereby incorporated by reference in its entirety.

TECHNICAL FIELD

This disclosure relates to formulations, methods, and kits used to prevent or treat coronaviruses, including SARS-COV-2. The formulations disclosed herein comprise recombinant human angiotensin converting enzyme 2 (rhACE-2), which prevents or inhibit binding of SARS-CoV-2 to the ACE-2 receptor and thereby prevent and/or treat a coronavirus infection.

BACKGROUND

SARS-CoV-2 has been declared a high-risk global health emergency by the World Health Organization (WHO) and has, as of July 2022, resulted in over 500 million cases of respiratory disease and over 6 million deaths worldwide.

ACE-2 protein is a type I transmembrane glycoprotein with a single zinc metalloprotease active site that acts as a monocarboxypeptidase cleaving a single amino acid, which usually is phenylalanine. Recombinant ACE-2 blocks the binding of the virus based on competitive binding to the viral spike protein.

New strategies for the prophylaxis and/or treatment of SARS-CoV-2 infection, including disruption of the interaction between SARS-CoV-2 and the ACE-2 receptor, are urgently required to effectively mitigate the outbreak.

SUMMARY

Disclosed herein are formulations ideally suited for targeted inhibition of the virus using recombinant protein or peptide technology. Featured are formulations comprising recombinant ACE-2, which blocks the SARS-CoV-2/ACE-2 interaction. The formulations herein are used for the prevention and treatment of COVID-19.

Featured herein are formulations for treatment or prevention of viral infection (e.g., SARS-2 CoV-2 viral infection). In some instances, the formulations comprises (a) a recombinant human angiotensin converting enzyme 2 (rhACE-2) protein that specifically binds to a coronavirus protein, wherein the rhACE-2 protein comprises an amino acid sequence with about 70%, about 75%, about 80%, about 85%, about 90%, about 95%, or about 100% identity to SEQ ID NO:2; (b) a cellulose derivative selected from hydroxypropyl cellulose (HPC), hydroxypropyl methyl cellulose (HPMC), or a combination thereof; and (c) an excipient selected from a glycol alcohol, a sugar alcohol, an acid, an ester, or any combination thereof.

In some instances, the rhACE-2 protein comprises or consists of the amino acid sequence of SEQ ID NO: 2.

In some instances, therhACE-2 protein is at a concentration of about 2 percent weight/weight (w/w). In some instances, therhACE-2 protein is at a concentration of about 0.5 µg/ml to about 50 µg/ml.

In some instances, the cellulose derivative is HPC. In some instances, the HPC is at a concentration lower than about 4 percent w/w. In some instances, the cellulose derivative is HPMC. In some instances, the HPMC is at a concentration from about 1 percent weight/volume (w/v) to about 10 percent w/v. In some instances, the HPMC is at a concentration of about 4 percent w/v.

In some instances, the glycol alcohol is propylene glycol. In some instances, the propylene glycol is at a concentration of less than about 120 mg/ml. In some instances, the propylene glycol is at a concentration of about 1 percent w/w to about 10 percent w/w. In some instances, the propylene glycol is at a concentration of about 5 percent w/w. In some instances, the glycol alcohol is polyethylene glycol (PEG) 400. In some instances, the polyethylene glycol 400 is at a weight of less than about 200 mg. In some instances, the PEG 400 is at a concentration of about 1 percent w/w to about 10 percent w/w. In some instances, the PEG 400 is at a concentration of about 5 percent w/w. In some instances, the sugar alcohol is mannitol. In some instances, the mannitol is at a concentration of about 0.01 percent w/w to about 1 percent w/w. In some instances, the mannitol is at a concentration of about 0.1 percent w/w. In some instances, the sugar alcohol is sorbitol. In some instances, the sorbitol is at a concentration of about 1 percent w/w to about 10 percent w/w. In some instances, the sorbitol is at a concentration of about 5 percent w/w. In some instances, the sugar alcohol is glycerin. In some instances, the glycerin is at a concentration of less than about 25 mg/ml. In some instances, the glycerin is at a concentration of about 1 percent w/w to about 5 percent w/w. In some instances, the glycerin is at a concentration of about 2.5 percent w/w.

In some instances, the acid is sorbic acid. In some instances, the sorbic acid is at a concentration of about 0.01 percent w/w to about 1 percent w/w. In some instances, the sorbic acid is at a concentration of about 0.1 percent w/w.

In some instances, the excipient is polysorbate 20. In some instances, the polysorbate 20 is at a weight of less than about 25 mg. In some instances, the polysorbate 20 is at a concentration of about 0.01 percent w/w to about 1 percent w/w. In some instances, the polysorbate 20 is at a concentration of about 0.1 percent w/w.

Also featured herein are methods of producing any one of the preceding formulations. In some instances, the methods of producing the formulations include (a) providing the rhACE-2 protein; (b) providing one or more of the cellulose derivative and/or the excipient; (c) mixing the rhACE-2 protein, the cellulose derivative, and/or the excipient, thereby producing the formulation.

Also provided herein is a method for preventing a coronavirus infection in a subject in need thereof. In some instances, the method includes administering to a subject a therapeutically effective amount of any of the preceding formulations.

Also provided herein is a method for treating a coronavirus infection in a subject in need thereof. In some instances, the method comprises administering to a subject a therapeutically effective amount of any of the preceding formulations.

Also provided herein is a method of treating a subject with post-acute sequelae of coronavirus infection. In some instances, the method comprises administering to the subject a therapeutically effective amount of any of the preceding formulations.

In some instances, the coronavirus infection is caused by an alphacoronavirus or a betacoronavirus. In some instances, the betacoronavirus is HCoV-NL63, SARS-CoV-1, or SARS-CoV-2. In some instances, the coronavirus infection is caused by a SARS-CoV-2 coronavirus. In some instances, the SARS-CoV-2 coronavirus is selected from hCoV-19/USA-WA1/2020 (WA), hCoV-19/South Africa/KRISP-K005325/2020 (SA), or hCoV-19/England/204820464/2020 (UK), Also disclosed herein are methods of treating a subject with or at risk of being infected with a variant of SARS-CoV-2. In some instances, the method comprises administering to the subject a therapeutically effective amount of any of the preceding formulations. In some instances, the variant of SARS-CoV-2 is selected from hCoV-19/USA-WA1/2020 (WA), hCoV-19/South Africa/KRISP-K005325/2020 (SA), or hCoV-19/England/204820464/2020 (UK).

Also disclosed herein are methods for preventing a viral infection caused by a virus that infects cells by binding to ACE-2 in a subject in need thereof. In some instances, the methods include administering to a subject a therapeutically effective amount of one of the formulations described herein. Also disclosed herein are methods for treating a viral infection caused by a virus that infects cells by binding to ACE-2 in a subject in need thereof. In some instances, the methods include administering to a subject a therapeutically effective amount of one of the formulations described herein. In some instances, the virus is an alphacoronavirus or a betacoronavirus. In some instances, the betacoronavirus is HCoV-NL63, SARS-CoV-1, or SARS-CoV-2. In some instances, the virus is a SARS-CoV-2 coronavirus.

Also disclosed herein are methods of preventing or inhibiting interaction between the receptor binding domain of a virus and ACE-2 in a subject in need thereof. In some instances, the methods include administering to the subject a therapeutically effective amount of one of the formulations described herein. In some instances, the virus is a betacoronavirus. In some instances, the virus is a SARS-CoV-2 coronavirus.

In some instances, the subject is a human subject.

In some instances, the administering is by nasal drop, nasal spray, nebulization, subcutaneous injection, or intravenous injection. In some instances, the administering is by nasal spray or via gel.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Specific terminology is used throughout this disclosure to explain various aspects of the formulations, methods, and kits that are described. This sub-section includes explanations of certain terms that appear in later sections of the disclosure.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The singular form "a", "an", and "the" include plural references unless the context clearly dictates otherwise. For example, the term "a cell" includes one or more cells, including mixtures thereof "A and/or B" is used herein to include all of the following alternatives: "A", "B", "A or B", and "A and B".

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

Figure 51:
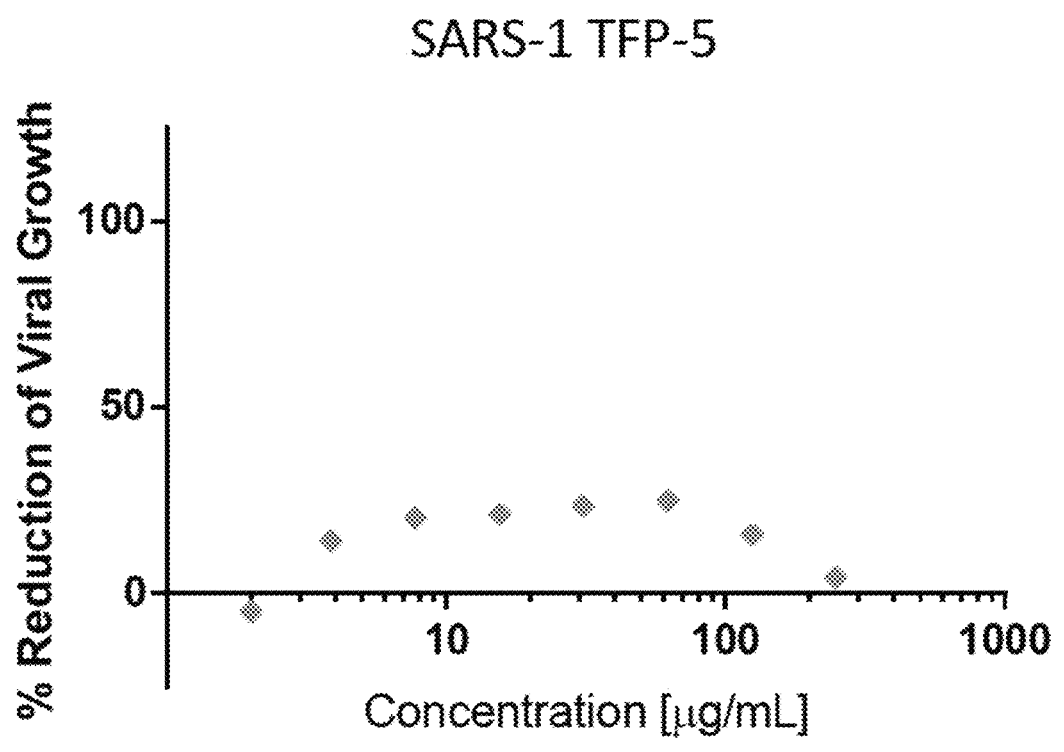
Figure 53:
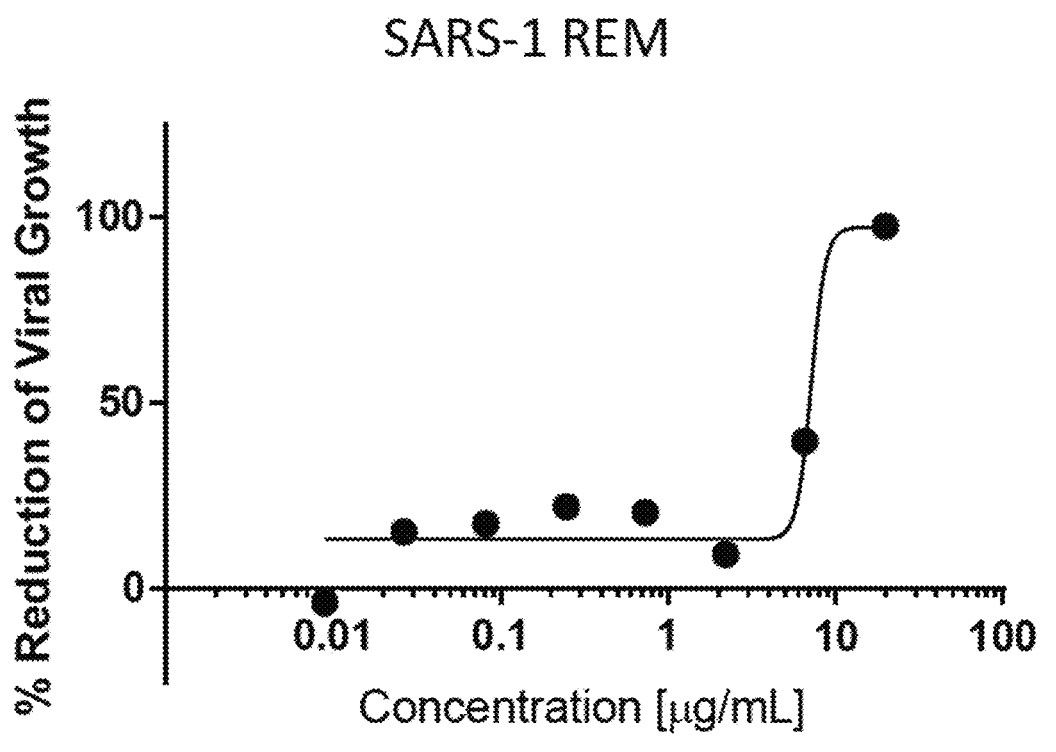

FIGS. 46-53 show percent reduction of viral growth over various concentrations of at increasing concentrations of test articles tested against SARS-CoV-1. SARS-1: SARS-CoV-1.

DETAILED DESCRIPTION

I. Introduction

Figure 1:
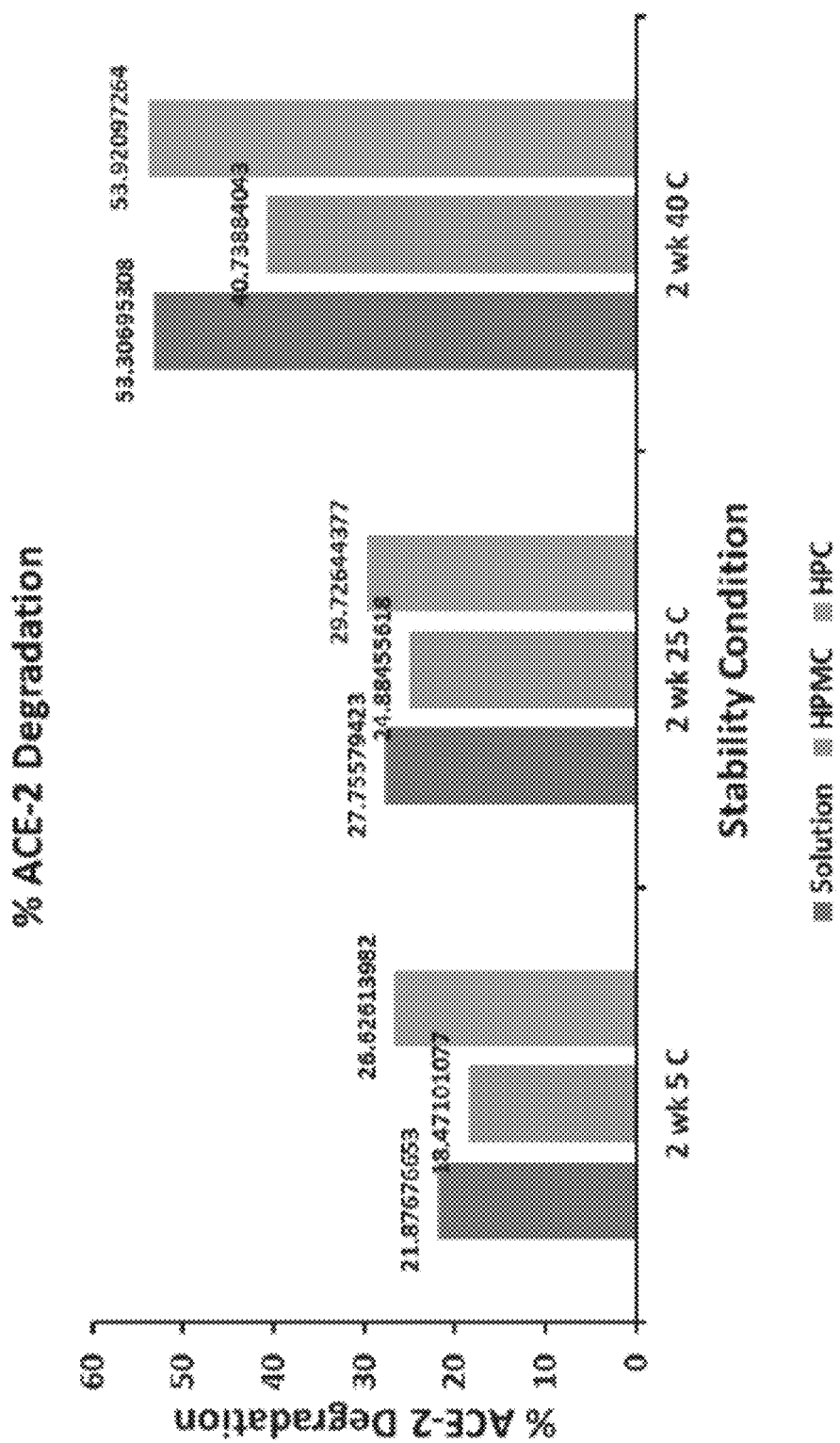
FIG. 1 shows percent rhACE-2 degradation (ng) in HPC, HPMC, and solution-based formulations.
Figure 2:
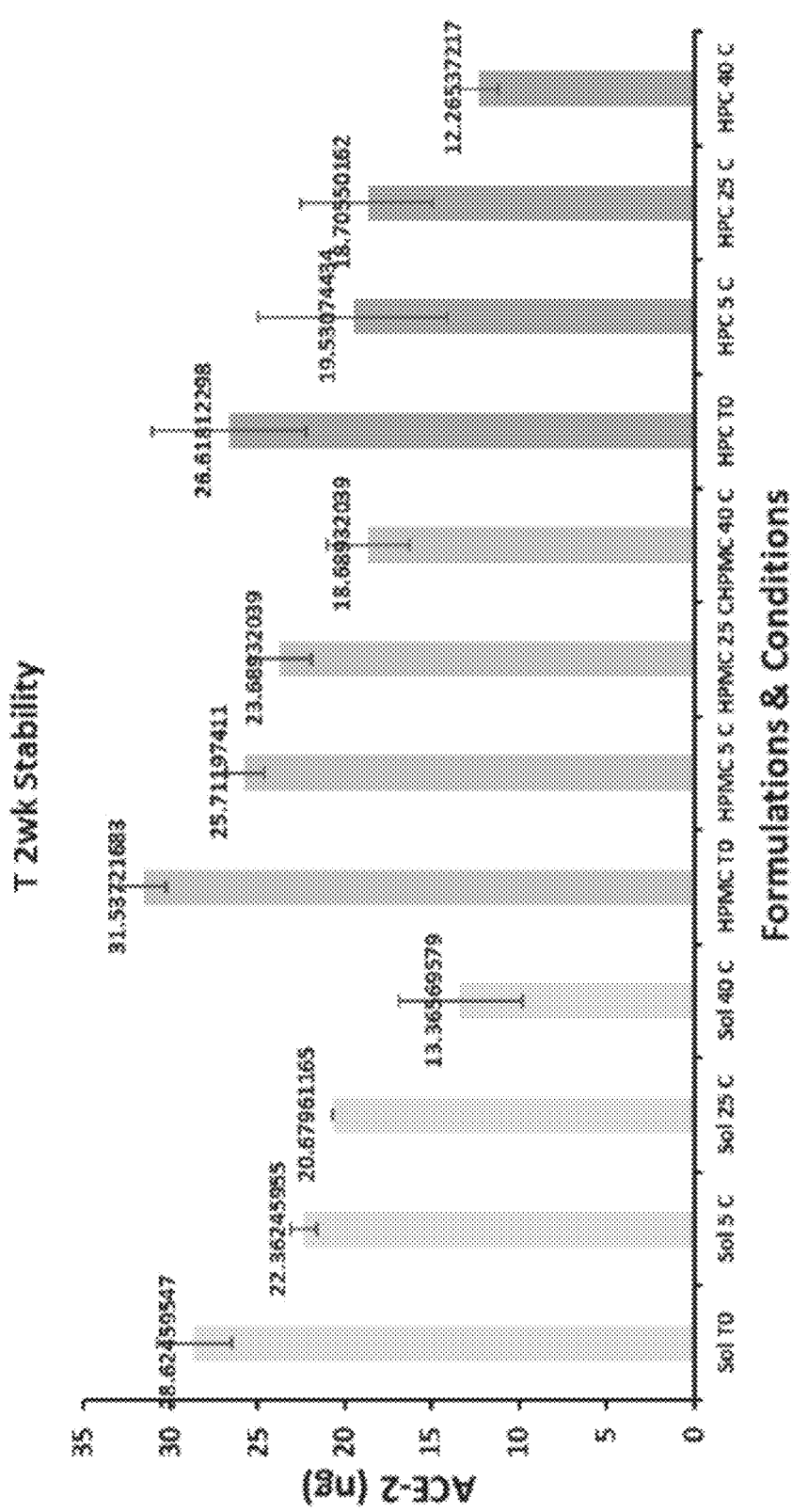
FIG. 2 shows percent rhACE-2 remaining in the formulations at various stability conditions at 2 week time point.
Figure 3:
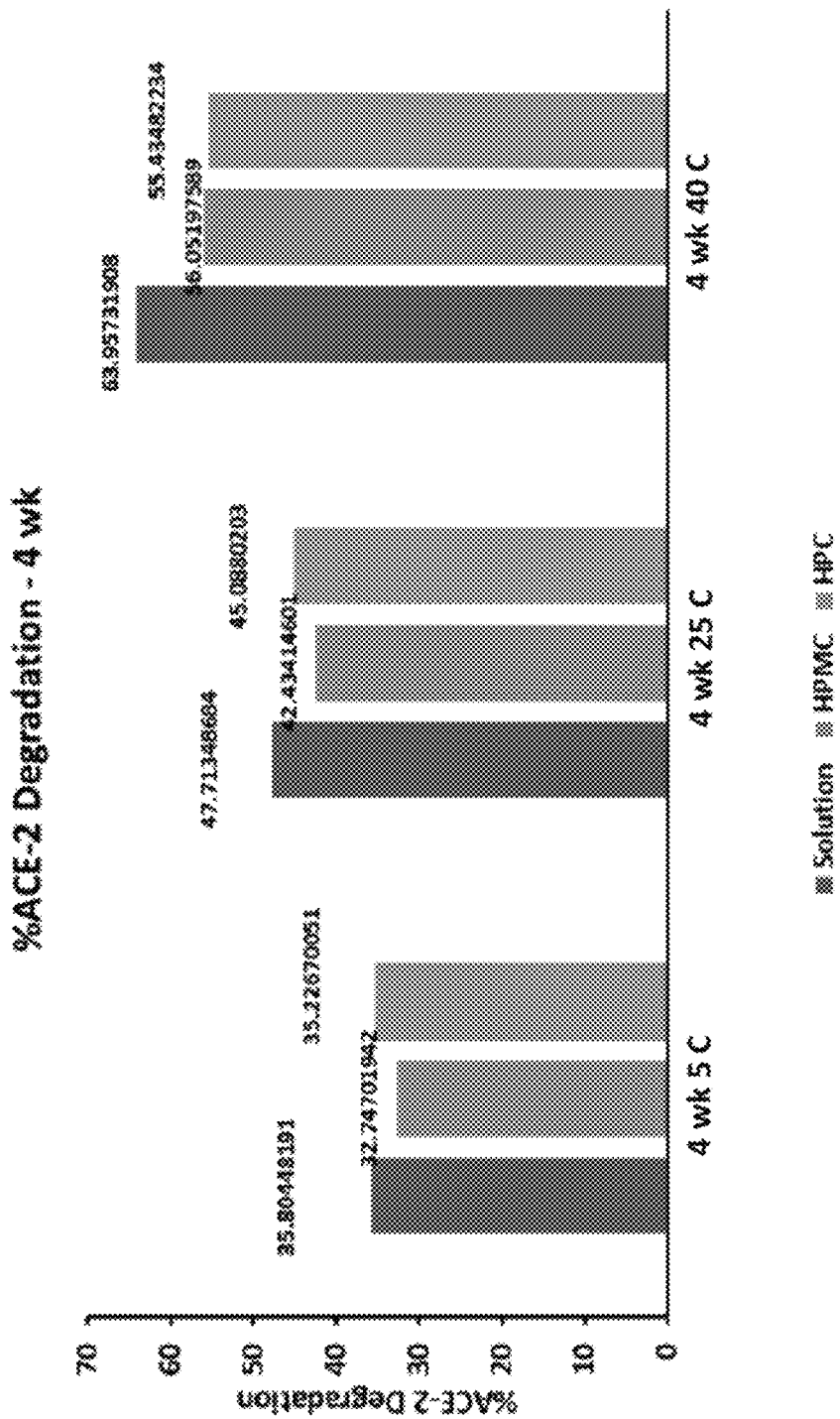
FIG. 3 shows percent rhACE-2 degradation (ng) in HPC, HPMC, and solution-based formulations at two-weeks with respect to $T_0$ at various stability conditions.
Figure 4:
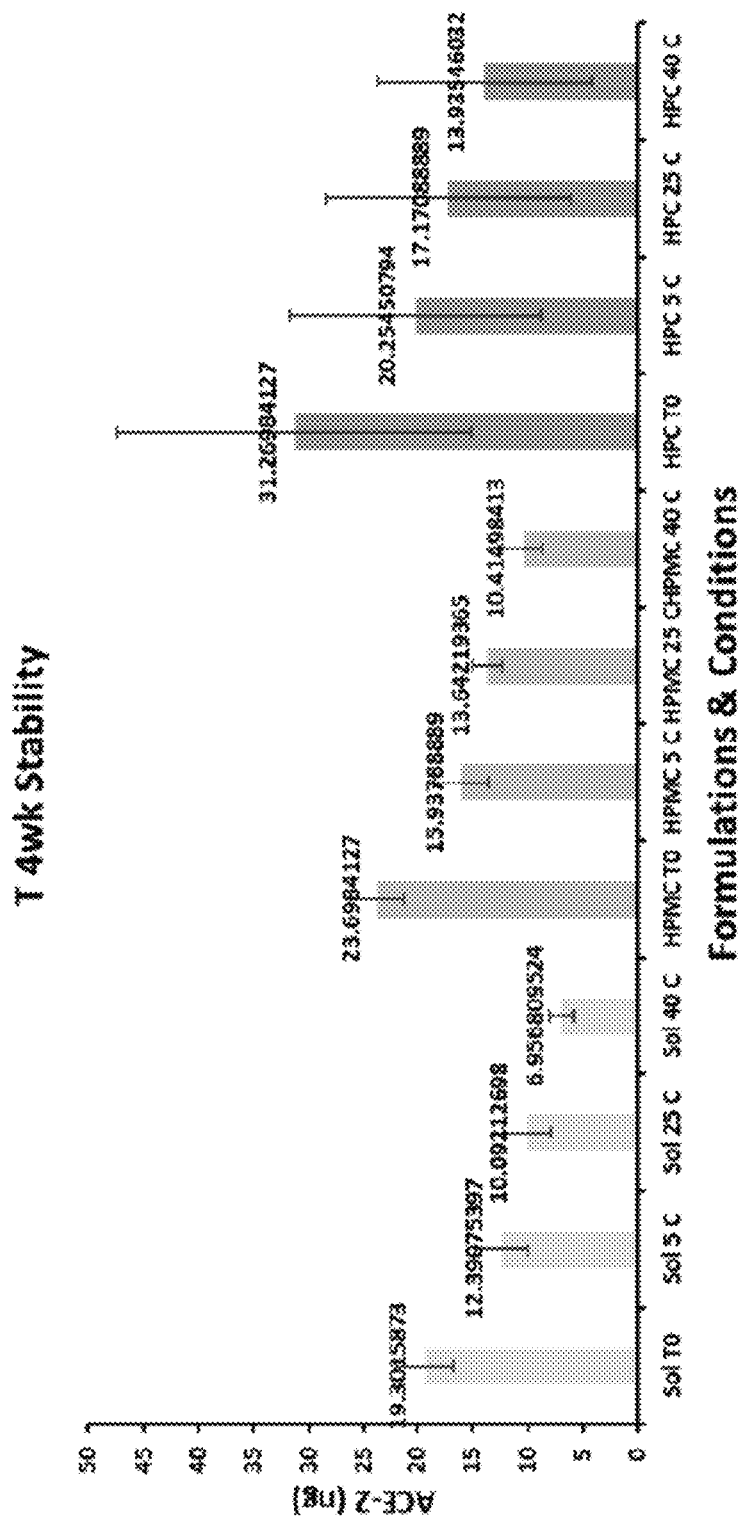
FIG. 4 shows percent rhACE-2 remaining in the formulations at various stability conditions at four-week time point.
Figure 5:
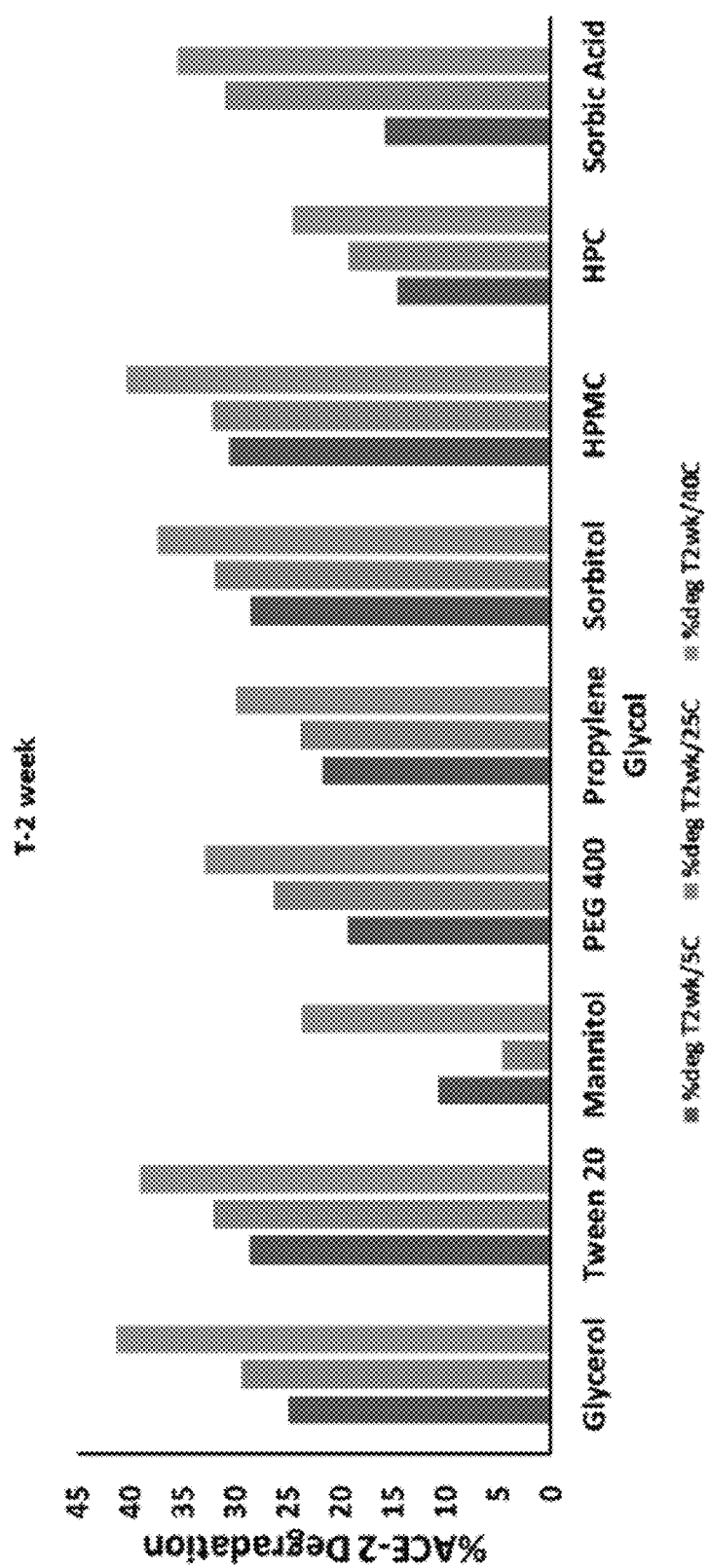
FIG. 5 shows percent rhACE-2 degradation (ng) with the binary mixtures of excipients at 2 weeks with respect to $T_0$ at various stability conditions.
Figure 6:
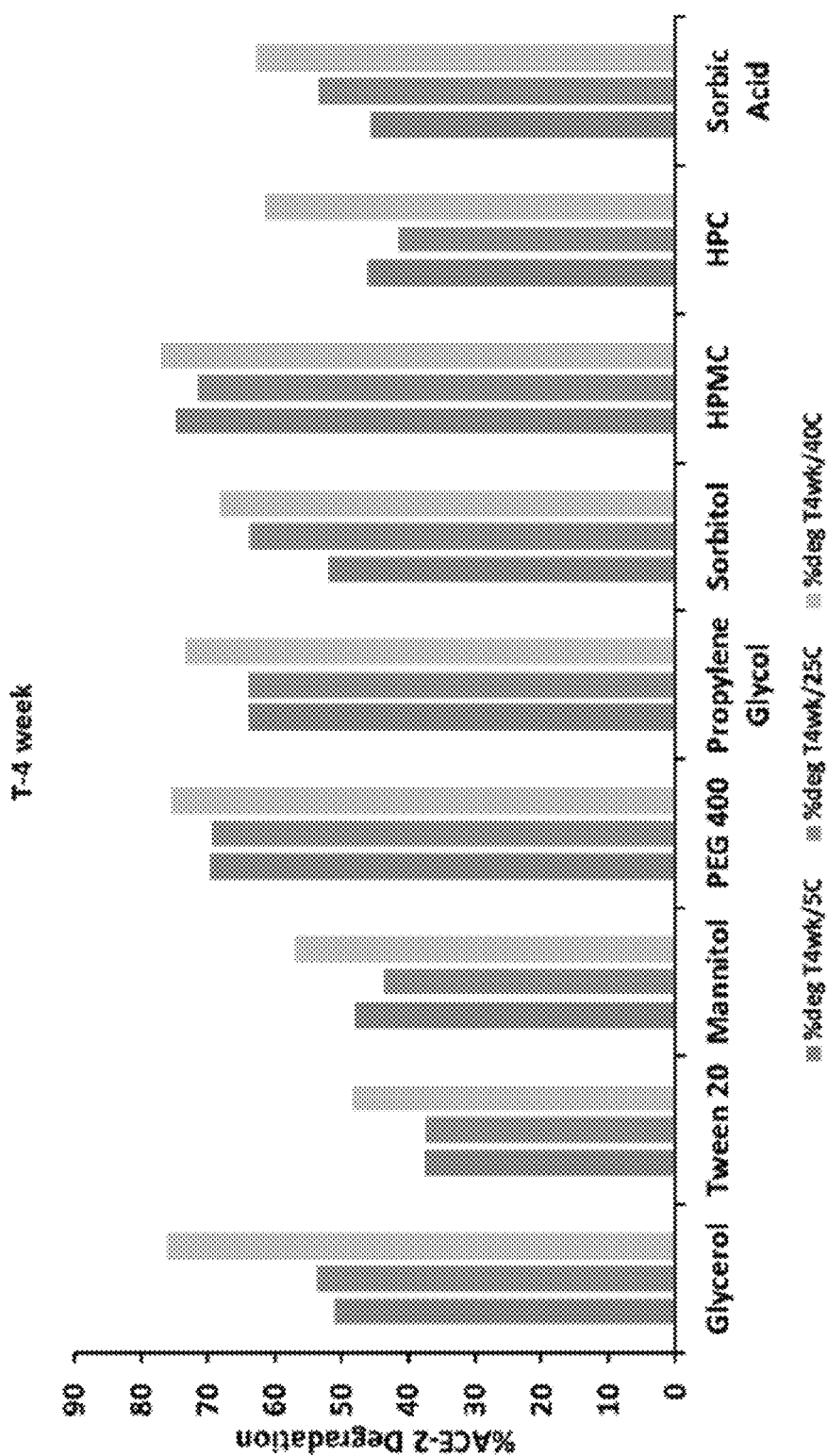
FIG. 6 shows percent rhACE-2 degradation (ng) with the binary mixtures of excipients at 4 weeks with respect to $T_0$ at various stability conditions.
Figure 7:
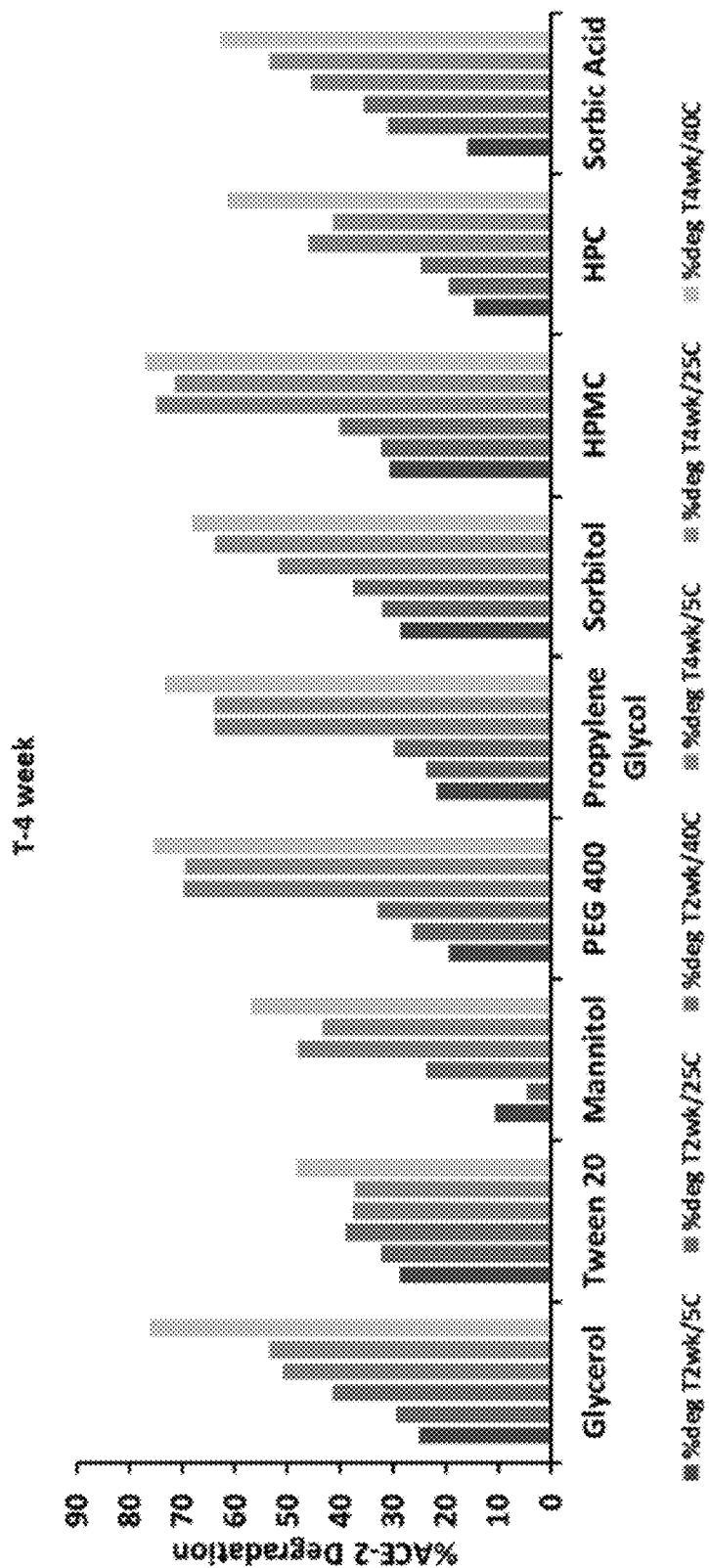
FIG. 7 shows percent rhACE-2 degradation (ng) with the binary mixtures of excipients at 2 weeks and 4 weeks with respect to $T_0$ at various stability conditions.
Figure 8:
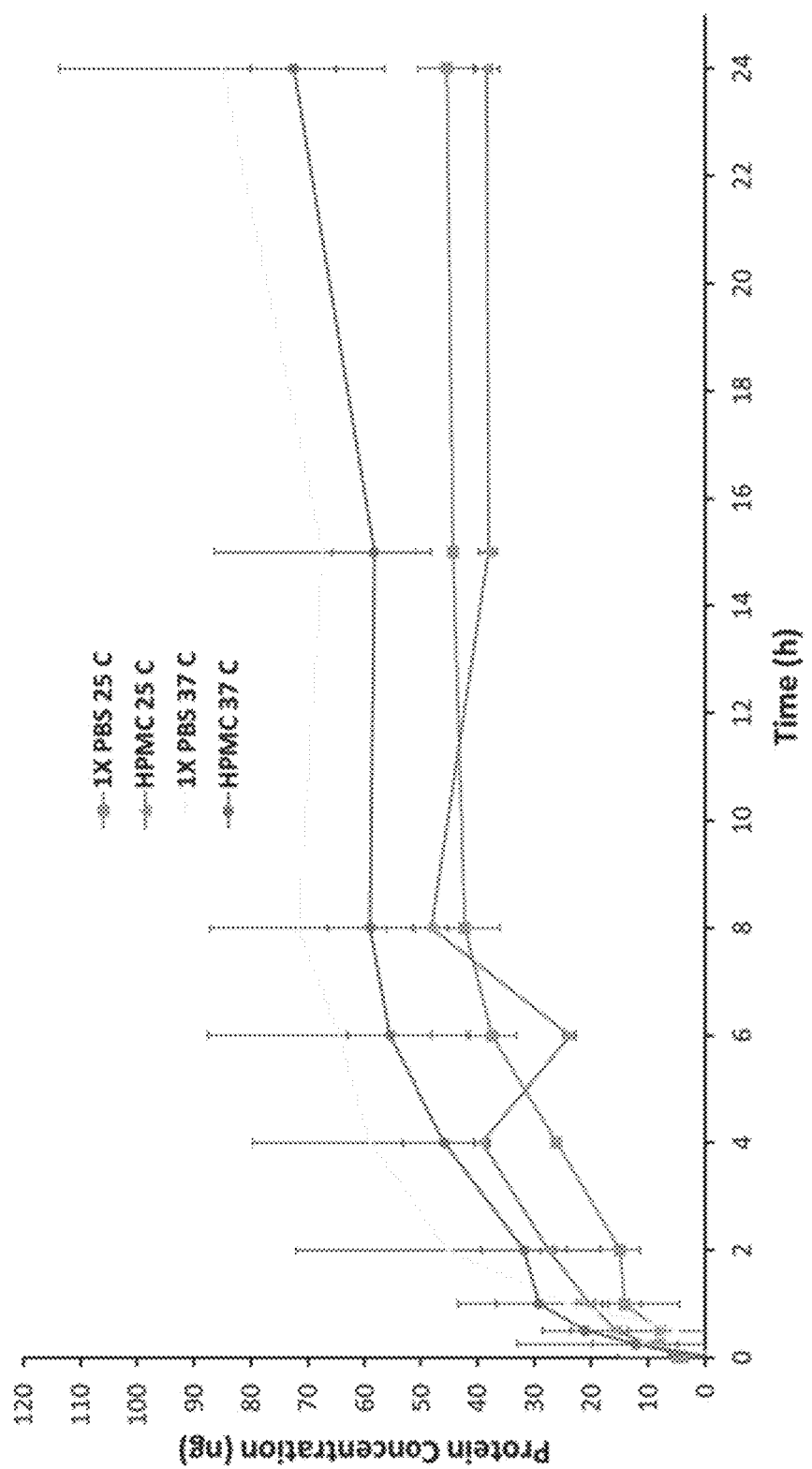
FIG. 8 shows protein concentration bound to spike protein attached to ELISA well plate at various time points.

Coronavirus disease 2019 is an infectious disease that has spread across the world. It is caused by a novel coronavirus, severe acute respiratory syndrome coronavirus 2 (SARS-CoV-2). Angiotensin-converting enzyme 2 (ACE-2) is the cellular receptor for SARS-CoV-2. In particular, this virus binds through its receptor binding domain (SARS-CoV-2 RBD) to an alpha-helical peptide (a1 helix) of the ACE-2 receptor on the surface of a cell (e.g., a respiratory epithelial cell). The spike (S) protein of SARS-CoV-2 plays a key role in the receptor recognition and cell membrane fusion process. Functionally, there is an interaction between ACE-2 a1 helix and the Si protein of the SARS-CoV-2 virus. Si contains the receptor binding domain (RBD), which directly binds to the peptidase domain (PD) of angiotensin-converting enzyme 2 (ACE-2). Li et al., *Science* 309, 1864-1868 (2005), which is incorporated by reference in its entirety.

This disclosure relates, in part, to inhibition of the interaction between the host ACE-2 receptor and SARS-CoV-2. In particular, the present disclosure has identified that the increase of SARS-CoV-2 variants and limited vaccine efficacy and adherence provides a need for formulations that can be used to inhibit and/or treat coronavirus infection. The present disclosure provides formulations that can be used in convenient forms that are easy and safe to use. The present formulations and methods provide localized delivery of the recombinant protein, thus allowing limited to no nasal epithelial penetration, limited to no nasal epithelial irritation, and limited to no skin irritation and penetration.

Accordingly, the present disclosure features formulations that target ACE-2 delivery to nasal epithelium to prevent binding of SARS-CoV-2 to the ACE-2 receptor and thereby prevent or treat infection.

II. Compositions

A. Recombinant Human ACE-2

Sequence analysis suggests that ACE-2 exhibit 42% amino acid homology and ACE-2 has evolved through gene duplication (Donoghue et al., 2000). ACE-2 maps to chromosome Xp22, spans 39.98 kb of genomic DNA, and contains 20 introns and 18 exons (Turner et al., 2002). The ACE-2 gene encodes a type I membrane-bound glycoprotein composed of 805 amino acids (Marian, 2013). The protein sequence of ACE-2 (NP 001358344.1) is provided below as SEQ ID NO: 1.

```
                                              (SEQ ID NO: 1)
MSSSSWLLLSLVAVTAAQSTIEEQAKTFLDKFNHEAEDLFYQSSLASWNY

NTNITEENVQNMNNAGDKWSAFLKEQSTLAQMYPLQEIQNLTVKLQLQAL

QQNGSSVLSEDKSKRLNTILNTMSTIYSTGKVCNPDNPQECLLLEPGLNE

IMANSLDYNERLWAWESWRSEVGKQLRPLYEEYVVLKNEMARANHYEDYG

DYWRGDYEVNGVDGYDYSRGQLIEDVEHTFEEIKPLYEHLHAYVRAKLMN

AYPSYISPIGCLPAHLLGDMWGRFWTNLYSLTVPFGQKPNIDVTDAMVDQ

AWDAQRIFKEAEKFFVSVGLPNMTQGFWENSMLTDPGNVQKAVCHPTAWD

LGKGDFRILMCTKVTMDDFLTAHHEMGHIQYDMAYAAQPFLLRNGANEGF

HEAVGEIMSLSAATPKHLKSIGLLSPDFQEDNETEINFLLKQALTIVGTL

PFTYMLEKWRWMVFKGEIPKDQWMKKWWEMKREIVGVVEPVPHDETYCDP

ASLFHVSNDYSFIRYYTRTLYQFQFQEALCQAAKHEGPLHKCDISNSTEA

GQKLFNMLRLGKSEPWTLALENVVGAKNMNVRPLLNYFEPLFTWLKDQNK

NSFVGWSTDWSPYADQSIKVRISLKSALGDKAYEWNDNEMYLFRSSVAYA

MRQYFLKVKNQMILFGEEDVRVANLKPRISFNFFVTAPKNVSDIIPRTEV

EKAIRMSRSRINDAFRLNDNSLEFLGIQPTLGPPNQPPVSIWLIVFGVVM

GVIVVGIVILIFTGIRDRKKKNKARSGENPYASIDISKGENNPGFQNTDD

VQTSF
```

In some instances, the formulations disclosed herein comprise a recombinant human ACE-2 (rhACE-2) protein. An exemplary rhACE-2 protein sequence is provided below as SEQ ID NO:2.

```
                                              (SEQ ID NO: 2)
QST IEEQAKTFLD KFNHEAEDLF YQSSLASWNY

NTNITEENVQ NMNNAGDKWS AFLKEQSTLA QMYPLQEIQN
```

```
LTVKLQLQAL QQNGSSVLSE DKSKRLNTIL NTMSTIYSTG

KVCNPDNPQE CLLLEPGLNE IMANSLDYNE RLWAWESWRS

EVGKQLRPLY EEYVVLKNEM ARANHYEDYG DYWRGDYEVN

GVDGYDYSRG QLIEDVEHTF EEIKPLYEHL HAYVRAKLMN

AYPSYISPIG CLPAHLLGDM WGRFWTNLYS LTVPFGQKPN

IDVTDAMVDQ AWDAQRIFKE AEKFFVSVGL PNMTQGFWEN

SMLTDPGNVQ KAVCHPTAWD LGKGDFRILM CTKVTMDDFL

TAHHEMGHIQ YDMAYAAQPF LLRNGANEGF HEAVGEIMSL

SAATPKHLKS IGLLSPDFQE DNETEINFLL KQALTIVGTL

PFTYMLEKWR WMVFKGEIPK DQWMKKWWEM KREIVGVVEP

VPHDETYCDP ASLFHVSNDY SFIRYYTRTL YQFQFQEALC

QAAKHEGPLH KCDISNSTEA GQKLFNMLRL GKSEPWTLAL

ENVVGAKNMN VRPLLNYFEP LFTWLKDQNK NSFVGWSTDW

SPYADQSIKV RISLKSALGD KAYEWNDNEM YLFRSSVAYA

MRQYFLKVKN QMILFGEEDV RVANLKPRIS FNFFVTAPKN

VSDIIPRTEV EKAIRMSRSR INDAFRLNDN SLEFLGIQPT

LGPPNQPPVS
```

As used herein, "rhACE-2" in interchangeable with "rACE-2." In some instances, the recombinant ACE-2 protein comprises SEQ ID NO: 2. In some instances, the formulation comprises a an amino acid sequence that is at least 30%, at least 35%, at least 40%, at least 45%, at least 50%, at least 55%, at least 60%, at least 65%, at least 70%, at least 75%, at least 80% or at least 85%, at least 90%, at least 91%, at least 92%, at least 93%, at least 94%, at least 95%, at least 96%, at least 97%, at least 98%, or at least 99% identical to SEQ ID NO: 2. Percent identity as used herein is appreciated to include mutations such as insertions, substitutions, and deletions relative to SEQ ID NO: 2. For instance, a particular amino acid can be substituted, or part (e.g., one or more N-terminus amino acids or one or more C-terminus sequences) of SEQ ID NO: 2 can be deleted. In some instances, the formulation comprises a recombinant ACE-2 protein that includes one or more mutations relative to SEQ ID NO: 2. In some instances, the mutations include at least one (e.g., 1, 2, 3, 4, 5, or 6) amino acid substitution, insertion, or deletion. Substitutions may be conservative and/or non-conservative amino acid substitutions.

In some instances, SEQ ID NO: 2, or a fragment thereof, targets ACE-2 receptor. In some instances, the ACE-2 sequence targets a variant of SARS-CoV-2. Variants are disclosed in Peacock et al., Journal of General Virology, (2021); 102:001584, which is incorporated by reference in its entirety.

B. Recombinant ACE-2 Formulations

Provided herein are formulations comprising rhACE-2 as described herein. The formulations have the desired degree of purity in a physiologically acceptable carrier, excipient or stabilizer (Remington's Pharmaceutical Sciences (1990) Mack Publishing Co., Easton, Pa.). Additional acceptable carriers, excipients, or stabilizers are nontoxic to recipients at the dosages and concentrations employed.

It is appreciated that the concentration of each of the components in the formulation can be modified as necessary. In some instances, a component listed below can be the recommended or maximum dosage or percentage based on a regulatory body's recommended limit for a particular form. For instances, a component listed below can be the recommended or maximum dosage or percentage based on the Food and Drug Administration's inactive ingredient database (IID).

In some instances, the rhACE-2 is in solution form. In some instances, the rhACE-2 is at a concentration of about 0.01% to about 20% (e.g., about 0.1, 0.5, 1, 2, 3, 4, 5, 6, 7, 8, 9, 10, 11, 12, 13, 14, 15, 16, 17, 18, 19, or 20%) of the formulation. In some instances, the rhACE-2 is a lyophilized powder. In some instances, the weight of the rhACE-2 that is added to the formulation ranges from about 0.01 g to about 20 g (e.g., about 0.1, 0.5, 1, 2, 3, 4, 5, 6, 7, 8, 9, 10, 11, 12, 13, 14, 15, 16, 17, 18, 19, or 20 g).

In some instances, the rhACE-2 is in the form of a lyophilized powder. In some embodiments, the lyophilized powder is included in one chamber of a two chamber delivery device. In some instances, the second chamber of the delivery device includes a solution. To dilute and/or solubilize the lyophilized powder, a user breaks the wall between the two chambers, allowing the lyophilized powder to dissolve in the solution.

In some instances, the formulation is placed on a facial covering. For instance, in some embodiments, the formulation (e.g., spray) is placed onto a facial mask. The formulation can be placed (e.g., sprayed) on the inside (e.g., proximal to the person wearing the mask) of the facial covering or on the outside of the facial covering. In some instances, the facial covering includes an insert that comprise one of the formulations disclosed herein. Types of facial coverings include but are not limited to a basic cloth face mask, a surgical face mask, an N95 respirator, a filtering face-piece respirator, a P100 respirator/gas mask, a self-contained breathing apparatus, a full face respirator, a full length face shield, a KN95 respirator, and any combination thereof. In some instances, the formulation is placed on the skin and/or in the eyes (i.e., on the skin; in the eyes; both on the skin and in the eyes).

In some instances, the final concentration of rhACE-2 in the formulation ranges from about 0.1 µg/ml to about 50 µg/ml (e.g., about 0.1, about 0.5, about 1, about 5, about 10, about 15, about 20, about 25, about 30, about 35, about 40, about 45, or about 50 µg/ml). In some instances, the final concentration of rhACE-2 in the formulation is about 1 ug/ml.

In some instances, the formulations include one or more cellulose derivative. In some instances, the one or more cellulose derivative includes hydroxypropyl cellulose (HPC), as shown as an exemplary formula in Formula (I) below.

Formula (I)

$R = H$ or $CH_2CH(OH)CH_3$

HPC comprises hydroxypropoxy group that prevent hydrogen bonding between the hydroxy groups on the cellulose chain, thereby making HPC soluble. HPC is a cellulose ether in which hydroxyl groups on the cellulose backbone have been hydroxypropylated. In some instances, it is manufactured by reacting alkali cellulose with propylene oxide at elevated pressure and temperature to yield a highly substituted cellulose ether, with 3.4-4.1 mol of hydroxypropyl substituent per mole of anhydroglucose backbone units (Ashland, 2001). Because of the high levels of hydroxypropylation (~70%), HPC is more plastic and relatively hydrophobic as compared to other water-soluble cellulose ethers. It is fully soluble in water and polar organic solvents, such as methanol, ethanol, isopropyl alcohol (IPA), and acetone. Solubility of HPC in water is temperature dependent, it is readily soluble at temperatures below the cloud-point (the temperature below which the polymer starts to phase-separate, and two phases appear, thus becoming cloudy), which is around 45° C.

In some instances, the formulations disclosed herein comprise HPC at a concentration lower than or equal to about 4 percent w/w (e.g., about 0.5% w/w, about 1.0% w/w, about 1.5% w/w, about 2.0% w/w, about 2.5% w/w, about 3.0% w/w, about 3.5% w/w, or about 4.0% w/w). In some instances, the HPC is at a concentration of about 0.1 w/w to about 10% w/w.

In some instances, the one or more cellulose derivative includes hydroxypropyl methyl cellulose (HPMC), as shown as an exemplary formula in Formula (II) below.

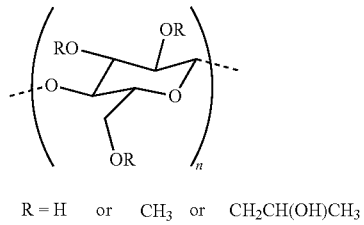

Formula (II)

R = H  or  CH₃  or  CH₂CH(OH)CH₃

HPMC forms flexible and transparent films from aqueous solution. HPMC films are generally odorless and tasteless. HPMC has a variety of properties that allow it to act as a stabilizer, as an emulsifier, as a protective colloid, and as a thickener. HPMC is widely used in oral, ophthalmic and topical controlled release dosage forms because of its non-toxic nature, its capacity to accommodate high level of drug loading and its non-pH dependence.

In some instances, the formulations disclosed herein comprise HPMC at a concentration lower than or equal to about 4 percent w/w (or w/v) (e.g., about 0.5% w/w, about 1.0% w/w, about 1.5% w/w, about 2.0% w/w, about 2.5% w/w, about 3.0% w/w, about 3.5% w/w, or about 4.0% w/w). In some instances, the HPMC is at a concentration of about 0.1 w/w to about 10% w/w.

In some instances, the formulations include one or more buffers. In some instances, the buffers include phosphate, citrate, and other organic acids. In some instances, the buffer is phosphate buffer saline (PBS). In some instances, the buffer is 1×PBS (either final concentration or initial concentration).

In some instances, the formulations include one or more alcohols. In some instances, the alcohols are glycol alcohols. In some instances, the glycol alcohol is propylene glycol. In some instances, the propylene glycol is at a concentration of less than about 120 mg/ml (e.g., about 5, 10, 20, 30, 40, 50, 60, 70, 80, 90, 100, 110, or 120 mg/ml) in a formulation disclosed herein. In some instances, the propylene glycol is at a concentration of about 1 percent w/w to about 10 percent w/w (e.g., about 1, 2, 3, 4, 5, 6, 7, 8, 9 or 10 percent w/w) in a formulation disclosed herein. In some instances, the propylene glycol is at a concentration of about 5 percent w/w.

In some instances, the glycol alcohol is polyethylene glycol. In some instances, the glycol alcohol is polyethylene glycol (PEG) 400. In some instances, the polyethylene glycol 400 is at a weight of less than about 200 mg (e.g., about 5, 10, 20, 30, 40, 50, 60, 70, 80, 90, 100, 110, 120, 130, 140, 150, 160, 170, 180, 190, or 200 mg) in a formulation disclosed herein. In some instances, the PEG 400 is at a concentration of about 1 percent w/w to about 10 percent w/w (e.g., about 1, 2, 3, 4, 5, 6, 7, 8, 9, 10 percent) in a formulation disclosed herein. In some instances, the PEG 400 is at a concentration of about 5 percent w/w.

In some instances, the glycol alcohol is hexylene glycol.

In some instances, the one or more alcohols includes propylene glycol, polyethylene glycol, hexylene glycol, or any combination thereof. In some instances, the one or more alcohols is a sugar alcohol. In some instances, the sugar alcohol is mannitol. In some instances, the mannitol is at a concentration of about 0.01 percent w/w to about 1 percent w/w (e.g., about 0.01, 0.05, 0.1, 0.2, 0.3, 0.4, 0.5, 0.6, 0.7, 0.8, 0.9, or 1.0). In some instances, the mannitol is at a concentration of about 0.1 percent w/w.

In some instances, the sugar alcohol is sorbitol. In some instances, the sorbitol is at a concentration of about 1 percent w/w to about 10 percent w/w (e.g., about 1, 2, 3, 4, 5, 6, 7, 8, 9, or 10 percent w/w). In some instances, the sorbitol is at a concentration of about 5 percent w/w.

In some instances, the sugar alcohol is glycerin. In some instances, the glycerin is at a concentration of less than or equal to about 25 mg/ml (e.g., about 1, 2, 3, 4, 5, 6, 7, 8, 9, 10, 11, 12, 13, 14, 15, 16, 17, 18, 19, 20, 21, 22, 23, 24, or 25 mg/ml). In some instances, the glycerin is at a concentration of about 1 percent w/w to about 5 percent w/w (e.g., about 1, 2, 3, 4, or 5 percent w/w). In some instances, the glycerin is at a concentration of about 2.5 percent w/w.

In some instances, the one or more alcohols includes mannitol, sorbitol, glycerin, or any combination thereof.

In some instances, the formulations include one or more acids and/or esters. In some instances, the acid is sorbic acid. In some instances, the sorbic acid is at a concentration of about 0.01 percent w/w to about 1 percent w/w (e.g., about 0.01, 0.05, 0.1, 0.2, 0.3, 0.4, 0.5, 0.6, 0.7, 0.8, 0.9, or 1.0 percent w/w). In some instances, the sorbic acid is at a concentration of about 0.1 percent w/w.

In some instances, the formulation includes polysorbate 20 (Tween™ 20). In some instances, the polysorbate 20 is at a weight of less than or equal to about 25 mg (e.g., about 1, 2, 3, 4, 5, 6, 7, 8, 9, 10, 11, 12, 13, 14, 15, 16, 17, 18, 19, 20, 21, 22, 23, 24, or 25 mg). In some instances, the polysorbate 20 is at a concentration of about 0.01 percent w/w to about 1 percent w/w (e.g., about 0.01, 0.05, 0.1, 0.2, 0.3, 0.4, 0.5, 0.6, 0.7, 0.8, 0.9, or 1.0 percent w/w). In some instances, the polysorbate 20 is at a concentration of about 0.1 percent w/w.

In some instances, the formulations include one or more addition components selected from antioxidants, preservatives, low molecular weight (less than about 10 residues) polypeptides, proteins, hydrophilic polymers, amino acids, additional sugars, chelating agents, salt-forming counterions, metal complexes, non-ionic surfactants, and any combination thereof.

In some instances, antioxidants include ascorbic acid and methionine. In some instances, preservatives include octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol). In some instances, the one or more low molecular weight (less than about 10 residues) polypeptides. In some instances, proteins include serum albumin, gelatin, or immunoglobulins. In some instances, hydrophilic polymers include polyvinylpyrrolidone. In some instances, amino acids include glycine, glutamine, asparagine, histidine, arginine, or lysine. In some instances, addition sugars include one or more monosaccharides, disaccharides, and other carbohydrates including glucose, mannose, or dextrins, sucrose, trehalose, or sorbitol. In some instances, chelating agents include EDTA. In some instances, salt-forming counter-ions include sodium.

In some instances, the metal complexes include zinc-protein complexes). In some instances, non-ionic surfactants include polyethylene glycol (PEG).

In some instances, the formulations provided herein include one or more pharmaceutically acceptable carriers. In some instances, the pharmaceutically acceptable carriers include aqueous vehicles, nonaqueous vehicles, antimicrobial agents, isotonic agents, buffers, antioxidants, local anesthetics, suspending and dispersing agents, and other pharmaceutically acceptable substances.

Examples of aqueous vehicles include sodium chloride injection, ringers injection, isotonic dextrose injection, sterile water injection, dextrose and lactated ringers injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride.

Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Formulations can include pH adjusters such as sodium hydroxide, hydrochloric acid, citric acid or lactic acid.

A formulation may be prepared for any route of administration to a subject. Specific examples of routes of administration include intranasal, dermal, conjunctival, oral, pulmonary, transdermal, intradermal, and parenteral. In some instances, formulation may be prepared for intranasal administration. In some instances, the formulation is prepared as a spray (e.g., a nasal spray). Formulations can be prepared in conventional forms, either as liquid solutions or suspensions, solid forms suitable such as powder for solution or suspension in liquid prior to injection, as gels, or as emulsions. In some instances, the formulation is a lyophilized powder. In some instances, the formulation is a solution or suspension (e.g., a spray). In some instances, the formulation is a gel.

In some instances, the formulation comprises 0.1% HPMC and lyophilized rhACE-2. In some instances, the formulation comprises HPMC and lyophilized rhACE-2 that are not pre-mixed until right before use (e.g., right before use by a subject in need thereof). In some instances, the rhACE-2 is in the form of a lyophilized powder. In some embodiments, the lyophilized powder is included in one chamber of a two chamber delivery device. In some instances, the second chamber of the delivery device includes a solution comprising 0.1% HPMC. To dilute and/or solubilize the lyophilized powder, a user breaks the wall between the two chambers, allowing the lyophilized powder to dissolve in the solution. A chamber mechanism to house the powder and the solution can be any chamber known in the art.

Also disclosed herein are kits that comprise any one of the formulations. In some instances, the kits include a formulation comprising: (a) an angiotensin converting enzyme 2 (rhACE-2) protein that specifically binds to a coronavirus protein, wherein the rhACE-2 protein comprises an amino acid sequence with about 70%, about 75%, about 80%, about 85%, about 90%, about 95%, or about 100% identity to SEQ ID NO:2; (b) a cellulose derivative selected from hydroxypropyl cellulose (HPC), hydroxypropyl methyl cellulose (HPMC), or a combination thereof; (c) an excipient selected from a glycol alcohol, a sugar alcohol, an acid, an ester, or any combination thereof, and (d) instructions for administering the formulation.

III. Methods of Use

The disclosure features methods of using any of the formulations described herein for the prevention and/or treatment of a coronavirus (e.g., betacoronavirus; e.g., SARS-CoV-2, or a variant thereof) infection or coronavirus disease. The terms "treat" or "treating," as used herein, refers to alleviating, inhibiting, or ameliorating the disease or infection from which the subject (e.g., human) is suffering. In some instances, the subject is an animal. In some embodiments, the subject is a mammal such as a non-primate (e.g., cow, pig, horse, cat, dog, rat, etc.) or a primate (e.g., monkey or human). In some instances, the subject is a domesticated animal (e.g., a dog or cat). In some instances, the subject is a bat. In some instances, the subject is a human. In certain embodiments, such terms refer to a non-human animal (e.g., a non-human animal such as a pig, horse, cow, cat or dog). In some embodiments, such terms refer to a pet or farm animal. In some embodiments, such terms refer to a human.

The formulations described herein can be useful for treating a subject (e.g., human subject) having a coronavirus (e.g., betacoronavirus, e.g., SARS-CoV-2, or a variant thereof) infection. The formulations described herein can also be useful for treating a human subject having a coronavirus disease (e.g., SARS-CoV-2 infection; COVID). In certain embodiments, the coronavirus infection is an infection of one of 229E (alphacoronavirus); NL63 (alphacoronavirus); OC43 (betacoronavirus); HKU1 (betacoronavirus); Middle East respiratory syndrome (MERS); SARS-CoV-1; or SARS-CoV-2. In certain embodiments, the coronavirus disease is caused by a SARS-CoV-2 infection. In certain embodiments, the coronavirus disease is caused by a SARS-CoV-2 variant infection.

The formulations described herein can be useful for preventing (i.e., prophylaxis treatment of) a coronavirus (e.g., betacoronavirus) infection in a subject. The formulation described herein can also be useful for preventing a coronavirus disease in a subject (e.g., human subject). In certain embodiments, the coronavirus infection is an infection of one of 229E (alphacoronavirus); NL63 (alphacoronavirus); OC43 (betacoronavirus); HKU1 (betacoronavirus); Middle East respiratory syndrome (MERS); SARS-CoV-1; or SARS-CoV-2. In certain embodiments, the coronavirus disease is caused by a SARS-CoV-2 infection.

In some instances, the formulations described herein can also be useful for treating a subject with post-acute sequelae of SARS-CoV-2 infection.

In some instances, the formulations described herein can be useful for preventing (i.e., prophylaxis treatment of) a coronavirus (e.g., betacoronavirus) infection in a subject by decreasing intranasal viral load compared to a subject who does not receive the formulation. In some instances, the formulations described herein can be useful for treatment of a coronavirus (e.g., betacoronavirus) infection in a subject by decreasing intranasal viral load compared to a subject who does not receive the formulation.

In some instances, the formulations described herein can be useful for preventing (i.e., prophylaxis treatment of) a coronavirus (e.g., betacoronavirus) infection in a subject by decreasing the risk of contracting the virus compared to a subject who does not receive the formulation.

In addition, the formulations described herein can also be useful for treating or preventing infection by a SARS-CoV-2 variant in a subject. In some instances, the variant is selected from hCoV-19/USA-WA1/2020 (WA), hCoV-19/South Africa/KRISP-K005325/2020 (SA), or hCoV-19/England/204820464/2020 (UK). In some instances, the formulations described herein can also be useful for treating or preventing infection by a SARS-CoV-2 variant such as the Delta variant in a subject.

Also provided are methods of preventing or inhibiting interaction between the receptor binding domain of a virus and ACE-2 in a subject in need thereof using the formulations described herein. In some cases, the virus can be a coronavirus (e.g., SARS-CoV-2).

In certain embodiments, the subject in need thereof is administered a formulation as described herein. In some instances, the formulation is administered intranasally (e.g., via a spray). In some instances, the subject in need thereof administers the formulation. In instances where the formulation is placed onto a facial covering, in some instances, the formulation is sprayed onto the facial covering.

In some instances, a human subject is at risk of being infected with a coronavirus or at risk of developing a coronavirus disease if he or she lives in an area (e.g., city, state, country) subject to an active coronavirus outbreak (e.g., an area where at least 1, at least 2, at least 3, at least 4, at least 5, at least 6, at least 7, at least 8, at least 9, at least 10, at least 20, at least 30, at least 40, or more people have been diagnosed as infected with a coronavirus). In some instances, a human subject is at risk of being infected with a coronavirus or developing a coronavirus disease if he or she lives in an area near (e.g., a bordering city, state, country) a second area (e.g., city, state, country) subject to an active coronavirus outbreak (e.g., an area near (e.g., bordering) a second area where at least 1, at least 2, at least 3, at least 4, at least 5, at least 6, at least 7, at least 8, at least 9, at least 10, at least 20, at least 30, at least 40, or more people have been diagnosed as infected with a coronavirus). In certain embodiments, the coronavirus disease is caused by a SARS-CoV-2 infection.

In some instances, also disclosed are methods of treatment or prevention that include a combination therapy. In some instances, the combination therapy treats or prevents a SARS virus infection (e.g., SARS-CoV-2 or a SARS-CoV-2 variant). In some instances, the combination therapy comprises administration of any one of the formulations disclosed herein. In some instances, the combination therapy further includes one or more of: dexamethasone, remdesivir, baricitinib in combination with remdesivir, favipiravir, merimepodib, an anticoagulation drug selected from low-dose heparin or enoxaparin, bamlanivimab, a combination of bamlanivimab and etesevimab, a combination of casirivimab and imdevimab, convalescent plasma, an mRNA SARS-CoV-2 vaccine (such as those produced by Moderna or Pfizer), an attenuated SARS-CoV-2 virus vaccine, or a dead SARS-CoV-2 virus vaccine. In some instances, the combination therapy comprises a viral vaccine against SARS-CoV-2 (e.g., an adenovirus vaccine such as those produced by Astra Zeneca and Johnson & Johnson. In some instances, the combination therapy comprises a monoclonal antibody that binds the coronavirus (e.g., SARS-CoV-2) and inhibits infection of a human subject. In some instances, the combination therapy comprises orthogonal entry inhibitors, such as antibodies, peptides, and small molecules; and furin inhibitors such as decanoyl-RVKR-chloromethylketone (CMK) and naphthofluorescein.

In general, methods include selecting a subject and administering to the subject an effective amount of one or more of the formulations disclosed herein, e.g., in or as a pharmaceutical composition, and optionally repeating administration as required for the prevention or treatment of a coronavirus infection or a coronavirus disease and can be administered intranasally (e.g. nose spray), as an inhalant (e.g. nebulization to access the respiratory system), orally, intravenously or topically. A subject can be selected for treatment based on, e.g., determining that the subject has a coronavirus (e.g., betacoronavirus) infection.

In some instances, the formulation is an over-the-counter medicine. In some instances, dosage and treatment for use of the formulation can be determined based on anti-viral load.

In some instances, the formulation can be administered (e.g., self-administered) prior to expected exposure of a coronavirus (e.g., SARS-CoV-2). For instance, the formulation can be administered prior to going into a public setting such as an airport, grocery store, etc. In some instances, administration can occur up to at least 1, 2, 3, 4, 5, 6, 7, 8, 9, 10, 11, 12 hours or more before a subject is in the setting of increased exposure risk (e.g., airport, grocery store).

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. For example, effective amounts can be administered at least once.

IV. Methods of Making Formulations

Provided in this application are methods of producing any one of the formulations described herein. Example 1 below provides methods of manufacturing formulations that are HPC-based, HPMC-based, and solution-based.

Additional methods of producing HPC- and HPMC-based solutions have been described previous. See U.S. Pat. No. 9,453,081 B2, U.S. Pat. No. 9,320,799 B2, and Kamel,

V. Examples

Example 1: Manufacture of rhACE-2 Formulations

Manufacture of HPC-Based Formulations

Compositions of hydroxypropyl cellulose (HPC; 0.2%) based prototype are shown in Table 1. The formulation composition is divided into two phases: a buffer phase and a glycol phase. The buffer phase was prepared by adding sorbic acid to accurately weighed 1×PBS and the resulting mixture was heated to 60° C. until the sorbic acid is completely dissolved and a clear solution is obtained. To this solution, mannitol was added and mixed well until the contents are well-dissolved and uniform. Then, the buffer phase was cooled to room temperature (RT) by continuous mixing/stirring on a magnetic stir plate. Once cooled to RT, the buffer phase was supplemented with required quantities of HPC, and the solution was homogenized at 2,500 rpm using an IKA homogenizer until the polymer is well dispersed without fisheyes. In a separate stainless steel vessel, the glycol phase is prepared by adding propylene glycol, PEG 400, glycerin, sorbitol, and polysorbate 20 (Tween® 20). The glycol phase was mixed at 200 rpm for at least 15 min on a magnetic stir plat at RT to ensure complete homogeneity. The formed glycol phase was then added to the buffer phase and mixed well at 200 rpm for at least 15 min to ensure complete homogeneity. If significant foaming was observed, then the formulation was subjected to bath sonication until the foam disappears and a clear solution was observed. Required amounts of rhACE-2 protein was added gently to the mixture using a micropipette and manually mixed gently for at least 10 min to avoid any foaming. Placebo formulation was manufactured in the same way, by replacing rhACE-2 with 1×PBS.

Manufacture of HPMC-Based Formulations

Compositions of hydroxypropyl methyl cellulose-based (HPMC; 0.2% and 1%) prototype are shown in Table 1. The formulation composition was divided into two phases: a buffer phase and a glycol phase. The buffer phase was prepared by adding sorbic acid to accurately weighed 1×PBS and the resulting mixture was heated to 60° C. until the sorbic acid was completely dissolved and a clear solution was obtained. To the above solution, mannitol was added and mixed well until the contents were well dissolved and uniform. Then, the buffer phase was cooled to RT by continuous mixing/stirring on a magnetic stir plate. After cooling, required quantities of HPMC was added and homogenized at 2,500 rpm using an IKA homogenizer until the polymer was well-dispersed without fisheyes. In a separate stainless steel vessel, the glycol phase was prepared by adding propylene glycol, PEG 400, glycerin, sorbitol, and polysorbate 20 (Tween® 20). The glycol phase was mixed at 200 rpm for at least 15 min on a magnetic stir plat at RT to ensure complete homogeneity. The formed glycol phase was then added to the buffer phase and mixed well at 200 rpm for at least 15 min to ensure complete homogeneity. If significant foaming was observed, then the formulation was subjected to bath sonication until the foam disappears and a clear solution was observed. To the above formed mixture, required amounts of rhACE-2 protein was added gently using a micropipette and manually mixed gently for at least 10 min to avoid any foaming. Placebo formulation was manufactured in the same way, by replacing rhACE-2 with 1×PBS.

Manufacture of Solution-Based Formulations

Composition of solution-based prototype is shown in Table 1. The formulation composition was divided into two phases: a buffer phase and a glycol phase. The buffer phase was prepared by adding sorbic acid to accurately-weighed 1×PBS and the resulting mixture was heated to 60° C. until the sorbic acid was completely dissolved and a clear solution was obtained. To the above solution, mannitol was added and mixed well until the contents were well dissolved and uniform. Then the buffer phase was cooled to RT by continuous mixing/stirring on a magnetic stir plate. In a separate stainless steel vessel, the glycol phase was prepared by adding propylene glycol, PEG 400, glycerin, sorbitol, and polysorbate 20 (Tween® 20). The glycol phase was mixed at 200 rpm for at least 15 min on a magnetic stir plat at RT to ensure complete homogeneity. The formed glycol phase was then added to the buffer phase and mixed well at 200 rpm for at least 15 min to ensure complete homogeneity. If significant foaming was observed, then the formulation was subjected to bath sonication until the foam disappears and a clear solution was observed. To the above formed mixture, required amounts of rhACE-2 protein was added gently using a micropipette and manually mixed gently for at least 10 min to avoid any foaming.

Placebo formulation was manufactured in the same way, by replacing rhACE-2 with 1×PBS.

TABLE 1

Composition Grid for HPC (0.2%), HPMC (0.2%, 1%) and Solution Based Formulations

| Ingredient | Manufacturer/Supplier | Compendia | Lot# | Formula (% w/w) - HPC 0.2% Based | Formula (% w/w) - HPMC 0.2% Based | Formula (% w/w) - HPMC 1% Based | Formula (% w/w) - Solution Based |
|---|---|---|---|---|---|---|---|
| ACE-2 Protein | RayBiotech | — | 230-30165 | 2 | 2 | 2 | 2 |
| 1x PBS | Gibco | — | 2063885 | 80.1 | 80.1 | 79.2 | 80.2 |
| Glycerin | J. T. Baker | USP | 0000217402 | 2.5 | 2.5 | 2.5 | 2.5 |
| Polysorbate 20 (Tween 20) | Croda | USP/NF | 0001304514 | 0.1 | 0.1 | 0.1 | 0.1 |
| Mannitol | Penta Mfg. | USP | WXBC5685V | 0.1 | 0.1 | 0.1 | 0.1 |
| PEG 400 | Merck Kga | USP/NF | 00015211145 | 5 | 5 | 5 | 5 |
| Propylene Glycol | Penta Mfg. | NF | 0231-19 | 5 | 5 | 5 | 5 |

TABLE 1-continued

Composition Grid for HPC (0.2%), HPMC (0.2%, 1%) and Solution Based Formulations

| Ingredient | Manufacturer/ Supplier | Compendia | Lot# | Formula (% w/w) - HPC 0.2% Based | Formula (% w/w) - HPMC 0.2% Based | Formula (% w/w) - HPMC 1% Based | Formula (% w/w) - Solution Based |
|---|---|---|---|---|---|---|---|
| Sorbic Acid | Merck Kga | USP/NF | K51212262916 | 0.1 | 0.1 | 0.1 | 0.1 |
| Sorbital | Spectrum | USP | 1JE0354 | 5 | 5 | 5 | 5 |
| HPC | Ashland | USP | 19423 | 0.1 | 0 | 0 | 0 |
| HPMC | Ashland | USP | 0002218909 | 0 | 0.1 | 0.1 | 0 |

Example 2: Assessment of rhACE-2 Formulations 2.1. Assessment Methods

Solubility Assessment

The solubility of compounds in liquid excipients was determined using visual solubility protocol. In this method, about 3.0 g of excipients was accurately weighed in individually labelled 20 mL scintillation vials (USP Type-I). To these vials, accurately measured 1 (1.67 µg) aliquots of protein was added and tightly closed. Post protein addition to the selected solvents, the solution was gently mixed manually for at least 5 min using a plastic spatula at ambient conditions and visually inspected for the solubility of active pharmaceutical ingredients (API). The vials were kept at ambient temperature without agitation for 72 hours and visually inspected at 0, 24, and 72 hours. The results were reported as milligram of drug dissolved in gram of solvent (mg/g).

The excipients used for solubility screening include propylene glycol (up to 120 mg/ml), hexylene glycol, glycerin (up to 25 mg/ml), polyethylene glycol 400 (up to 200 mg), polysorbate 20 (up to 25 mg), purified water, and 1× phosphate buffer saline (PBS).

Methods for Drug Excipient Compatibility (DEC) Studies

ACE-2 protein binary mixture with the excipients listed in Table 2 was prepared such that each sample includes a known amount of API and excipients. For DEC experiments, about 63.0 µL (1 mg in 100 µL protein stock) of rhACE-2 was added to 40 g of 1×PBS as an excipient stock solution, such that the final stock concentration was about 30 μg/mL. From this, approximately 1000 μL of excipient stock was aliquoted into 7 different HDPE 50 mL containers per each excipient and stability condition. The containers were then set on stability at various conditions of 5° C., 25° C./60% RH and 40° C./75% RH for 2 weeks (wk) and 4 wk. Physical observations of each sample were documented at the time of preparation. One vial was available for each time point and environmental storage condition per excipient. The TO time point was stored at −20° C. until completion of testing. One unit was used for all tests (Appearance, & Assay). At 2-week and 4-week time points, samples are pulled and tested for % assay using ELISA. A 1 to 10 dilution of excipient/protein mixture was made, and the sample was then subjected to ELISA analysis. The details of the amount of excipient to the rhACE-2 ratio is provided in Tables 3 and 4.

TABLE 2

| Excipients for DEC Study, their functional category and IID limits | | | | | |
|---|---|---|---|---|---|
| S/No. | Components | % w/w (Anticipated Use Levels) | IID Limits (Topical) | IID Limits (Nasal) | Application |
| 1 | 1X PBS | 82.2 | Not Applicable | Not Applicable | Solvent & buffer |
| 2 | Glycerin | 2.5 | 20 | 2.5 | Humectant & Viscosifying agent |
| 3 | Tween 20 | 0.1 | 15 | 2.7 | Surfactant |
| 4 | Mannitol | 0.1 | 2.39 | 4.15 | Protein stabilizer |
| 5 | PEG 400 | 5 | 99 | 20 | Solvent; viscosity increasing agent |
| 6 | Propylene Glycol | 5 | 99.98 | 12 | Solvent; viscosity increasing agent |
| 7 | Sorbic acid | 0.1 | 0.75 | Not Approved | Solvent; viscosity increasing agent; preservaGve |
| 8 | Sorbitol | 5 | 36.8 | 2.5 | Stabilizing agent |
| 9 | HPC | 0.2 | Not Applicable | Not Applicable | Solvent |
| 10 | HPMC | 0.2 | 4 | Not Approved | Gelling agent |

TABLE 3

| DEC Stability Sample Conditions for Active (i.e., Test) Samples | | | | | | | | |
|---|---|---|---|---|---|---|---|---|
| Components | Stock Amount (mg) | Excipient (mg) | Remaining PBS (mg) | Code (T0) | Code (T2 wk.) 25° C./60% | Code (T4 wk.) 25° C./60% | Code (T2 wk.) 40° C./75% | Code (T4 wk.) 40° C./75% |
| ACTIVES | | | | | | | | |
| 1X PBS + ACE-2 | 900 | — | 100 | A | A1 | A2 | A3 | A4 |
| Glycerin + ACE-2 | 900 | 25 | 75 | B | B1 | B2 | B3 | B4 |
| Tween 20 + ACE-2 | 900 | 1 | 99 | C | C1 | C2 | C3 | C4 |
| Mannitol + ACE-2 | 900 | 5 | 95 | D | D1 | D2 | D3 | D4 |

TABLE 3-continued

DEC Stability Sample Conditions for Active (i.e., Test) Samples

| Components | Stock Amount (mg) | Excipient (mg) | Remaining PBS (mg) | Code (T0) | Code (T2 wk.) 25° C./60% | Code (T4 wk.) 25° C./60% | Code (T2 wk.) 40° C./75% | Code (T4 wk.) 40° C./75% |
|---|---|---|---|---|---|---|---|---|
| PEG 400 + ACE-2 | 900 | 50 | 50 | E | E1 | E2 | E3 | E4 |
| Propylene Glycol + ACE-2 | 900 | 50 | 50 | F | F1 | F2 | F3 | F4 |
| Sorbic Acid + ACE-2 | 900 | 5 | 95 | G | G1 | G2 | G3 | G4 |
| Sorbitol + ACE-2 | 900 | 50 | 50 | H | H1 | H2 | H3 | H4 |
| HPC + ACE-2 | 900 | 3 | 97 | K | K1 | K2 | K3 | K4 |
| HPMC + ACE-2 | 900 | 1 | 99 | M | M1 | M2 | M3 | M4 |

TABLE 4

DEC Stability Sample Conditions for Placebo Samples

| Components | 1X PBS (mg) | Excipient (mg) | Code (T0) | Code (T2 wk.) 25° C./60% | Code (T4 wk.) 25° C./60% | Code (T2 wk.) 40° C./75% | Code (T4 wk.) 40° C./75% |
|---|---|---|---|---|---|---|---|
| PLACEBOS | | | | | | | |
| 1X PBS | 1000 | — | AA | AA1 | AA2 | AA3 | AA4 |
| Glycerin | 975 | 25 | BB | BB1 | BB2 | BB3 | BB4 |
| Tween ® 20 | 999 | 1 | CC | CC1 | CC2 | CC3 | CC4 |
| Mannitol | 995 | 5 | DD | DD1 | DD2 | DD3 | DD4 |
| PEG 400 | 950 | 50 | EE | EE1 | EE2 | EE3 | EE4 |
| Propylene Glycol | 950 | 50 | FF | FF1 | FF2 | FF3 | FF4 |
| Sorbic Acid | | | GG | GG1 | GG2 | GG3 | GG4 |
| Sorbitol | 950 | 50 | HH | HH1 | HH2 | HH3 | HH4 |
| HPC | 997 | 3 | KK | KK1 | KK2 | KK3 | KK4 |
| HPMC | 999 | 1 | MM | MM1 | MM2 | MM3 | MM4 |

ELISA

A RayBio® COVID-19 Spike-ACE-2 binding assay uses a 96-well plate coated with recombinantly-expressed S-RBD. The testing reagent-of-choice (in this case formulations or excipient binary mixtures) with known amount of ACE-2 was then added to the wells. Unbound ACE-2 was removed with washing, and a goat anti-ACE-2 antibody that binds to the Spike-ACE-2 complex was added. HRP-conjugated anti-goat IgG was then applied to the wells in the presence of a 3,3',5,5'-tetramethylbenzidine (TMB) substrate. The HRP-conjugated anti-goat IgG bound to the ACE-2 antibody and reacted with the TMB solution, producing a blue color that was proportional to the amount of bound ACE-2. The HRP-TMB reaction was halted with the addition of the Stop Solution, resulting in a blue-to-yellow color change. The intensity of the yellow color was then measured at 450 nm.

Short-Term Stability Methods

ACE-2 active at a concentration of 250 ng/mL and a 30 g placebo prototypes for HPC-based, HPMC-based, and solution-based formulations were manufactured by Tergus Pharma. Each batch was filled into plastic containers. Any excess bulk material was transferred to amber colored glass jars with HDPE screw tops and frozen at −20° C. Each unit was assigned a specific Tergus Pharma sample number and were placed for stability at 5° C., 25±2° C./60±5% RH, and 40±2° C./75±5% RH for 2 wk. and 4 wk. T0 sample was set at −20° C. until analysis.

Methods to Determine Reaction Rate Kinetics

The prototypes were incubated in each well of the ELISA well plate using standard methods. Active HPMC formulation was tested since it has shown more stability compared to other formulations. HPMC formulation was tested in comparison to 1×PBS, where the concentration of utilized protein was 4-fold less in HPMC based formulation because the product demonstrated 4-fold more activity compared to 1×PBS.

The initial concentrations of proteins added were 18.78 ng per well for 1×PBS and 4.69 ng per well for HPMC formulation. The formulation was incubated for 24 h and analyzed at time points 0 h, 0.25 h, 0.5 h, 1.0 h, 2.0 h, 4.0 h, 6.0 h, 8.0 h, 15.0 h, and 24.0 h. At each time point, formulations or excipient mixtures were removed, and the wells were washed with 1×PBS thrice and then the wells were filled with 1×PBS until further testing using ELISA.

Methods of Container Closure and Sprayability Assessment

Sprayability assessment was performed to understand the impact of the formulation composition on the sprayability and spray pattern of the formulation. Tare weight of the spray bottle was taken. Required amounts of 1% HPMC placebo formulation is filled into spray bottles making sure that the bottles are filled to the top.

For assessing the dispensed formulation, the following protocol was used. The weight of the container was measured. Then the formulation was dispensed into the container, and the gross weight was measured. After each spray, the weight of the container was measured. Then, using the initial container weight, the weight of each spray (n=10 sprays) was measured.

In addition, the spray pattern was assessed. After each spray, images were taken and were uploaded to ImageJ software. A scale was set using a ruler in the image. Patterns were then selected using the free hand selection tool on ImageJ software, and the selected patterns were analyzed.

2.2. Assessment Results

Solubility Assessment Results

Visual solubility studies were performed using various topical excipients that are compliant with global compendia and listed on the Food and Drug Administration's inactive ingredient database (IID). The present study evaluated the solubility of ACE-2 protein in a selection of solvents based on their IID limit for nasal application. The effect of these solvents on the stability of ACE-2 protein was also examined by visual observation. ACE-2 protein solution was readily soluble in all the excipients tested, with very good solubility in propylene glycol, hexylene glycol, glycerin, polyethylene glycol 400, polysorbate 20, purified water and PBS. ACE-2 demonstrated stable solubility in all the solvents tested by maintaining a visually clear solution for the entire 72-hour study. The solubility of ACE-2 protein determined from this study was 0.53 μg/g. Further experiments are needed to assess the saturation solubility of ACE-2 in the select excipients. Visual observations are provided in Table 5.

demonstrated that the percent degradation of ACE-2 protein is higher at 40° C., showing a 40%-54% degradation of ACE-2. However, the degradation of ACE-2 stored at both 5° C. and 25° C. was found to be similar for all three formulations, indicating that each of the formulations can be stored at RT.

The stability of the HPC-based, HPMC-based and solution-based formulations then was assessed after four weeks at 5° C., 25° C., and 40° C. As shown in FIG. 3, there was a 55%-64% percent degradation of ACE-2 protein at four weeks across the formulations. Further, as shown in FIG. 4, the degradation of ACE-2 stored at 5° C. was about 33%-35%, and the degradation of ACE-2 stored at 25° C. was about 42%-47%.

Drug Excipient Compatibility (DEC) Results

Next, ELISA was used to assess the stability of ACE-2 protein and its compatibility with various excipients used in the formulations. Interestingly, ACE-2 activity was almost 4-fold higher in Tween® 20 as a single excipient and other formulations (~300 ng/well) with combination of excipients with Tween® 20 being one among them compared to the ACE-2 protein in 1×PBS (~75 ng/well). These results indicate that the presence of surfactant has resulted in the disaggregation of proteins, which might have originally been in aggregated state in PBS based prototype.

TABLE 5

Visual Observations for solubility in Individual Solvents

| | Round I | | | | Round II | | Round III | |
|---|---|---|---|---|---|---|---|---|
| Excipient | Excipient Qty (g) | API Qty (μg) | Duration | Observation | Duration | Observation | Duration | Observation |
| Propylene Glycol | 3.0 | 1.6 | Initial Observation | Clear solution with no undissolved API particles | 24 hr | Clear solution with no undissolved API particles | 72 hr | Clear solution with no undissolved API particles |
| Hexylene Glycol | 3.0 | 1.6 | Initial Observation | Clear solution with no undissolved API particles | 24 hr | Clear solution with no undissolved API particles | 72 hr | Clear solution with no undissolved API particles |
| Glycerin | 3.0 | 1.6 | Initial Observation | Clear solution with no undissolved API particles | 24 hr | Clear solution with no undissolved API particles | 72 hr | Clear solution with no undissolved API particles |
| Polyethylene Glycol 400 | 3.0 | 1.6 | Initial Observation | Clear solution with no undissolved API particles | 24 hr | Clear solution with no undissolved API particles | 72 hr | Clear solution with no undissolved API particles |
| Polysorbate 20 | 3.0 | 1.6 | Initial Observation | Clear yellow solution with no undissolved API particles | 24 hr | Clear yellow solution with no undissolved API particles | 72 hr | Clear yellow solution with no undissolved API particles |
| Purified Water, USP | 3.0 | 1.6 | Initial Observation | Clear solution with no undissolved API particles | 24 hr | Clear solution with no undissolved API particles | 72 hr | Clear solution with no undissolved API particles |
| 1X PBS | 3.0 | 1.6 | Initial Observation | Clear solution with no undissolved API particles | 24 hr | Clear solution with no undissolved API particles | 72 hr | Clear solution with no undissolved API particles |

Short Term Stability Results

Next, stability of the HPC-based, HPMC-based and solution-based formulations was assessed after two weeks at 5° C., 25° C., and 40° C. As shown in FIG. 1, each formulation demonstrated a decreasing trend at two weeks with increased temperature. Compared to 5° C. and 25° C., 40° C. is the worst-case condition at which protein starts degrading substantially. HPMC was the best performing formulation at 2-week time point. In particular, as shown in FIG. 2, TO ELISA results in comparison with two-week results of formulations stored at various stability conditions have Two-week and four-week stability data are shown in Tables 6 and 7 and in FIGS. 1-7. The two-week stability data has shown that the degradation of protein ranged from 10-25% at 5° C. to 5-32% at 25° C./60% RH to 23-41% at 40° C./75% RH. The data indicates that the percent degradation increased with the storage temperature. The four-week stability data has shown that the degradation of protein ranged from 37-65% at 5° C. to 37-71% at 25° C./60% RH to 48-77% at 40° C./75% RH.

The data indicate that the percent degradation increased with the storage temperature; however, as shown in Tables 6 and 7 and in FIGS. 1-7, Tween® 20, HPC, and mannitol protects ACE-2 from degradation compared to other excipients.

TABLE 6

Percent degradation of ACE-2 in ng with the binary mixtures of excipients at various conditions at two weeks.

| Excipient | % Deg T2 wk/5 C. | % Deg T2 wk/25 C. | % Deg T2 wk/40 C. |
|---|---|---|---|
| Glycerol | 25.01381979 | 29.43615257 | 41.32117192 |
| Tween ® 20 | 28.69568255 | 32.18876624 | 39.10507196 |
| Mannitol | 10.70971867 | 4.635549872 | 9.271099744 |
| PEG 400 | 19.41457587 | 26.43369176 | 33.00477897 |
| Propylene Glycol | 21.7327888 | 23.7747958 | 29.9008168 |
| Sorbitol | 28.5935085 | 32.07109737 | 37.48068006 |
| HPMC | 30.66700741 | 32.20035778 | 40.25044723 |
| HPC | 14.62046866 | 19.32705788 | 24.63448828 |
| Sorbic Acid | 15.86408641 | 30.94059406 | 35.49729973 |

TABLE 7

Percent degradation of ACE-2 in ng with the binary mixtures of excipients at various conditions at four weeks.

| Excipient | % Deg T4 wk/5 C. | % Deg T4 wk/25 C. | % Deg T4 wk/40 C. |
|---|---|---|---|
| Glycerol | 51.00334 | 53.51170569 | 76.0869565 |
| Tween ® 20 | 37.48294 | 37.29044903 | 48.4023379 |
| Mannitol | 48.07113 | 43.55033153 | 56.9620253 |
| PEG 400 | 69.65944 | 69.51871658 | 75.4292147 |
| Propylene Glycol | 63.88171 | 64.02526558 | 73.356302 |
| Sorbitol | 51.74901 | 63.82978723 | 68.1572304 |
| HPMC | 74.81613 | 71.51914786 | 77.0986558 |
| HPC | 46.19407 | 41.35192717 | 61.3984118 |
| Sorbic Acid | 45.51889 | 53.46836546 | 62.8879451 |

Reaction Rate Kinetics Results

The purpose of this study was to evaluate the reaction rate kinetics of ACE-2 binding with spike protein. The initial concentrations of proteins added were 18.78 ng per well for 1×PBS and 4.69 ng per well for HPMC formulation. As shown in Table 8, the ACE-2 protein binding increases with time and temperature. Further, as shown in FIG. 8, ACE-2 and Spike protein binding saturation was found to be at 6 to 8 h for both formulations. Activity of 4.69 ng protein in HPMC formulation is equivalent to the activity of 18.78 ng protein in 1×PBS, that is ~4-fold higher activity of protein in HPMC formulation compared to protein in just 1×PBS.

TABLE 8

ELISA Results of ACE-2 in ng of Both 1X PBS and HPMC at Various Conditions

| | 25° C. | | | | 37° C. | | | |
|---|---|---|---|---|---|---|---|---|
| Time (h) | Average (ng) - 1X PBS | Stdev | Average (ng) - HPMC | Stdev | Average (ng) - 1X PBS | Stdev | Average (ng) - HPMC | Stdev |
| 0 | 4.700647 | 0.080093 | 4.021036 | 2.048092 | −8.04207 | 23.20409 | −1.22168 | 10.67525 |
| 0.25 | 8.131068 | 3.398232 | 10.1699 | 1.498883 | 12.00647 | 21.12167 | 12.30583 | 7.70037 |
| 0.5 | 7.742718 | 0.148744 | 15.76861 | 0.560651 | 4.724919 | 18.92483 | 21.05987 | 12.11693 |
| 1 | 14.23139 | 2.871906 | 20.31553 | 2.208278 | 23.99676 | 19.45116 | 29.19903 | 22.75785 |
| 2 | 14.94337 | 3.398232 | 27.59709 | 1.384465 | 45.19417 | 26.86548 | 31.83657 | 5.846789 |
| 4 | 26.14078 | 0.881023 | 39.19903 | 1.338697 | 59.17476 | 20.59534 | 45.88188 | 5.617952 |
| 6 | 37.51618 | 4.336464 | 23.77832 | 1.10986 | 64.49838 | 23.13544 | 55.54207 | 14.97739 |
| 8 | 42.25728 | 6.235812 | 48.19579 | 2.940557 | 71.69903 | 15.56093 | 59.08576 | 4.519534 |
| 15 | 44.23139 | 0.3089 | 38.09871 | 1.590418 | 67.36246 | 19.13079 | 58.32524 | 16.16734 |
| 24 | 45.41262 | 5.068743 | 38.40615 | 2.345581 | 85.04854 | 28.58176 | 72.54854 | 15.48083 |

Container Closure and Sprayability Assessment Results

Figure 9A:
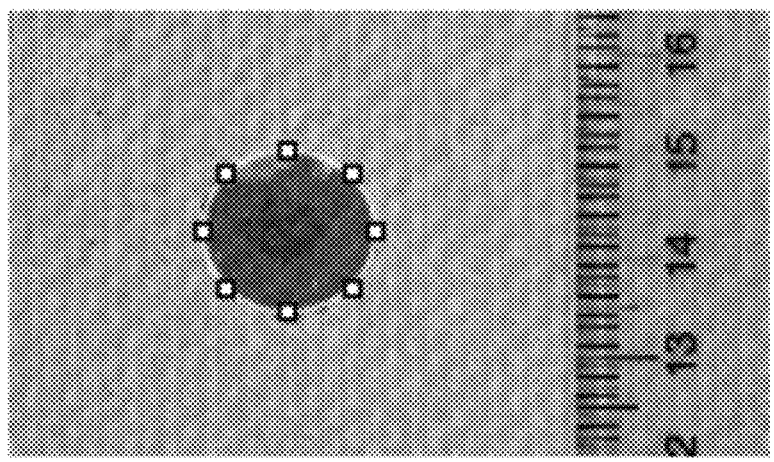
FIG. 9A shows image of the spray pattern being assessed using ImageJ software.
Figure 9B:
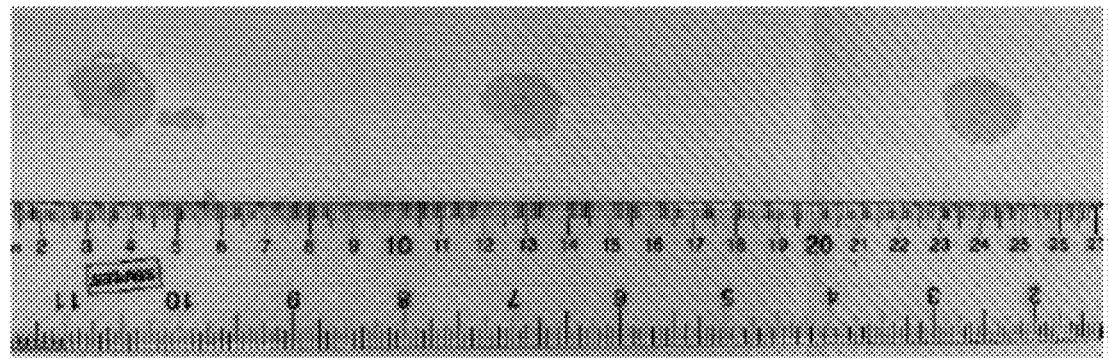
FIG. 9B shows images of three spray patterns taken to determine spray uniformity.

Spray pattern was assessed as described above. FIGS. 9A and 9B show representative images of spray patterns. Table 9 provides measurements of the plume areas of these spray patterns and Table 10 provides the measured amount of formulation that was dispensed in 10 sprays. Plume area was found to be approximately 2.275±0.255 $cm^2$ using the spray bottle 1 and approximately 2.19±0.28 $cm^2$ using the spray bottle 2. This consistent data indicates that the plume area is uniform with a relatively lower standard deviation, which indicates that the formulation spray is consistent.

TABLE 9

Plume areas of the formulation obtained using ImageJ software.

| Test # | Spray Bottle 1 Area (cm2) | Spray Bottle 2 Area (cm2) |
|---|---|---|
| 1 | 2.178 | 2.505 |
| 2 | 2.083 | 1.97 |
| 3 | 2.564 | 2.097 |
| Average | 2.275 | 2.1907 |
| St Dev | 0.255 | 0.2795 |

TABLE 10

Dispensed Amounts of Formulation Measured over 10 Sprays.

| Gross Spray Weights (g) | | Dispensed Spray Weights (g) | |
|---|---|---|---|
| Spray Bottle 1 | Spray Bottle 2 | Spray Bottle 1 | Spray Bottle 2 |
| 46.06 | 50.17 | 0.19 | 0.16 |
| 45.87 | 50.01 | 0.15 | 0.16 |
| 45.72 | 49.85 | 0.18 | 0.18 |
| 45.54 | 49.67 | 0.19 | 0.19 |
| 45.35 | 49.48 | 0.18 | 0.19 |
| 45.17 | 49.29 | 0.18 | 0.2 |
| 44.99 | 49.09 | 0.19 | 0.18 |
| 44.8 | 48.91 | 0.18 | 0.2 |
| 44.62 | 48.71 | 0.2 | 0.19 |
| 44.42 | 48.52 | | |
| | Average | 0.182 | 0.183 |
| | St Dev | 0.0139 | 0.015 |

Figure 10:
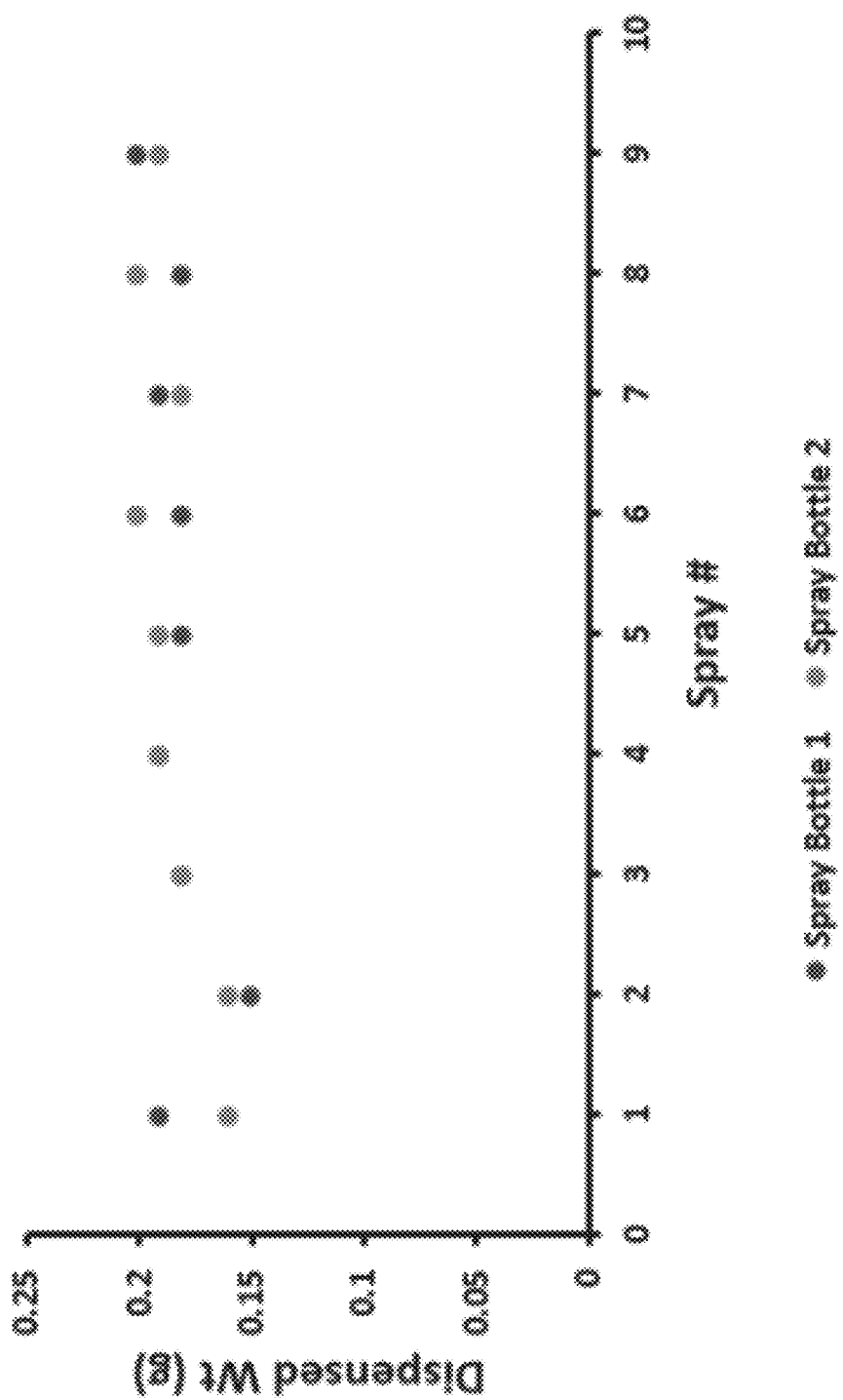
FIG. 10 shows weight of formulation dispensed with respect to the number of sprays.
Figure 11:
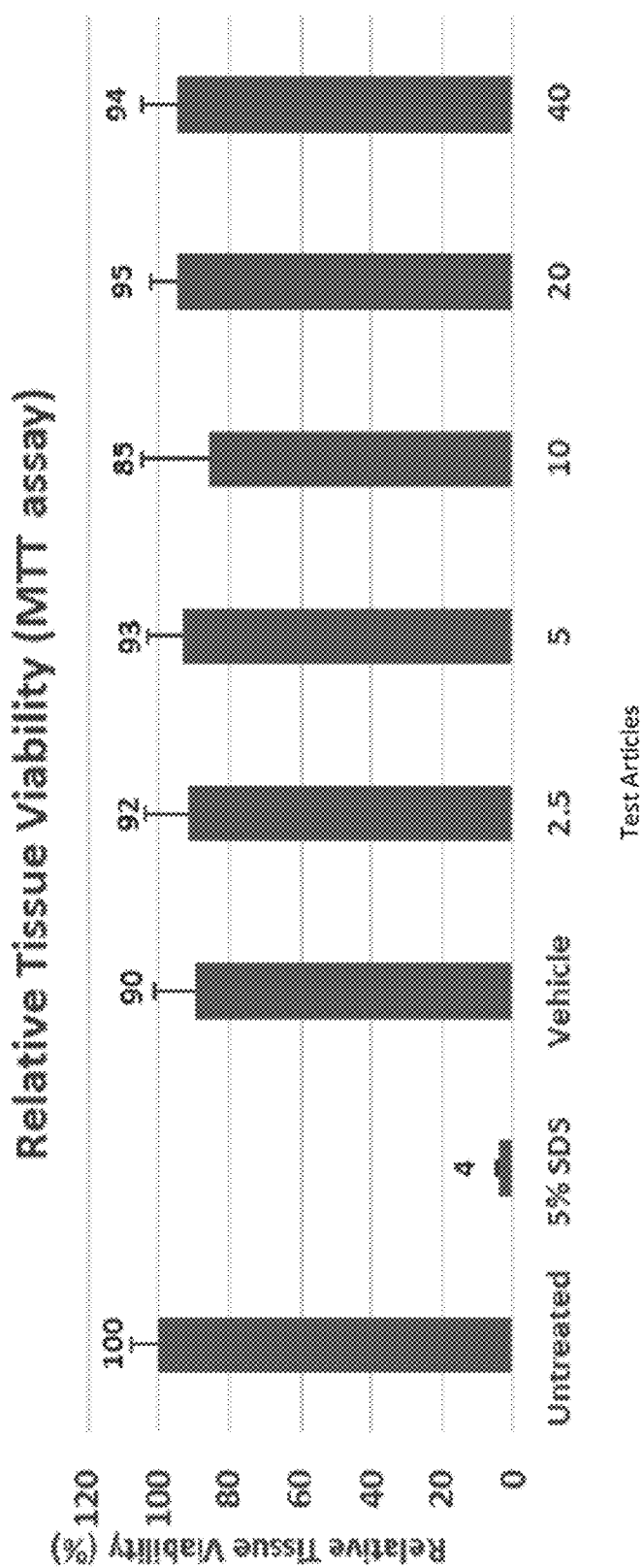
FIG. 11 shows effects of the tested articles on relative tissue viability to examine skin irritation of rhACE-2. 5% SDS: positive control; untreated and vehicle: negative controls; 2.5, 5, 10, 20, and 40 on x-axis: units in µg/ml; Values at each bar: percent viability relative to Untreated group. N=2 per bar.

Assessment of the formulation dispensed was measured using the above process. FIG. 10 shows the graph with the amount dispensed (in grams (g)) versus spray #, whereas the table gives the gross weight and the actual dispensed weights of the formulation. The amount of formulation dispensed from spray bottle 1 was 0.182±0.0139 g and the formulation dispensed from the spray bottle 2 was 0.183±0.015 g. The data reveal that the amount of the formulation dispensed is uniform with a relatively lower standard deviation indicating that the spray pattern was uniform and consistent. In particular, the spray pattern is uniform and consistent with a plume area of ~2.2 $cm^2$ and with the weight dispensed at 0.18 g.

Example 3: Skin Irritation Study of Formulation Comprising rhACE-2

Dermal irritation potential was assessed using the In Vitro EpiDerm™ Skin Irritation Test (EPI-200-SIT). The purpose of this study was to evaluate the effects skin irritation using various concentrations of ACE-2 (e.g., 2.5 μg/ml, 5 μg/ml, 10 μg/ml, 20 μg/ml, and 40 μg/ml) dissolved in one formulation prototype. EpiDerm™ cultures (EPI-200; Lot 34711) were maintained and treated topically and at the end of the treatment, tissue viability was determined using the MTT conversion assay. As a secondary output of skin irritation, levels of the proinflammatory mediator IL-1α were determined.

A total of 24 cultures were assessed, with 5 test articles in each culture. The assays were performed in triplicate. As a positive control to induce irritation, a sample comprising 5% SDS was used. As a negative control, a sample comprising 1×PBS was used.

In particular, the assay medium was pipetted at RT to 6-well plates. Cultures were transferred to 6-well plates in incubated overnight. The next day, 30 μl of test articles were applied at 1 minute intervals. After application of the test articles, the cultures were incubated for 1.5 hours. Cultures were washed with 1×DBPS and transferred to new 6-well plates. After incubation of the cultures for 24 hours, media were collected for IL-1α analysis. The media, if unused, was stored at −20° C. Samples were subjected to IL-1α analysis using Quantikine® ELISA (R&D systems, catalog number: DLA50) according to manufacturer protocol.

After transfer of the cultures to a new 6-well plate and incubation for 18 hours, the cultures were transferred to a 24 well-plate comprising 300 ul of X1 MTT solution (1 mg/ml) in each well. After a series of washes, the cultures were incubated with isopropanol. MTT extracts were transferred to 96 well plates and OD was measured at 570 nm.

Table 11 shows the various test articles examined in this experiment and the formulation composition used in the experiment is shown in Table 12.

TABLE 11

Test Articles

| # | Description |
|---|---|
| 1 | Untreated (Negative Control) |
| 2 | 5% SDS (Positive Control) |
| 3 | Vehicle (solvent blend) |
| 4 | rhACE-2 2.5 ug/ml in solvent blend |
| 5 | rhACE-2 5 ug/ml in solvent blend |
| 6 | rhACE-2 10 ug/ml in solvent blend |
| 7 | rhACE-2 20 ug/ml in solvent blend |
| 8 | rhACE-2 40 ug/ml in solvent blend |

TABLE 12

Formulation Compositions for Test Articles 1-8 of Table 11

| Excipient | % W/W |
|---|---|
| 1X PBS | 78.2 |
| Glycerin | 2.5 |
| Tween 20 | 0.1 |
| Mannitol | 0.1 |
| PEG 400 | 5 |
| Propylene Glycol | 5 |
| Sorbic Acid | 0.1 |
| Sorbitol | 5 |
| HPMC | 4 |

To measure viability, optical density was measured at 570 nm using isopropanol as a blank. Each sample was evaluated in duplicate. Percent cell viability of each sample was determined using the equation: ($OD_{570}$(sample)/Average $OD_{570}$ (untreated))*100. Results were presented as means±SD. As shown in FIG. 11, viability was maintained across each sample treated with rhACE-2, while treatment with the positive control (5% SDS) resulted in a significant decrease in viability. In particular, treatment with rhACE-2 at 0 µg/ml, 2.5 µg/ml, 5 µg/ml, 10 µg/ml, 20 µg/ml, and 40 µg/ml, resulted in relative percent tissue viability values of 90%, 92%, 93%, 85%, 95% and 94% respectively. The mean $OD_{570}$ of the negative control sample was 1.78. The assay met the acceptance criterion demonstrating $OD_{570}$ value of the negative control between ≥1.0 and ≤2.8. Thus, the negative control met this acceptance criterion.

5% SDS (in H2O) solution (i.e., the positive control) met the acceptance criterion if the mean viability of positive control tissues expressed as percentage of the negative control tissues is ≤20%. Here, the mean viability of positive control tissues expressed as percentage of the negative control tissues was 4%, thus meeting this acceptance criterion.

Figure 12:
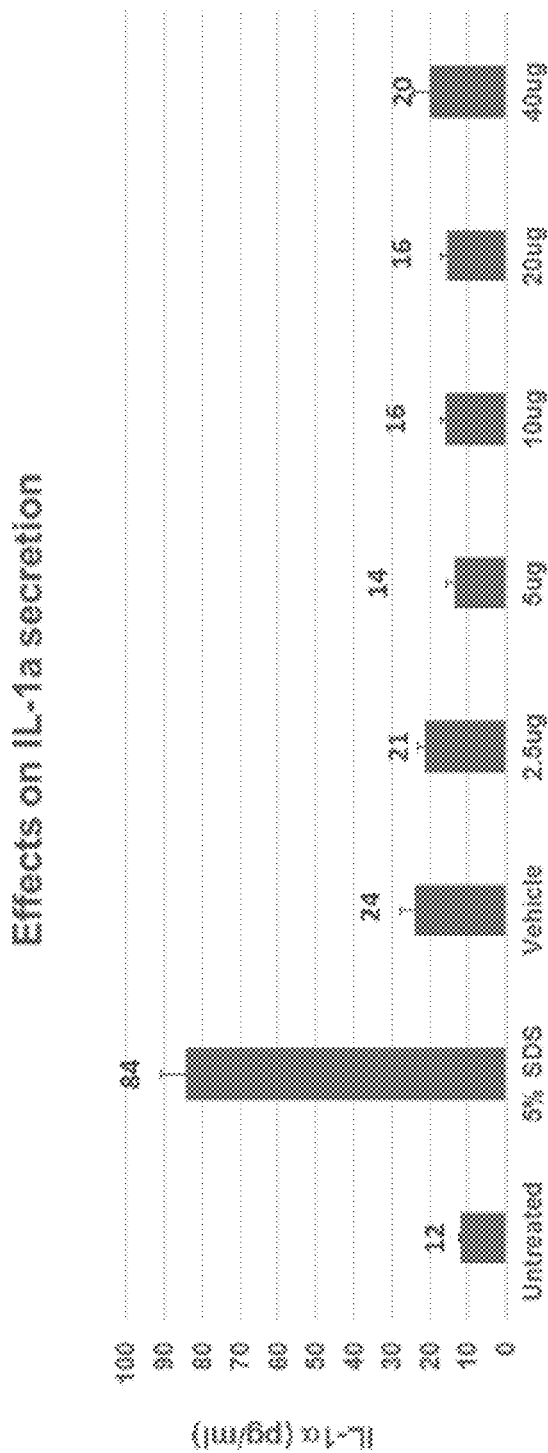
FIG. 12 shows effects of the test articles on secretion of IL-1α to examine skin irritation of rhACE-2. Values at each bar: concentration of secreted IL-1α in pg/ml; 2.5, 5, 10, 20, and 40 on x-axis: units in pg/ml. N=2 per bar.

Next, as described above, secretion of IL-1α was determined. As shown in FIG. 12, each of the samples treated with rhACE-2 showed limited IL-1α secretion, while the positive control sample (5% SDS) demonstrated a significant increase in IL-1α secretion compared to every other group tested. Thus, treatment with any concentration of rhACE-2 resulted in a decrease in IL-1α compared to 5% SDS.

The foregoing data suggest that none of the tested concentrations of rhACE-2 protein were classified as irritating to human skin.

Example 4: Nasal Irritation Study of Formulation Comprising rhACE-2

Next, the effect on nasal irritation was examined in formulations comprising rhACE-2. The formulations were performed using an increased dosage (e.g., 40-50 µg) compared to the study in Example 3. The purpose of this study is to evaluate the effects of various concentrations of rhACE-2 (i.e., 3.06 µg/ml, 6.125 µg/ml, 12.5 µg/ml, 25 µg/ml, 50 µg/ml) on nasal epithelium toxicity using human reconstructed nasal epithelium model (NAS-100-BETA by MatTek).

Table 13 shows the various test articles examined in this experiment and the formulation composition used in the experiment is shown in Table 14.

TABLE 13

Test Articles

| # | Description |
|---|---|
| 1 | Untreated |
| 2 | 5% SDS |
| 3 | Vehicle (solvent blend) |
| 4 | rhACE-2 3.06 ug/ml in solvent blend |
| 5 | rhACE-2 6.125 ug/ml in solvent blend |
| 6 | rhACE-2 12.5 ug/ml in solvent blend |
| 7 | rhACE-2 25 ug/ml in solvent blend |
| 8 | rhACE-2 50 ug/ml in solvent blend |

TABLE 14

Test Articles

| Excipient | % W/W |
|---|---|
| 1X PBS | 78.2 |
| Glycerin | 2.5 |
| Tween 20 | 0.1 |
| Mannitol | 0.1 |
| PEG 400 | 5 |
| Propylene Glycol | 5 |
| Sorbic Acid | 0.1 |
| Sorbitol | 5 |
| HPMC | 4 |

Cultures were maintained and treated topically and at the end of the treatment, tissue viability was determined using the MTT conversion assay as described in Example 3. The Relative Tissue Viability values were determined and used to classify the test articles as irritant or non-irritants according to the assay criteria. As a secondary output, levels of the proinflammatory mediator IL-1α were determined as described in Example 3.

Figure 13:
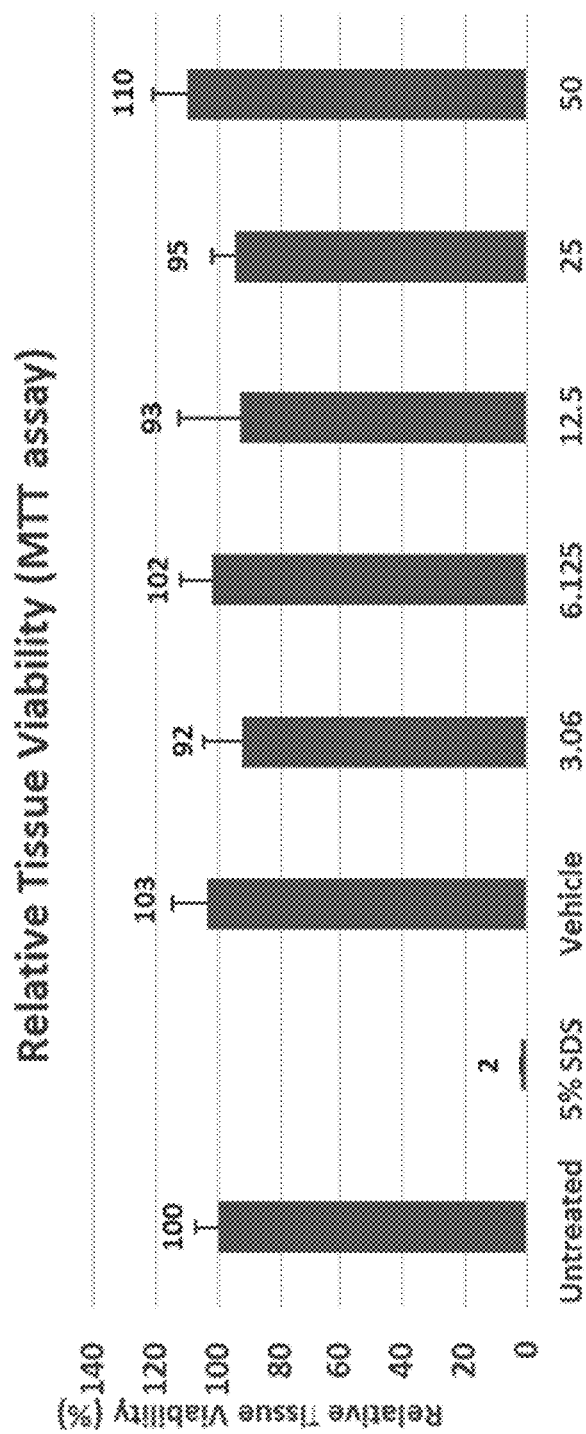
FIG. 13 shows relative tissue viability across various test articles to examine nasal irritation of rhACE-2. Values on x-axis (i.e., 3.06, 6.125, 12.5, 25, and 50) are in µg/ml.
Figure 14:
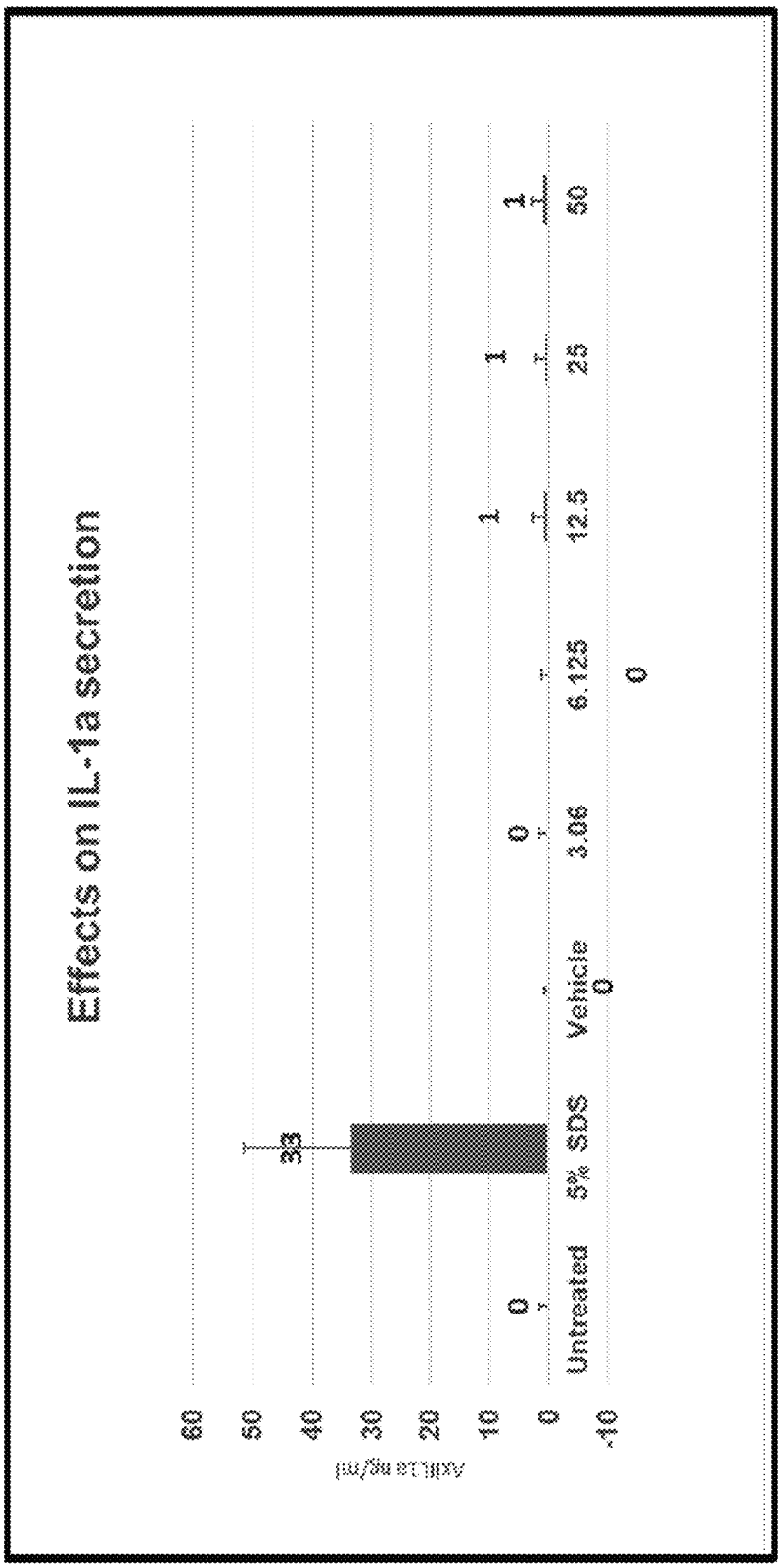
FIG. 14 shows effects of the test articles on secretion of IL-1α to examine nasal irritation of rhACE-2. Values on x-axis (i.e., 3.06, 6.125, 12.5, 25, and 50) are in pg/ml.

As shown in FIG. 13, treatment of cultures at concentrations of rhACE-2 at 0 µg/ml, 3.06 µg/ml, 6.125 µg/ml, 12.5 µg/ml, 25 µg/ml, and 50 µg/ml resulted in relative percent tissue viability values of 103%, 92%, 102, 93%, 95%, and 110% respectively. The mean $OD_{570}$ of the NC tissues was 1.66, thus meeting the acceptance criterion between >1.0 and <2.8, and the mean viability of positive control (e.g., 5% SDS) tissues expressed as percentage of the negative control tissues was 2%, thus meets this acceptance criteria (see e.g., Example 3). Furthermore, as shown in FIG. 14, the average IL-1α levels detected in 0 µg/ml, 3.06 µg/ml, 6.125 µg/ml, 12.5 µg/ml, 25 µg/ml, and 50 µg/ml were 0, 0, 0, 1, 1, 1 ng/ml, respectively. These data suggest that all tested article concentrations were classified as nasal non-irritants. All tested conditions except "3.06" had an SD value <18%, thus meet this acceptance criteria. "3.06" condition demonstrated a standard deviation value of 18.09%.

Example 5: Skin Permeation Study of Formulation comprising rhACE-2

Next, permeation of rhACE-2 into skin samples was determined. Table 15 shows the various test articles examined in this experiment. As shown in Table 15, rhACE-2 was dissolved at 50 ug/ml.

TABLE 15

Test Articles

| # | Name | Description |
|---|---|---|
| 1 | Untreated | PBS used as negative control |
| 2 | Placebo | Vehicle formulation |
| 3 | 50 ug | 50 µg/ml rhACE-2 in Formulation of Tables 12 and 14 |

In order to determine the skin permeation profile, a reconstructed human skin model (Epiderm, EPI-200-X manufactured by MatTek Corporation) was used. This model includes normal, human-derived epidermal keratinocytes (NHEK) which have been cultured to form a multilayered, highly differentiated model of the human epidermis. The NHEK cells are cultured on specially-prepared cell culture inserts using serum free medium and attain levels of differentiation. The EpiDerm Skin Model closely parallels human skin, thus providing a useful in vitro means to assess dermal irritancy and toxicology.

The Formulation prototype was prepared and rhACE-2 was added to a final concentration of 50 µg/ml. After an acclimation period, the skin cultures were treated in triplicates PBS (negative control/baseline), vehicle formulation ("Placebo"), and formulation containing 50 µg/ml ACE-2. At the end of each time point culture medium was completely removed and replaced with fresh medium. The amount of permeated ACE-2 over time was determined by ACE-2 ELISA. Levels of ACE-2 in the receiving medium were determined at the following timepoints: 0 minutes, 5 minutes, 30 minutes, 60 minutes, 180 minutes, 540 minutes, 1260 minutes, and 1440 minutes.

Figure 15:
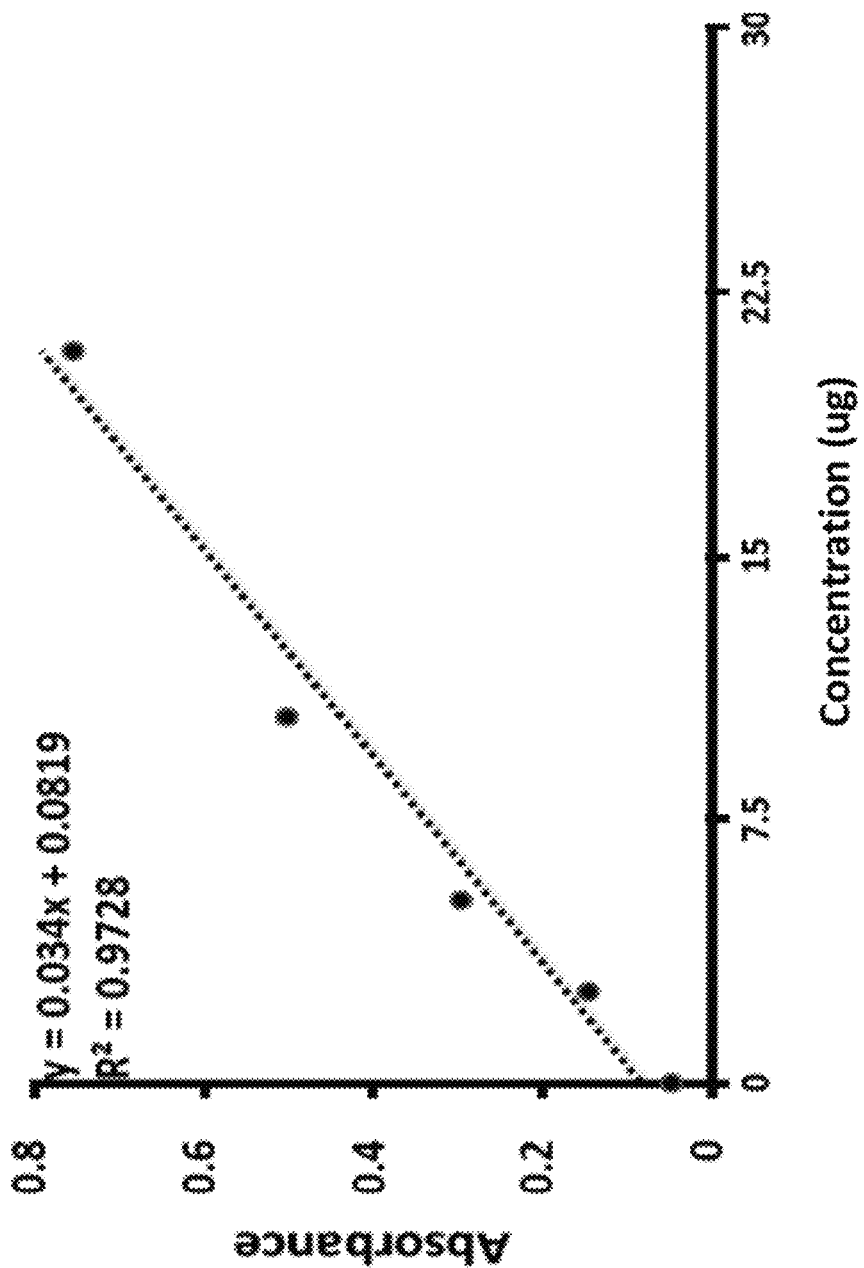
FIG. 15 shows a standard curve generated for rhACE-2 quantification to examine skin permeation of rhACE-2.
Figure 16:
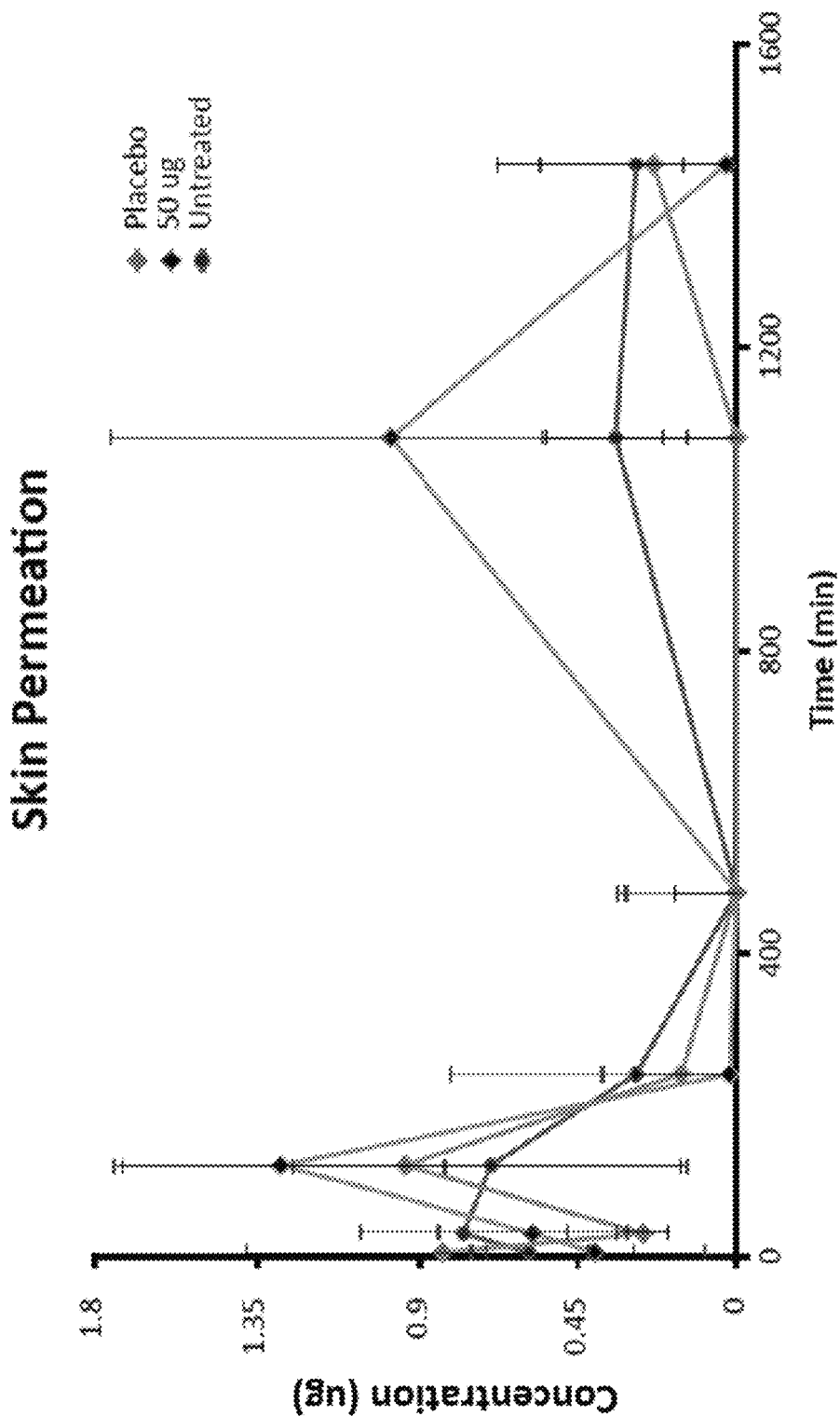
FIG. 16 shows detected levels of rhACE-2 over 1600 minutes to examine skin permeation of rhACE-2. 50 ug: 50 µg/ml rhACE-2.

A standard curve for ACE-2 quantification was generated. See FIG. 15. Standard curve linearity in the tested concentration range was achieved (i.e., 0-20.825 µg/ml). Further, as provided in FIG. 16, study results showed very low to negligible skin permeation values at 5 minutes, 30 minutes, 60 minutes, 180 minutes, 540 minutes, 1260 minutes, and 1440 minutes post application as follows:

"untreated": 0.58, 0.77, 0.69, 0.28, 0, 0.34 and 0.28 ng/ml;
"Placebo": 0.83, 0.26, 0.94, 0.156, 0, 0, 0.23 ng/ml; and
"50 µg/ml": 0.402, 0.578, 1.28, 0.0196, 0. 0.98, 0.029 ng/ml The results showed no significant changes in rhACE-2 values observed between the "50 µg/ml" group and the negative control (i.e., the "Untreated" group) in all the tested time points. These data suggest that there is minimal to negligible permeation of rhACE-2 protein through reconstructed human skin tissue under the tested experimental conditions (i.e., at 50 µg/ml).

Example 6: Nasal Permeation Study of Formulation Comprising rhACE-2

Next, permeation of rhACE-2 into nasal samples was determined. Table 15 shows the various test articles examined in this experiment. As shown in Table 16, rhACE-2 was dissolved at 50 ug/ml.

TABLE 16

| Test Articles | | |
|---|---|---|
| # | Name | Description |
| 1 | Untreated | PBS used as negative control |
| 2 | Placebo | Vehicle formulation |
| 3 | 50 ug | 50 µg/ml rhACE-2 in Formulation of Tables 12 and 14 |

In order to determine the nasal permeation profile, human nasal epithelial cultures (EpiAirway, NAS-100-beta manufactured by MatTek Corporation) were used. The cultures formed a multilayered model of human nasal epithelium.

After an acclimation period, the skin cultures were treated in triplicates with three test articles: PBS (negative control/baseline), vehicle formulation ("Placebo"), and formulation containing 50 ug/ml rhACE-2 ("50 ug"). At the end of each time point, culture medium was completely removed and replaced with fresh medium. The amount of permeated ACE-2 over time was determined by rhACE-2 ELISA. Levels of ACE-2 in the receiving medium were determined at the following timepoints: 0 minutes, 5 minutes, 30 minutes, 60 minutes, 180 minutes, 540 minutes, 1260 minutes, and 1440 minutes.

Figure 17:
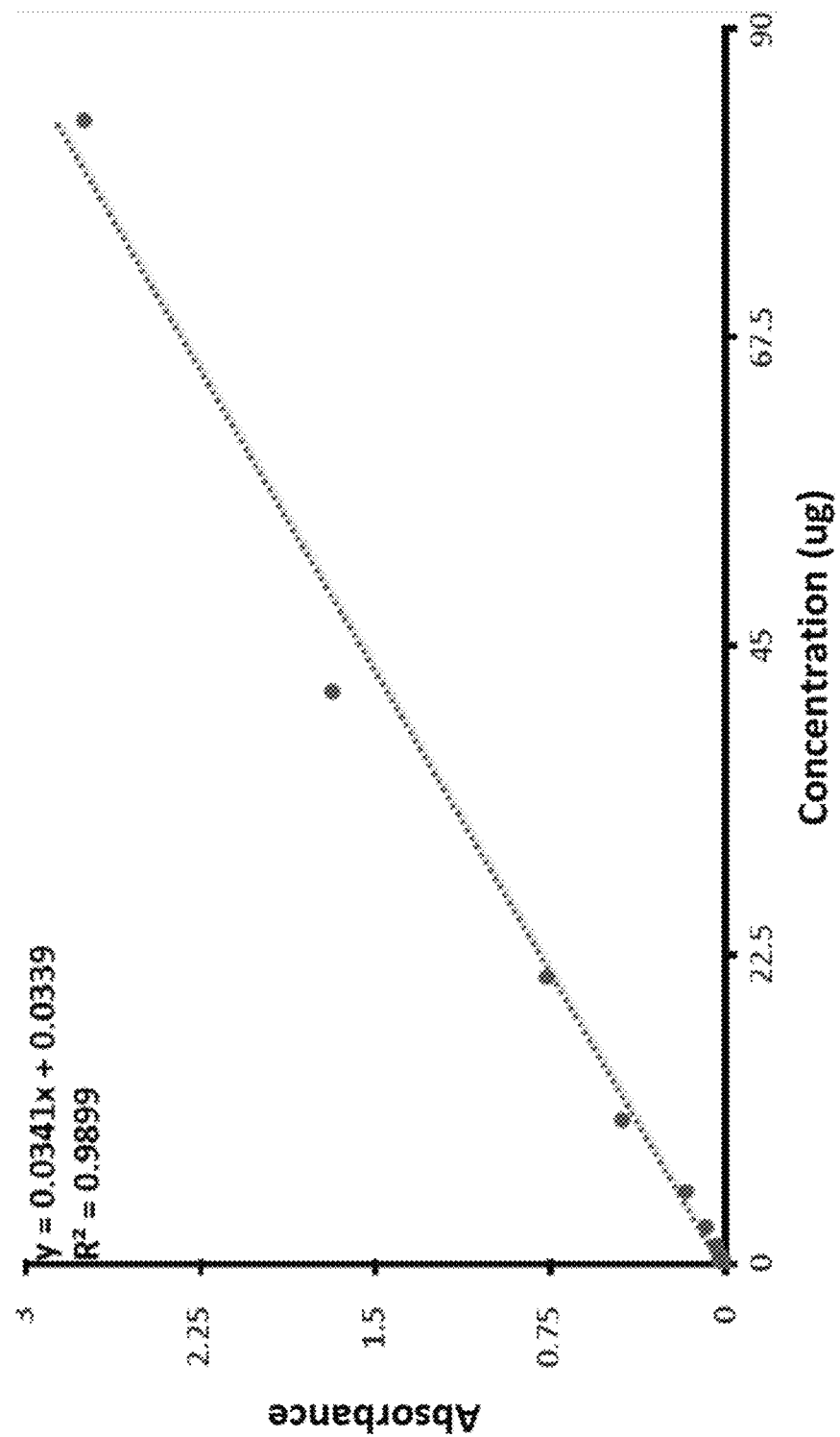
FIG. 17 shows a standard curve generated for rhACE-2 quantification to examine nasal permeation of rhACE-2.
Figure 18:
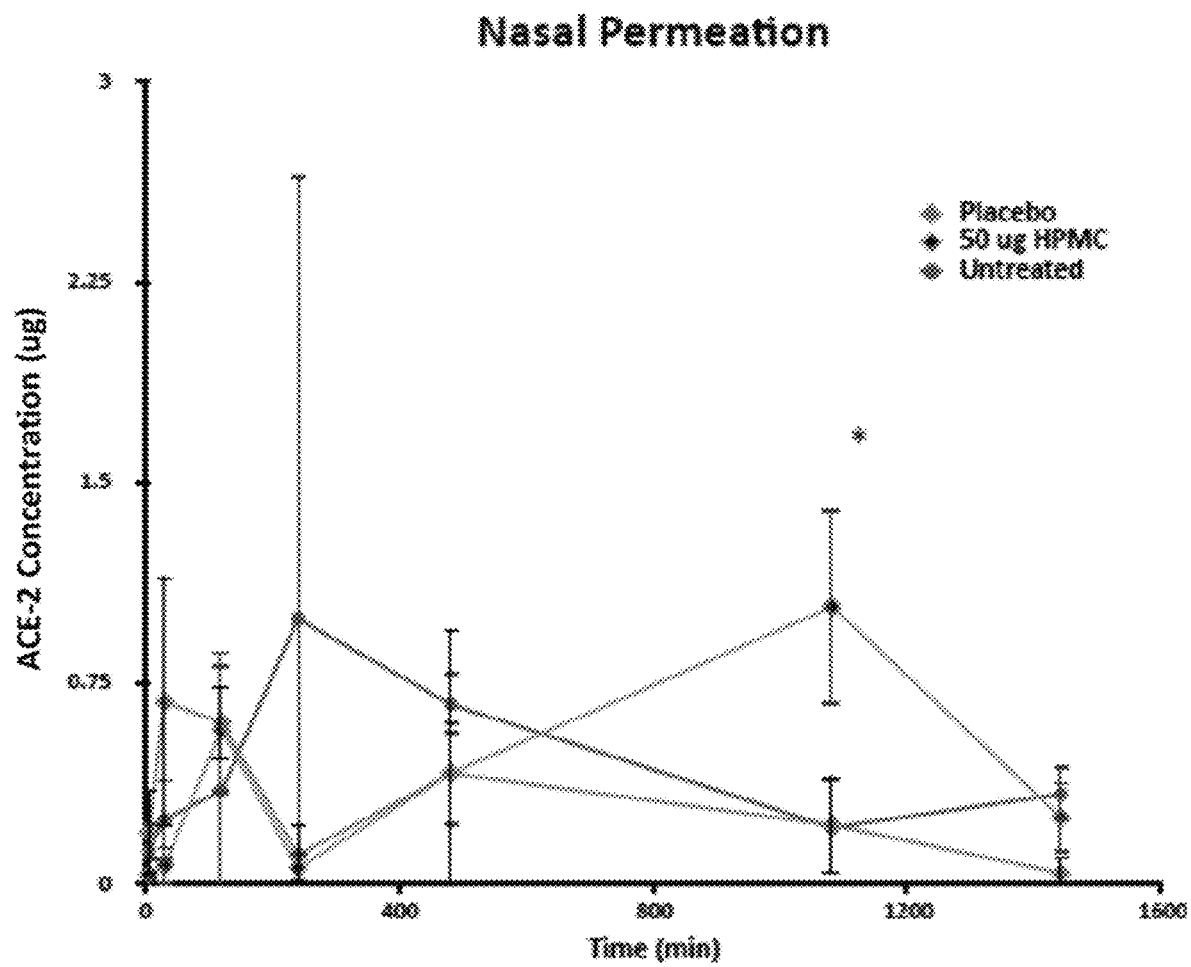
FIG. 18 shows detected levels of rhACE-2 over 1600 minutes to examine nasal permeation of rhACE-2. 50 ug: 50 µg/ml rhACE-2. *: p-value<0.05.

A standard curve for ACE-2 quantification was generated. See FIG. 17. Standard curve linearity in the tested concentration range was achieved (i.e., 0-20.825 µg/ml). Further, as provided in FIG. 18, study results showed very low to negligible skin permeation values at 5 minutes, 30 minutes, 60 minutes, 180 minutes, 540 minutes, 1260 minutes, and 1440 minutes post application as follows:

"untreated": 0.124, 0.24, 0.35, 0.99, 0.67, 0.21 and 0.33 ng/ml

"Placebo": 0.19, 0.682, 0.605, 0.1089, 0.413, 0.22 and 0.0416 ng/ml

"50 µg/ml": 0.035, 0.07, 0.57, 0.06, 0.413, 1.03, 0.249 ng/ml

The results showed no significant changes in rhACE-2 values observed between the "50 µg/ml" group and the negative control (i.e., the "Untreated" group) in all the tested time points. These data suggest that there is minimal to negligible permeation of rhACE-2 protein through reconstructed human nasal tissue under the tested experimental conditions (i.e., at 50 µg/ml).

Example 7: Cytotoxicity, Antibacterial Activity, and Antiviral Efficacy of Formulations Comprising rhACE-2

Next, cytotoxicity, antibacterial activity, and antiviral efficacy of formulations comprising rhACE-2 were analyzed. Here, the test articles shown in Table 17 were examined.

TABLE 17

| Test Articles | | |
|---|---|---|
| Test Article | Name | Drug |
| 1 | TFP-1 | HPMC Formulation + rhACE-2 (SinoBiologics) |
| 2 | TFP-2 | HPMC Formulation + rhACE-2 (RayBiotech) |
| 3 | TFP-3 | 1 × PBS + rhACE-2 (RayBiotech) |
| 4 | TFP-4 | HPMC Formulation (Placebo) |
| 5 | TFP-5 | 1 × PBS (Placebo) |
| 6 | — | 1 × PBS + ACE-2 (SinoBiologics) |

The starting concentration for TFP 6 was 25 µg of ACE 2. It was serially diluted 2-fold 8 times up the plate. The last dilution was 0.195 ug (e.g., dilutions of 0.195 µg, 0.391 µg, 0.781 µg, 1.563 µg, 3.125 µg, 6.25 µg, 12.5 µg, and 25 µg), as shown in Table 18 below.

Test articles 1-3 of Table 17 were provided at a stock concentration of 500 µg/mL. All five test articles were added to the first well of a dilution plate and subsequently serially diluted 2-fold in sterile water as shown in the Tables 18. 50 µL of each test article dilution (1-8) were then mixed at a ratio of 1:1 with 2× viral culture medium containing SARS-CoV-2 at a concentration of approximately 200 TCID50 per 50 µL.

TABLE 18

Serial Dilutions of Samples for Antiviral Activity and Cytotoxicity Assays.

| | Test Articles 1-5 | | | Test Article 6 | | |
|---|---|---|---|---|---|---|
| Sample | Dilution | Conc of sample (μg/mL) | Conc on cells (μg/mL) | Dilution | Conc of sample (μg/mL) | Conc on cells (μg/mL) |
| 1 | Neat | 500 | 250 | Neat | 25 | 25 |
| 2 | 1:02 | 250 | 125 | 1:02 | 12.5 | 12.5 |
| 3 | 1:04 | 125 | 62.5 | 1:04 | 6.25 | 6.25 |
| 4 | 1:08 | 62.5 | 31.25 | 1:08 | 3.125 | 3.125 |
| 5 | 1:16 | 31.25 | 15.6 | 1:16 | 1.56 | 1.56 |
| 6 | 1:32 | 15.6 | 7.8 | 1:32 | 0.78 | 0.78 |
| 7 | 0.08611111 | 7.8 | 3.9 | 0.08611111 | 0.39 | 0.39 |
| 8 | 0.13055556 | 3.9 | 2 | 0.13055556 | 0.2 | 0.2 |

The mixture of virus and test article was then plated onto 96-well plates of confluent Vero E6 cells, in triplicate (duplicate for test article 6). Test article 6 was provided by IITRI neat at a stock concentration of 50 μg/mL but otherwise diluted 2-fold as shown below.

Test articles will be diluted as shown in the Table 19, and mixed 1:1 with 2× bacterial medium containing MRSA or MSSA.

TABLE 19

Serial Dilutions of Samples for Antimicrobial activity against MRSA and MSSA

| | Test Articles 1-5 | | Test Article 6 | | Control- Methicillin | |
|---|---|---|---|---|---|---|
| Sample | Dilution | Concentration (μg/mL) | Dilution | Concentration (μg/mL) | Dilution | Concentration (μg/mL) |
| 1 | Neat | 250 | Neat | 12.5 | Neat | 200 |
| 2 | 1:02 | 125 | 1:02 | 6.25 | 1:02 | 100 |
| 3 | 1:04 | 62.5 | 1:04 | 3.125 | 1:04 | 50 |
| 4 | 1:08 | 31.25 | 1:08 | 1.56 | 1:08 | 25 |
| 5 | 1:16 | 15.6 | 1:16 | 0.78 | 1:16 | 12.5 |
| 6 | 1:32 | 7.8 | 1:32 | 0.39 | 1:32 | 6.25 |
| 7 | 0.08611111 | 3.9 | 0.08611111 | 0.2 | 0.08611111 | 3.13 |
| 8 | 0.13055556 | 2 | 0.13055556 | 0.1 | 0.13055556 | 1.57 |
| 9 | 0.21944444 | 1 | 0.21944444 | 0.05 | 0.22569444 | 0.781 |
| 10 | 0.40972222 | 0.5 | 0.40972222 | 0.025 | 0.40972222 | 0.391 |
| 11 | 0.77777778 | 0.25 | 0.77777778 | 0.0125 | 0.77777778 | 0.195 |
| 12 | 1.51388889 | 0.125 | 1.51388889 | 0.00625 | 1.51388889 | 0.098 |

African green monkey kidney (Vero E6) cells were used for the study. The cells were maintained in Dulbecco's Minimum Essential Medium with 10% fetal calf serum. All growth media contains heat-inactivated fetal calf serum and antibiotics. 2019 Novel Coronavirus, Isolates hCoV-19/USA-WA1/2020 ("WA"), hCoV-19/South Africa/KRISP-K005325/2020 ("SA") and hCoV-19/England/204820464/2020 ("UK"), SARS-CoV-1 strain Urbani and MERS-CoV strain EMC/2012 were used. The viruses were stored at approximately ≤−65° C. prior to use.

For the cytotoxicity study, samples were evaluated in triplicate. Vero E6 cells were cultured in 96 well plates prior to the day of the assay. Cells were at greater than 90% confluency at the start of the study. Test articles were serially diluted 2-fold and then were added to the respective wells in triplicate (duplicate for test article 6). The plates then were incubated in a humidified chamber at 37° C.±2° C. in 5±2% CO2. At 48 hrs±4 hrs post inoculation, wells were assessed for cytopathic effect (CPE) by neutral red uptake or MTT assay.

Figure 19:
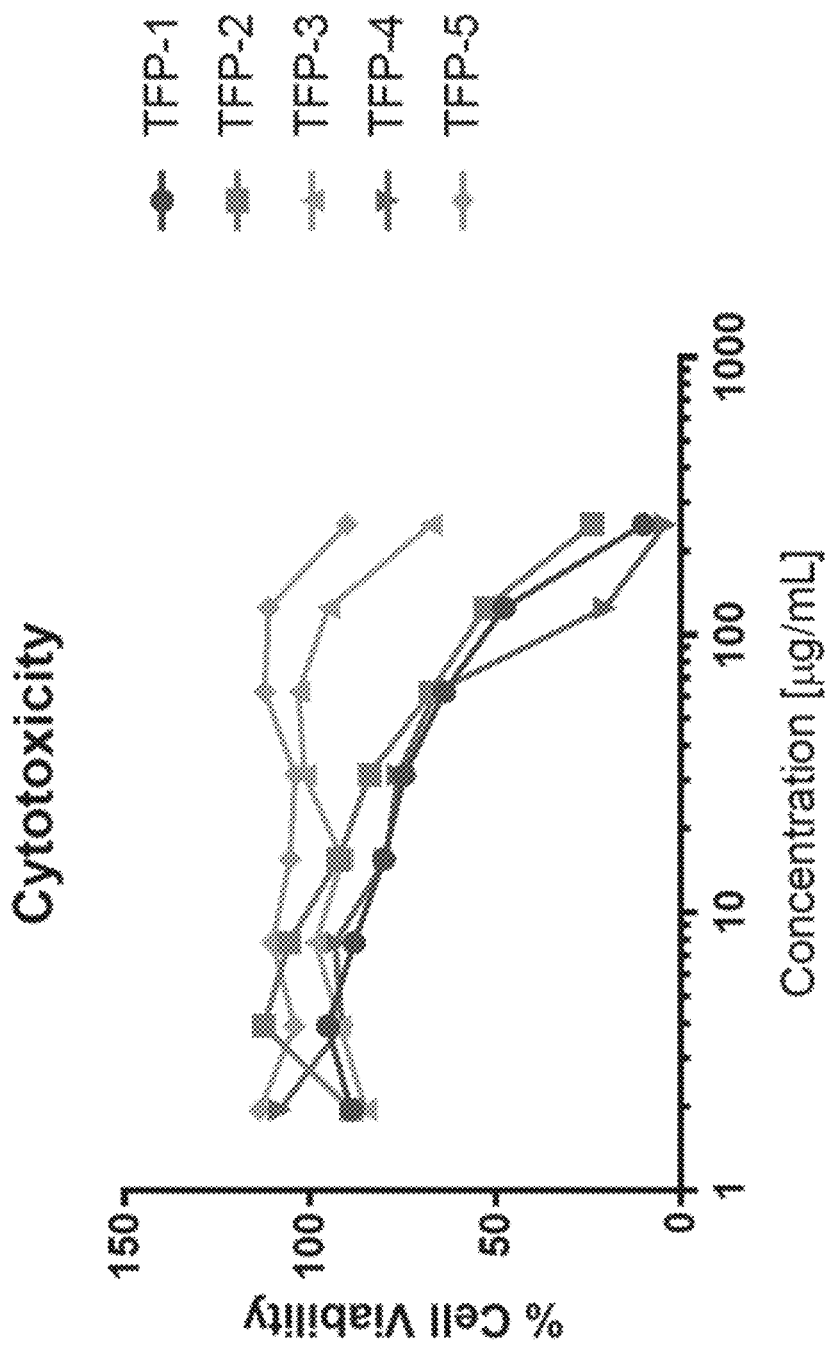
FIG. 19 show percent cell viability in cells treated with TFP-1-TFP-5 at increasing concentrations of test articles. TFP: test compounds.

As shown in FIG. 19, there remained viable through 100 μg/ml of test articles, and there was not a significant drop off at concentrations under 100 μg/ml of test articles. These data demonstrate that the formulations do not possess high toxicity.

For the antibacterial assay, all test articles were serially diluted 2-fold in trypticase soy broth (TSB). The positive control used was methicillin. Drug dilutions were mixed with approximately 1,000 CFU per well of either methicillin-resistant *S. aureus* (MRSA) strain ATCC 33591, or methicillin-sensitive *S. aureus* (MSSA) strain ATCC 29213. Drug dilution/bacterial mixtures were added to triplicate wells (duplicate wells for test article 6) of a 96-well plate and incubated at 37° C.±2° C. for 24±2 hrs and at 48±2 hrs, if necessary. The plates were then either read at OD600 or visually read, with each well scored for +/0 for growth/no growth.

Figure 20:
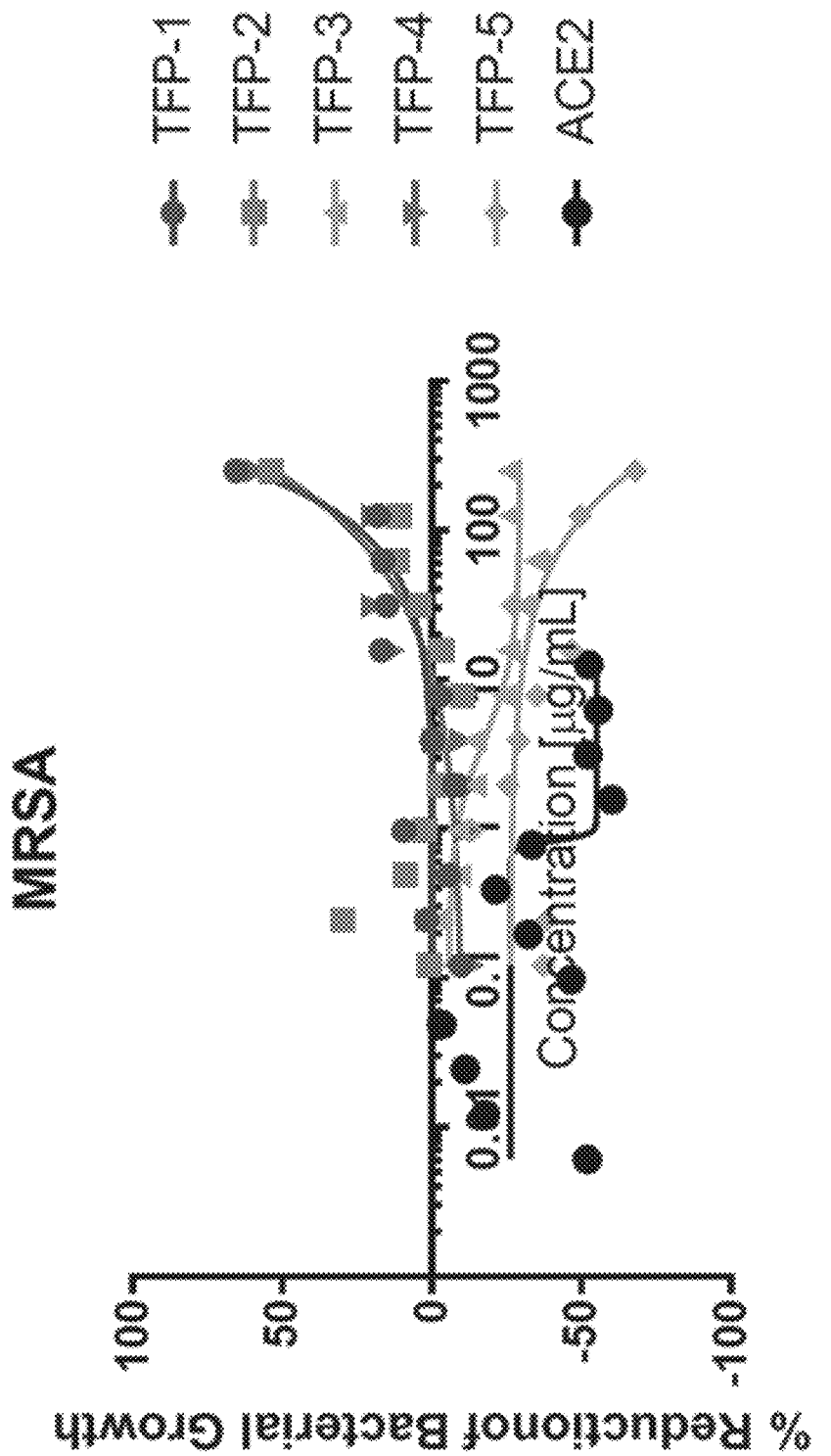
FIG. 20 shows percent reduction of bacterial growth (MRSA) at increasing concentrations of test articles. ACE2: recombinant human ACE-2.
Figure 21:
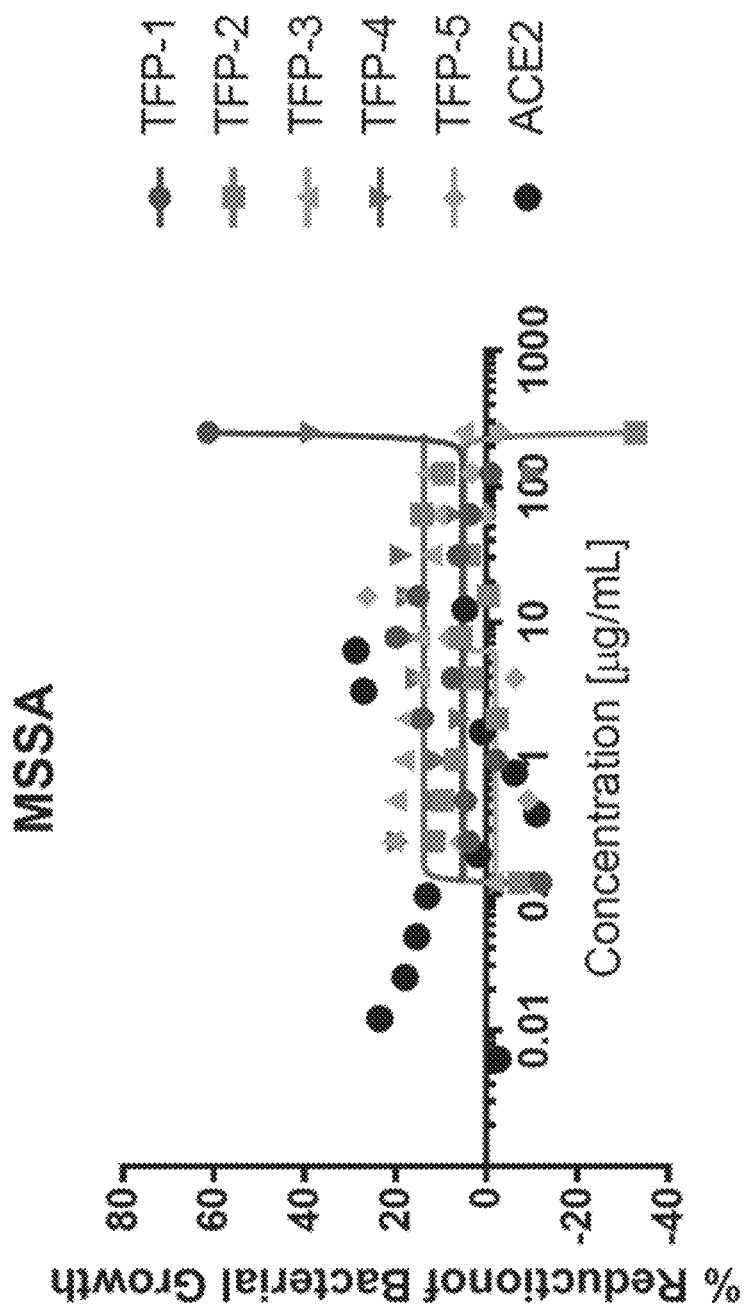
FIG. 21 shows percent reduction of bacterial growth (MSSA) at increasing concentrations of test articles.
Figure 22:
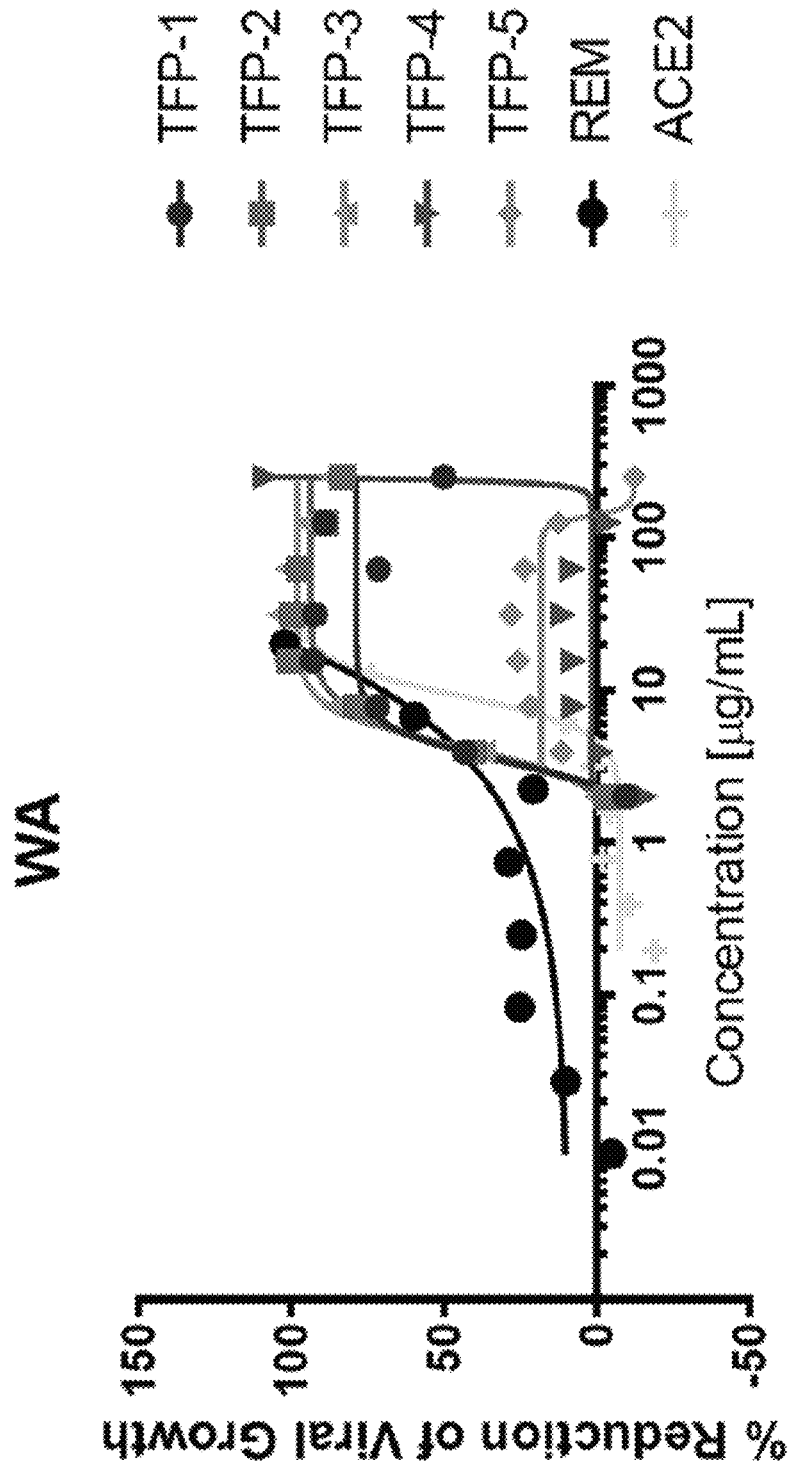
FIGS. 22-29 show percent reduction of viral growth over various concentrations of at increasing concentrations of test articles tested against the Washington state SARS-CoV-2 variant. REM: Remdesivir; WA: hCoV-19/USA-WA1/2020 variant.
Figure 23:
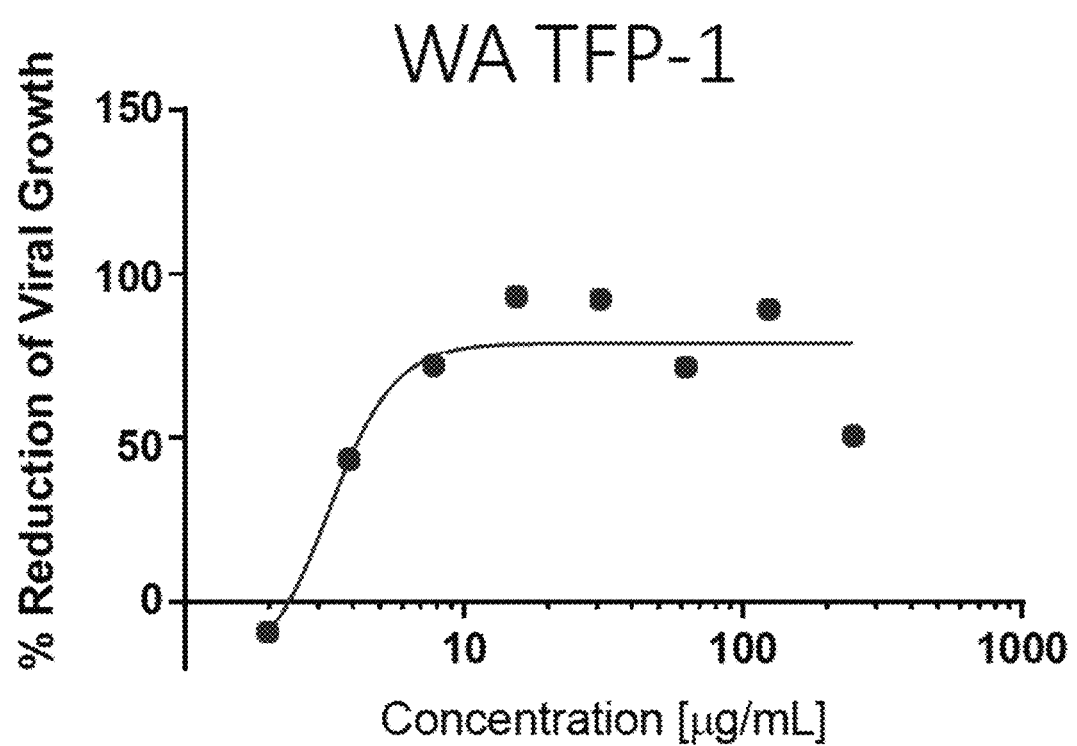
Figure 24:
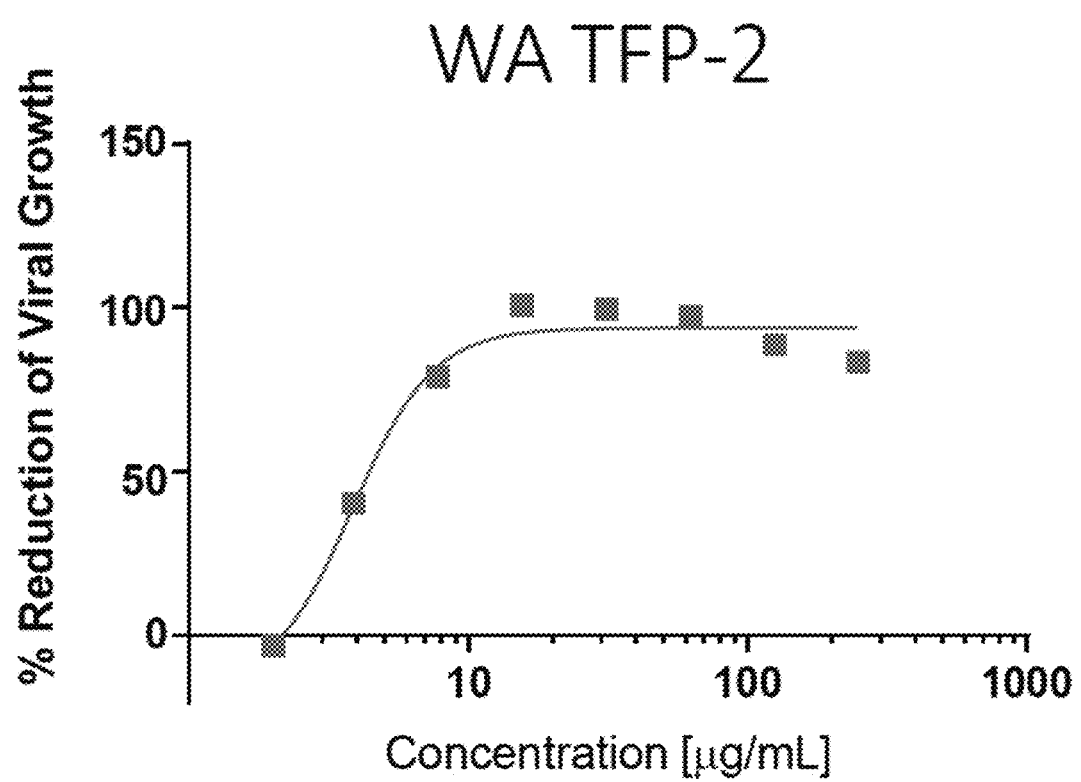
Figure 25:
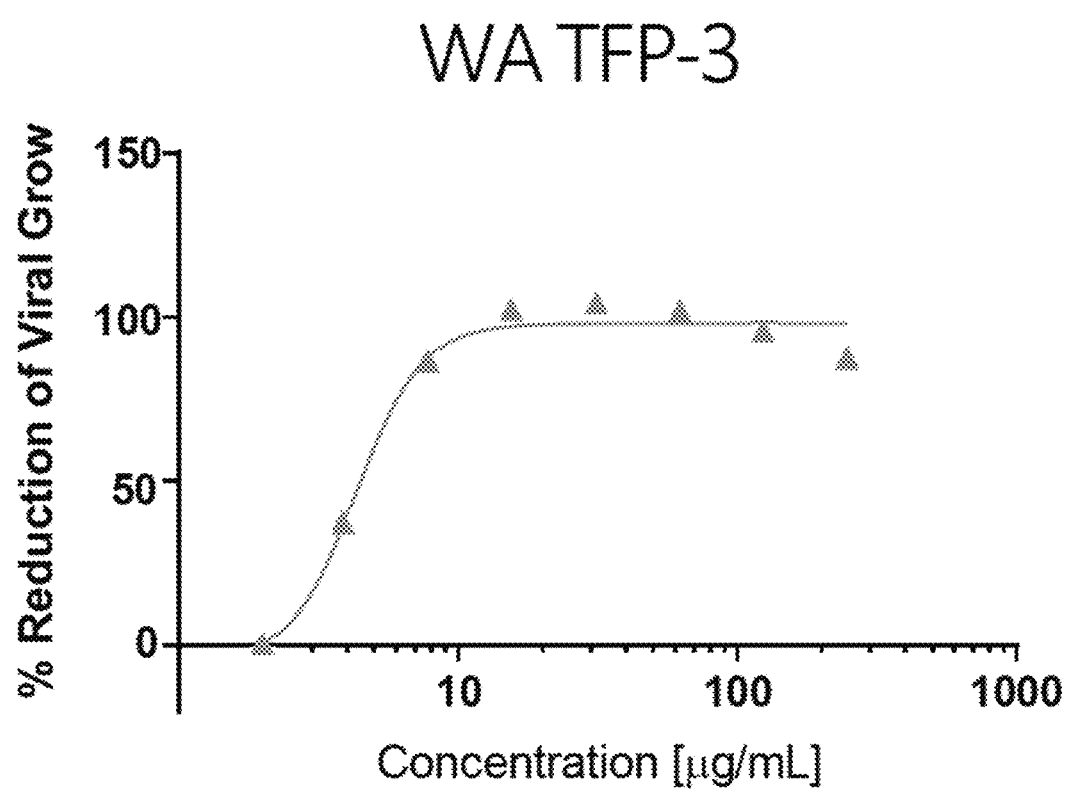
Figure 26:
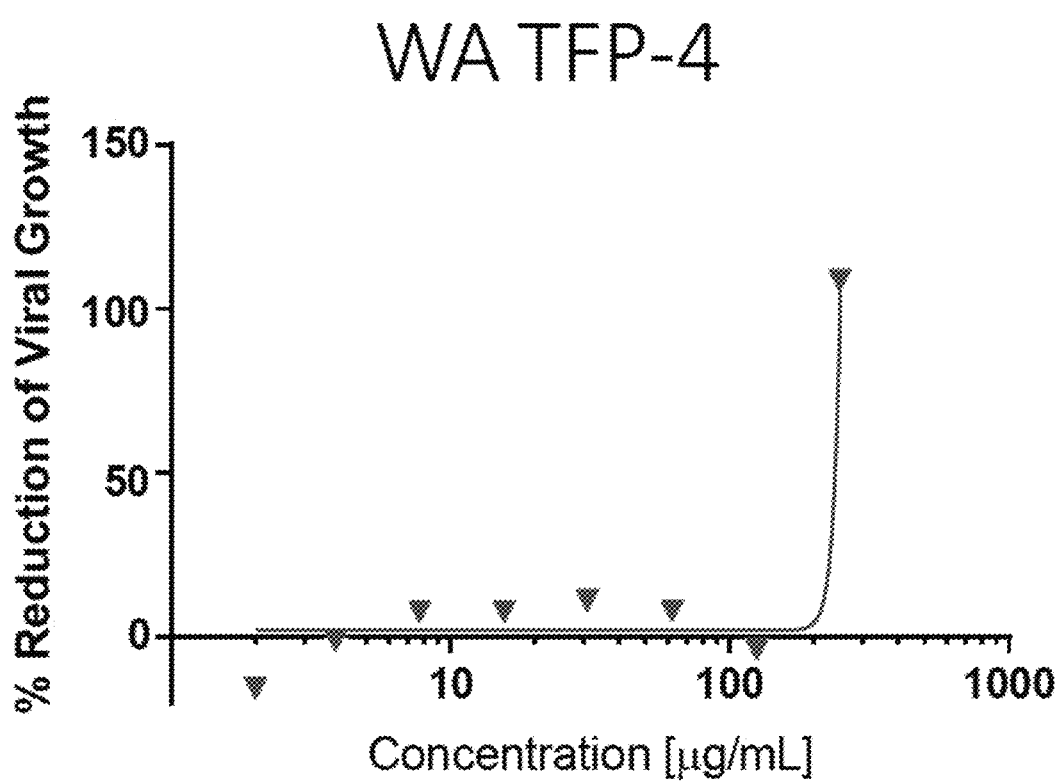
Figure 27:
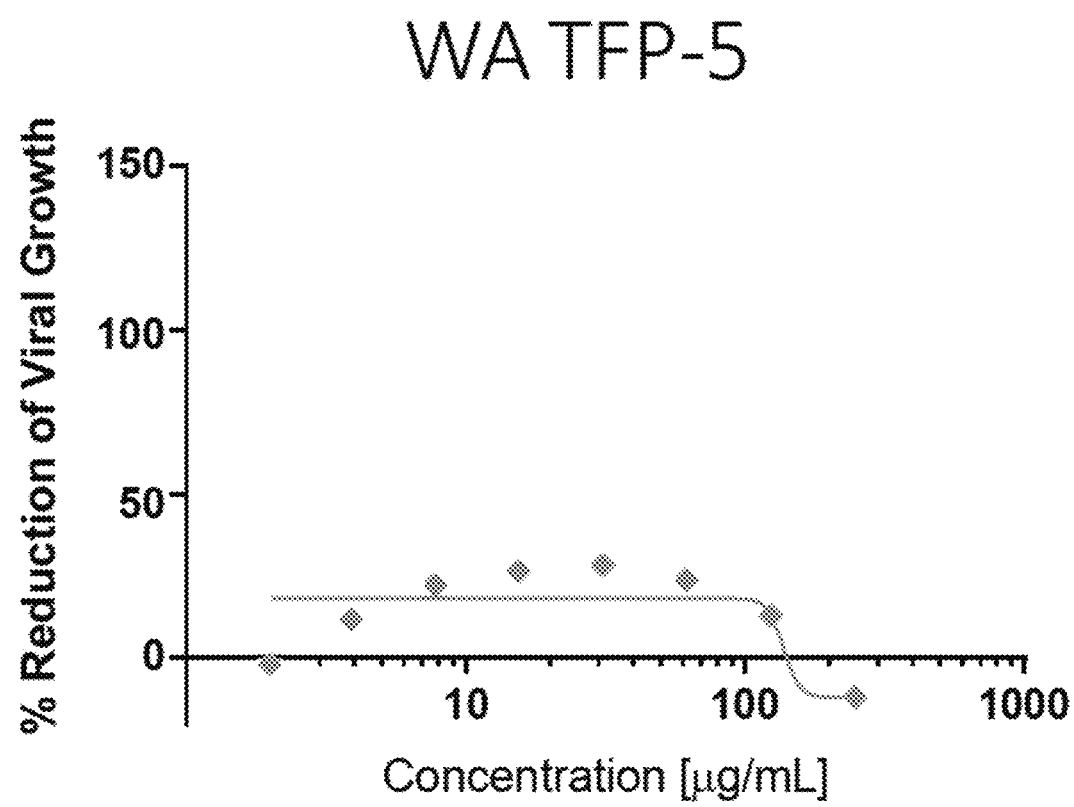
Figure 28:
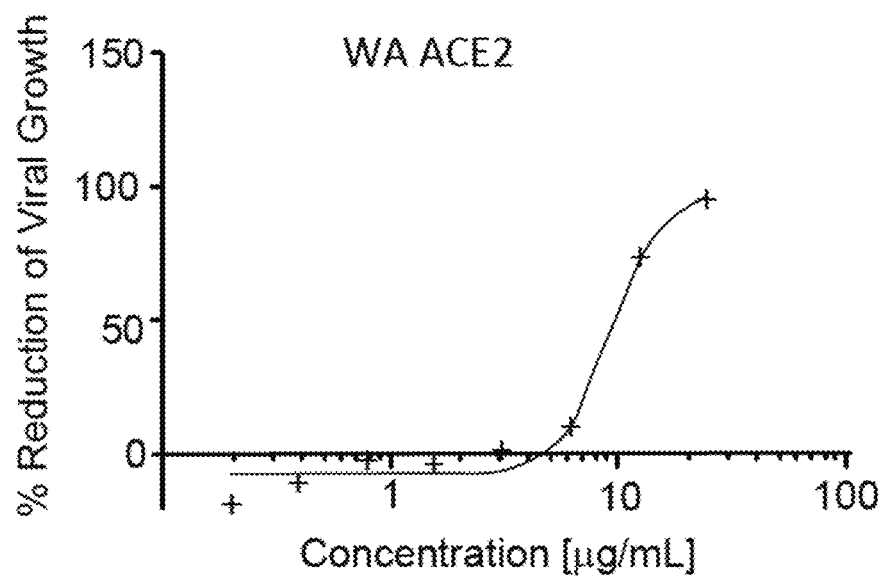
Figure 29:
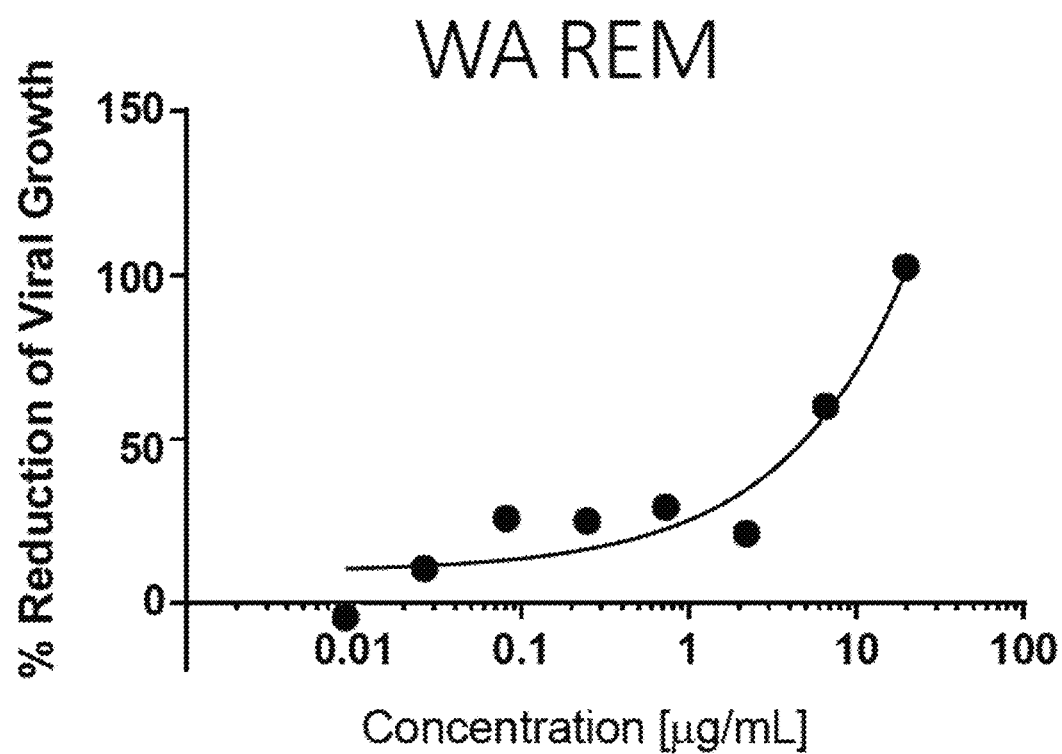
Figure 30:
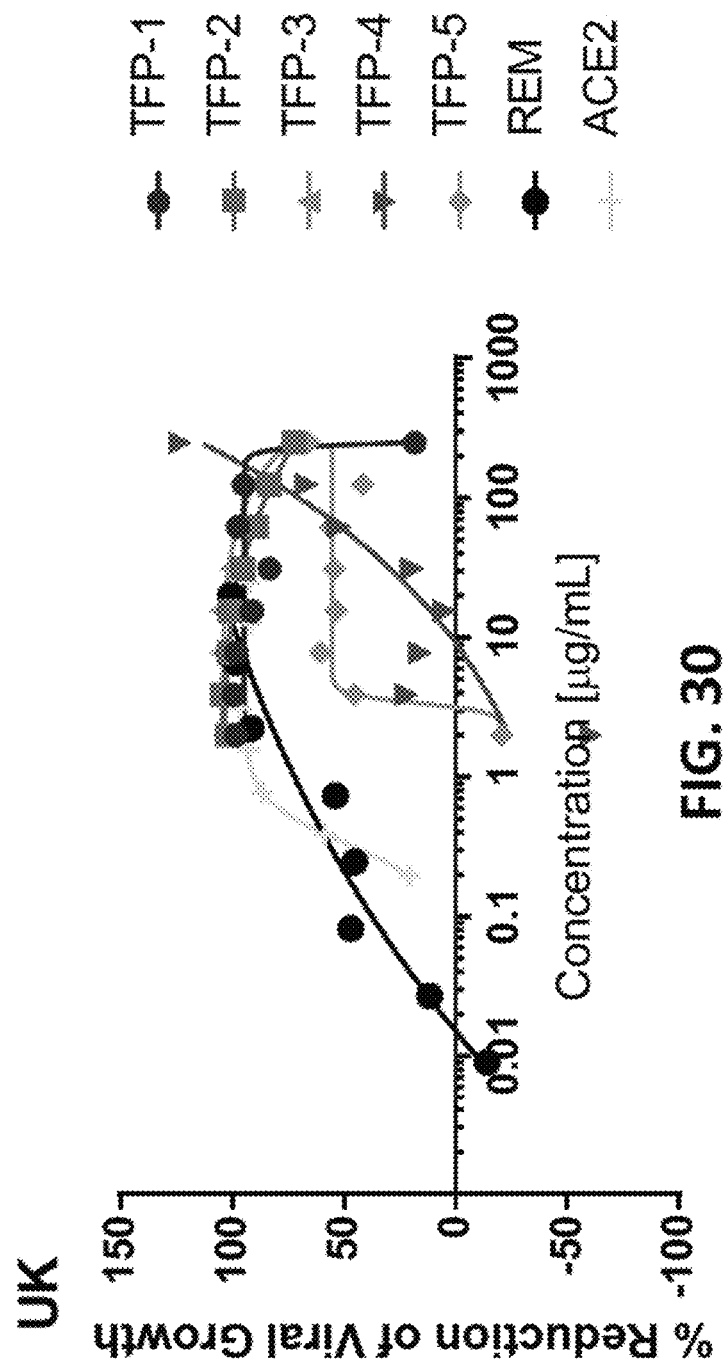
FIGS. 30-37 show percent reduction of viral growth over various concentrations of at increasing concentrations of test articles tested against the United Kingdom SARS-CoV-2 variant. UK: hCoV-19/England/204820464/2020.
Figure 31:
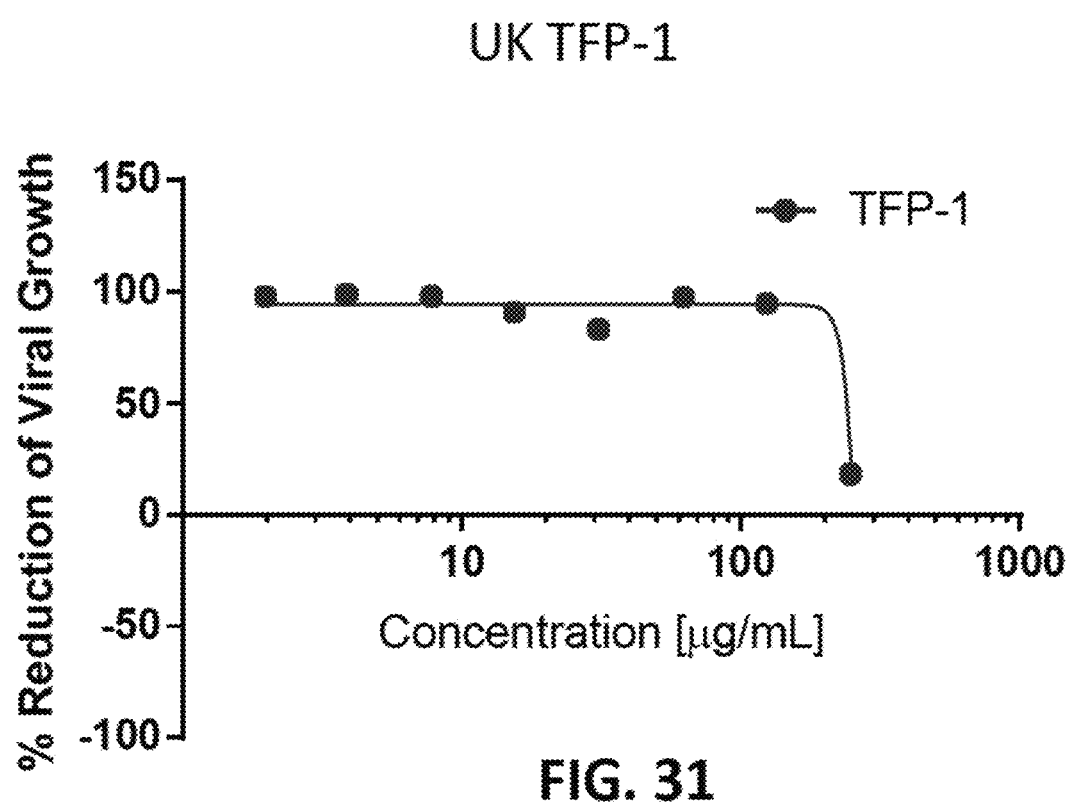
Figure 32:
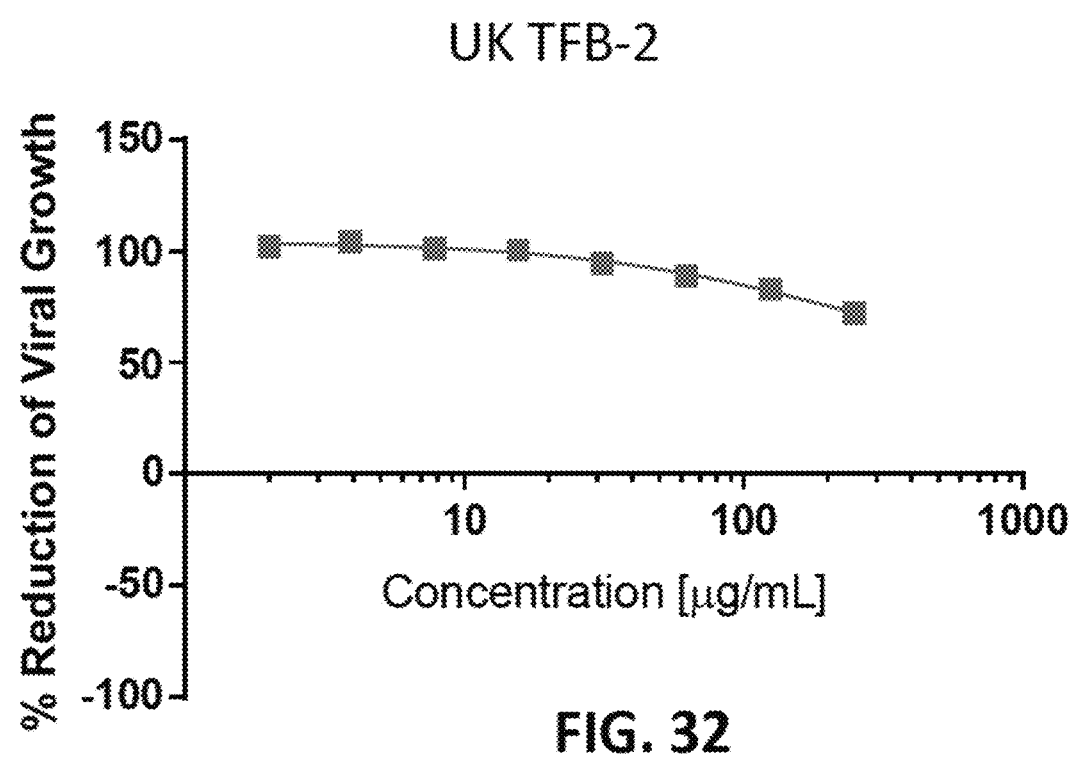
Figure 33:
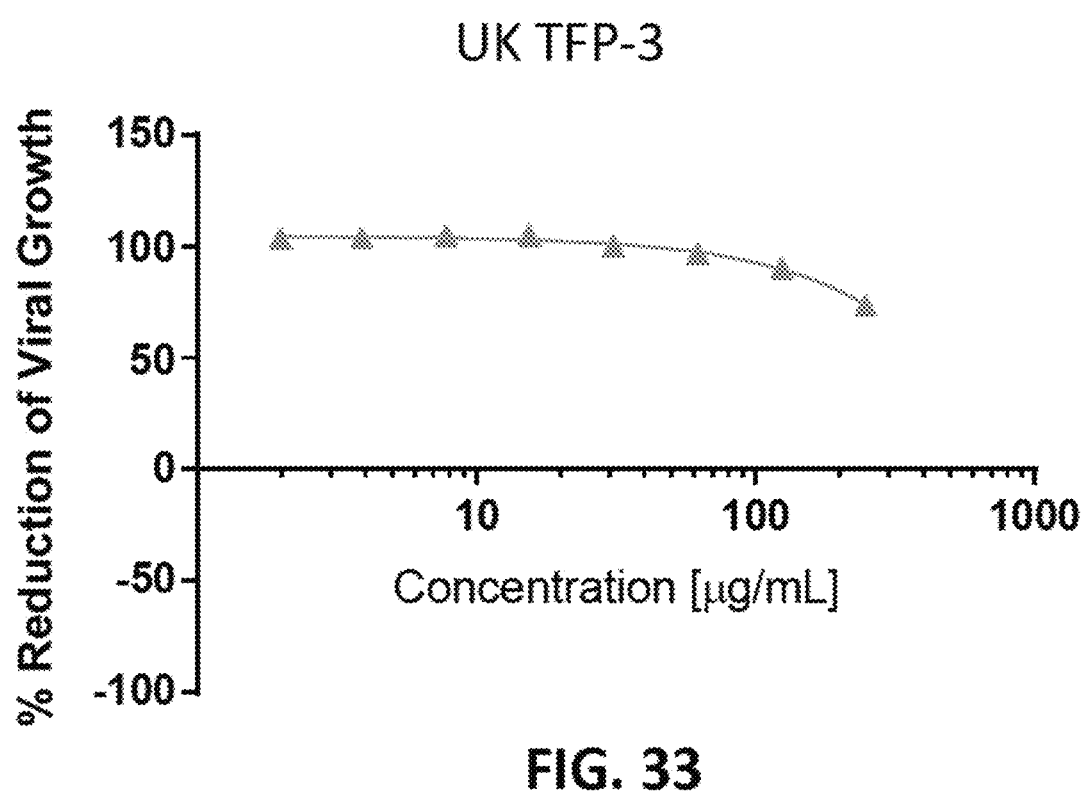
Figure 34:
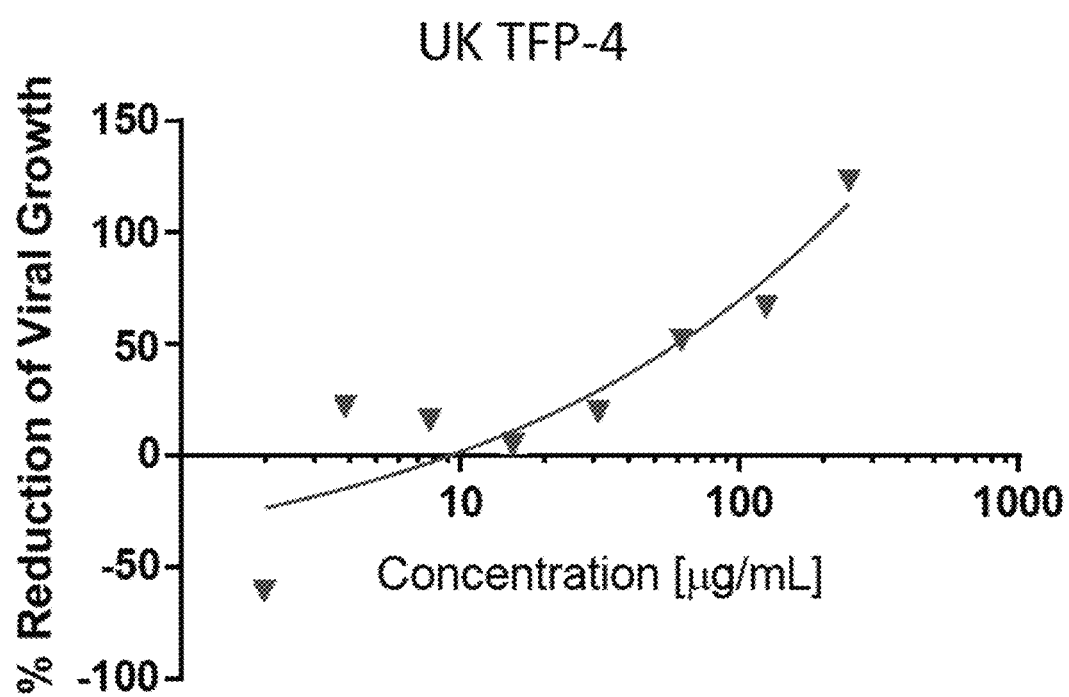
Figure 35:
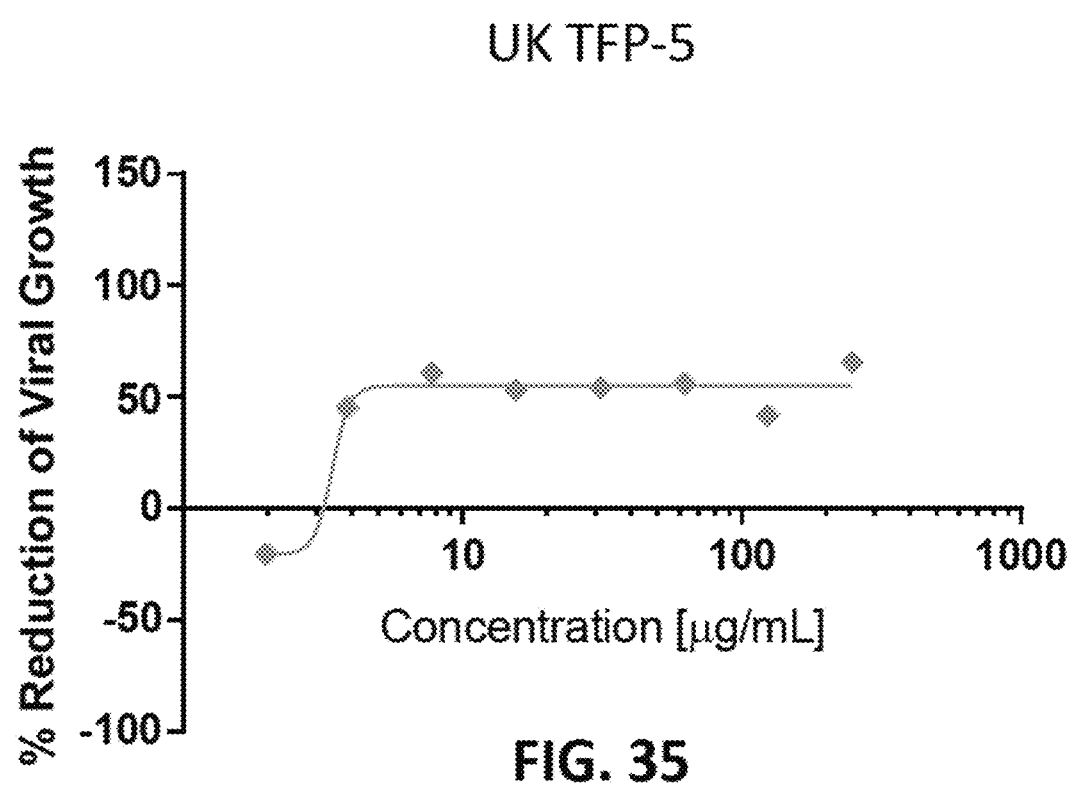
Figure 36:
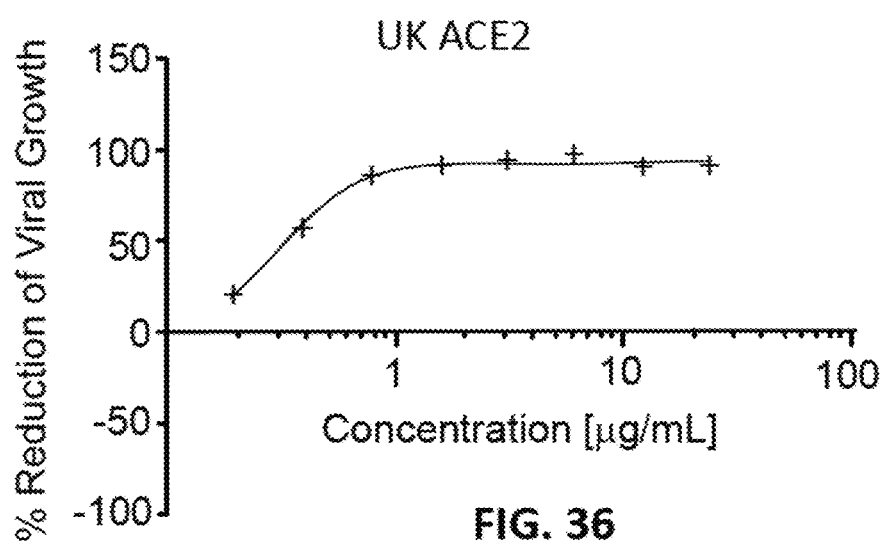
Figure 37:
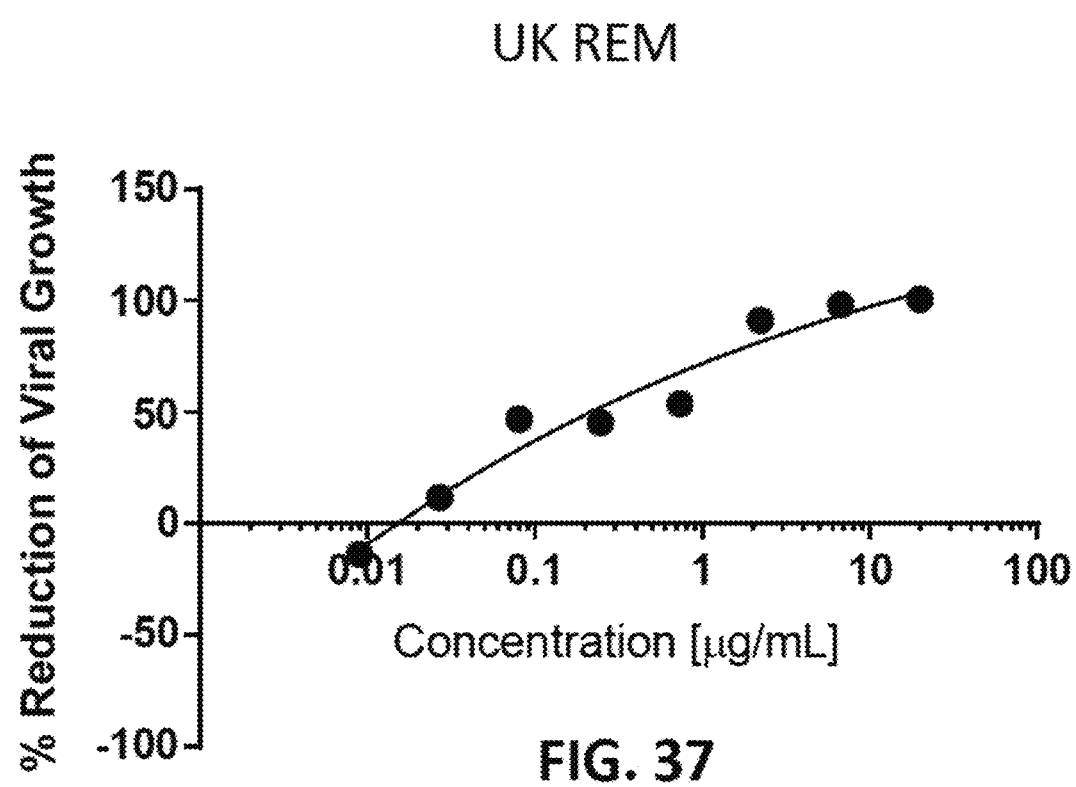
Figure 38:
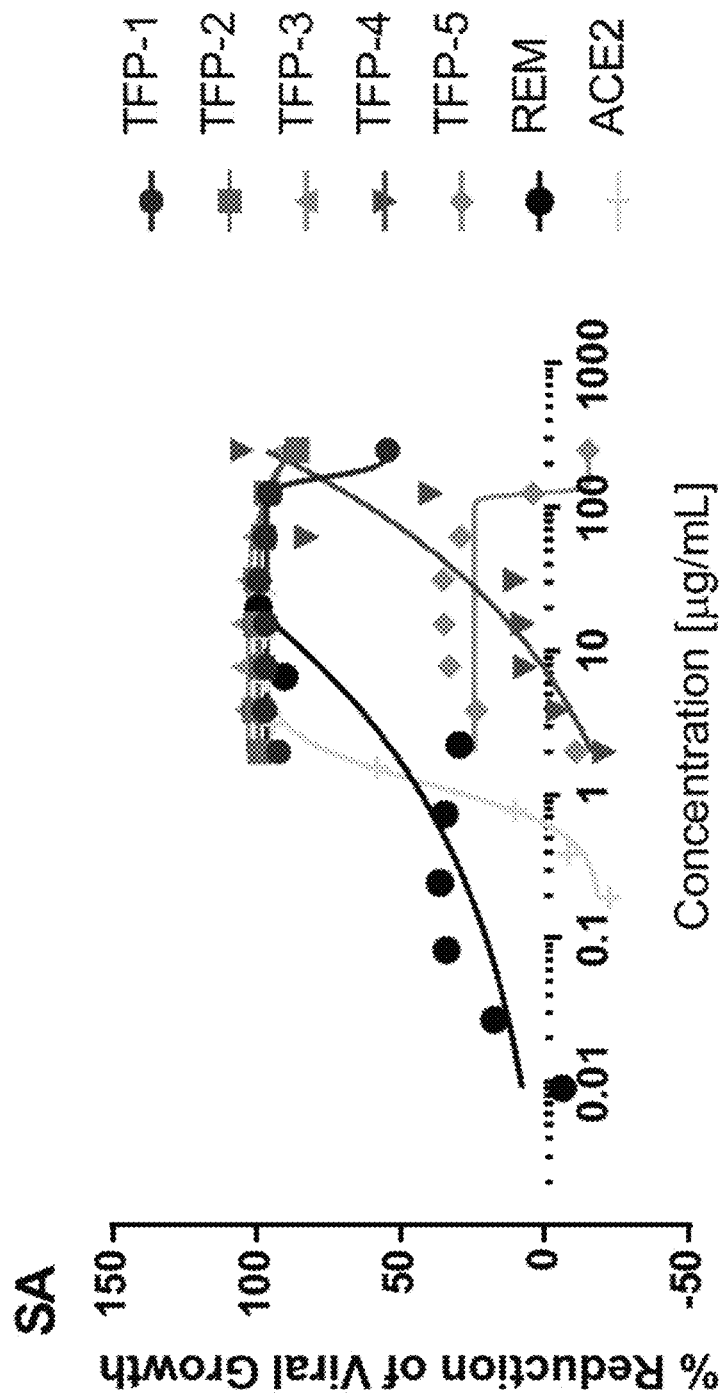
FIGS. 38-45 show percent reduction of viral growth over various concentrations of at increasing concentrations of test articles tested against the South African SARS-CoV-2 variant. SA: hCoV-19/South Africa/KRISP-K005325/2020.
Figure 39:
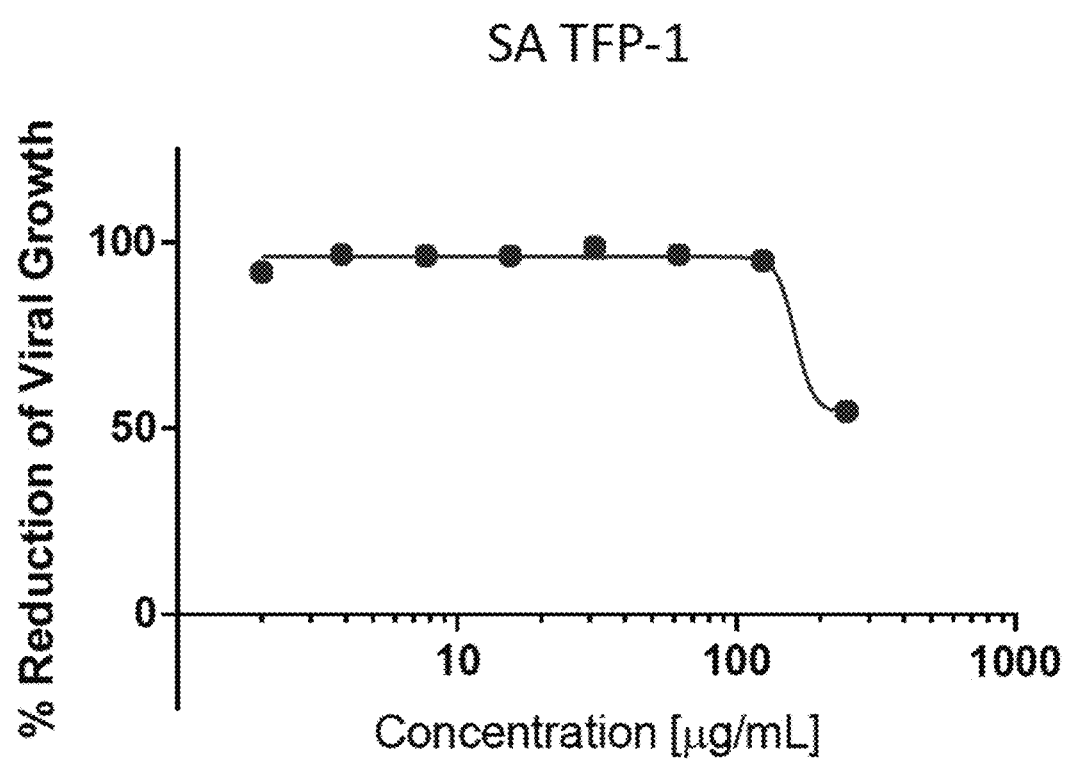
Figure 40:
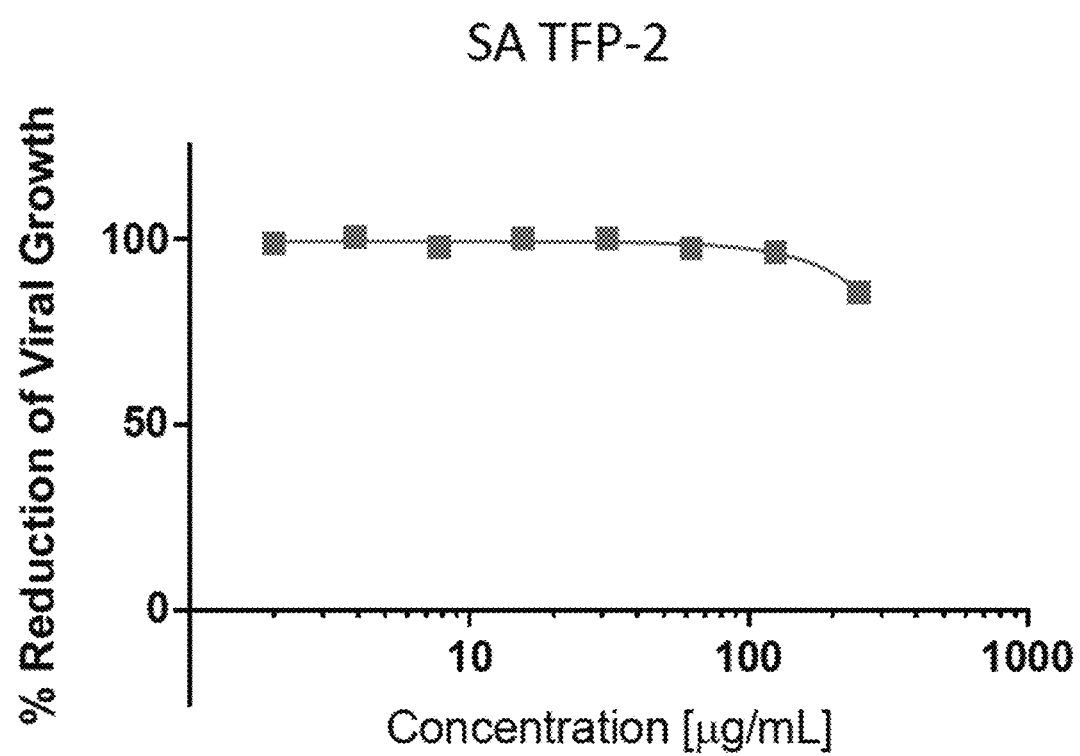
Figure 41:
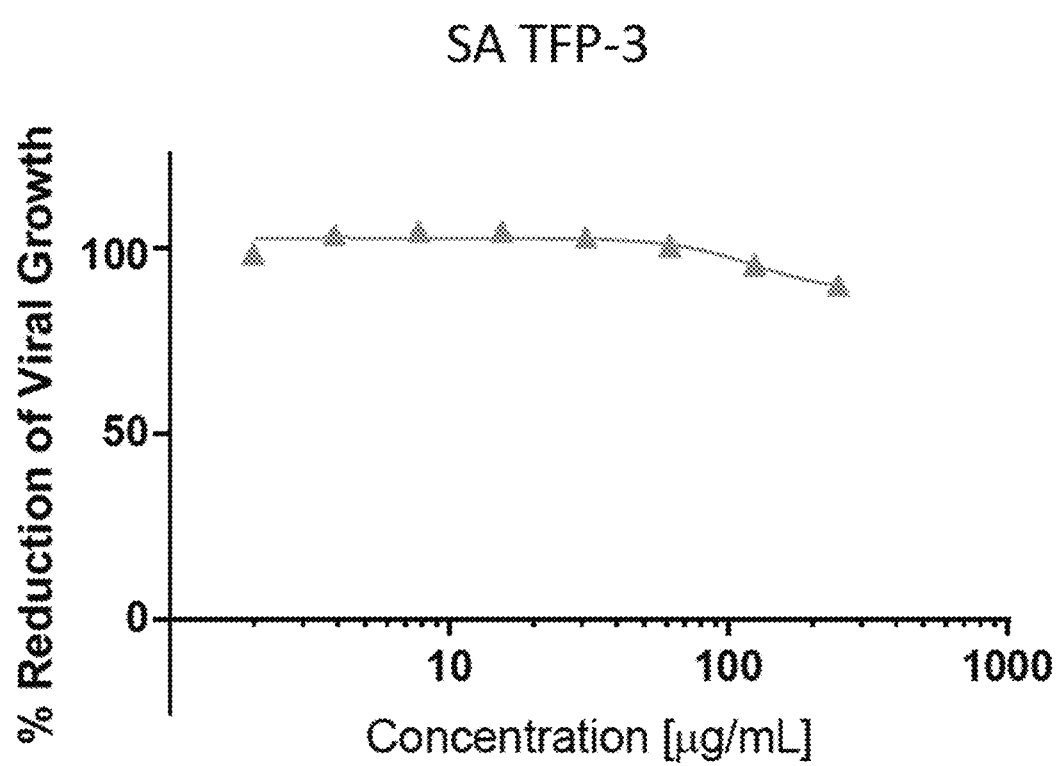
Figure 42:
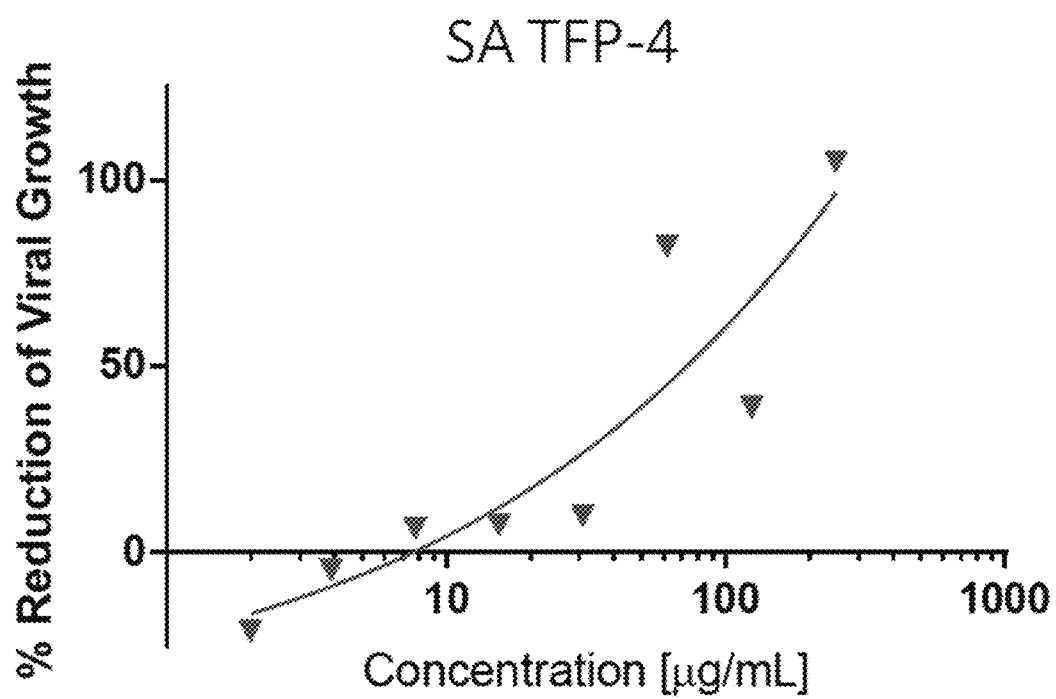
Figure 43:
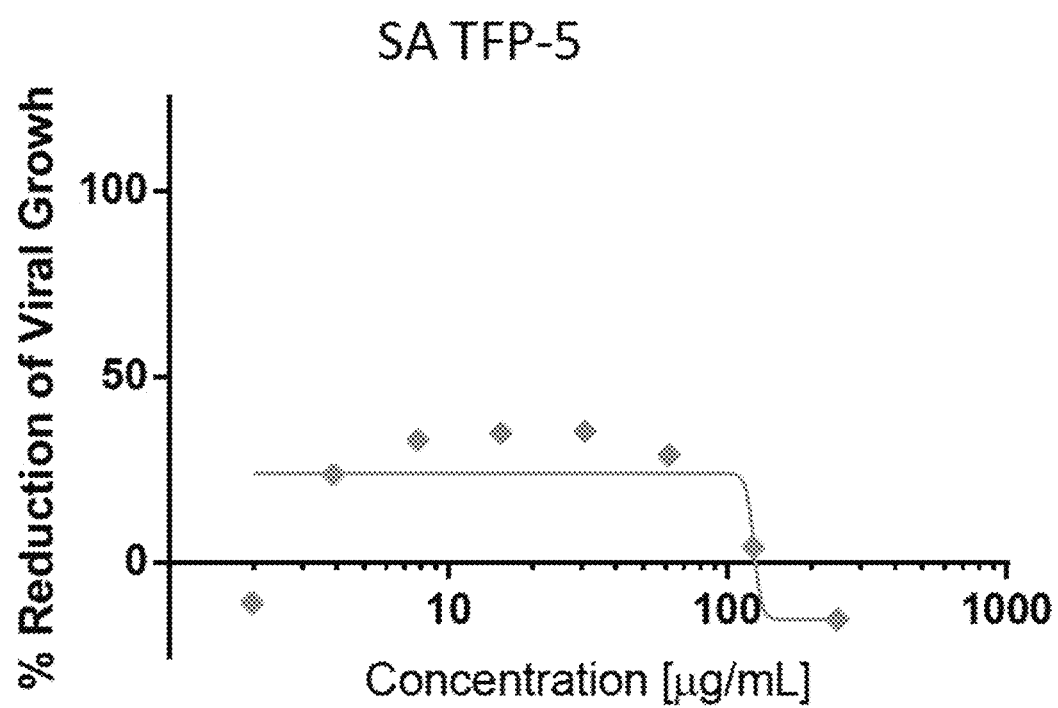
Figure 44:
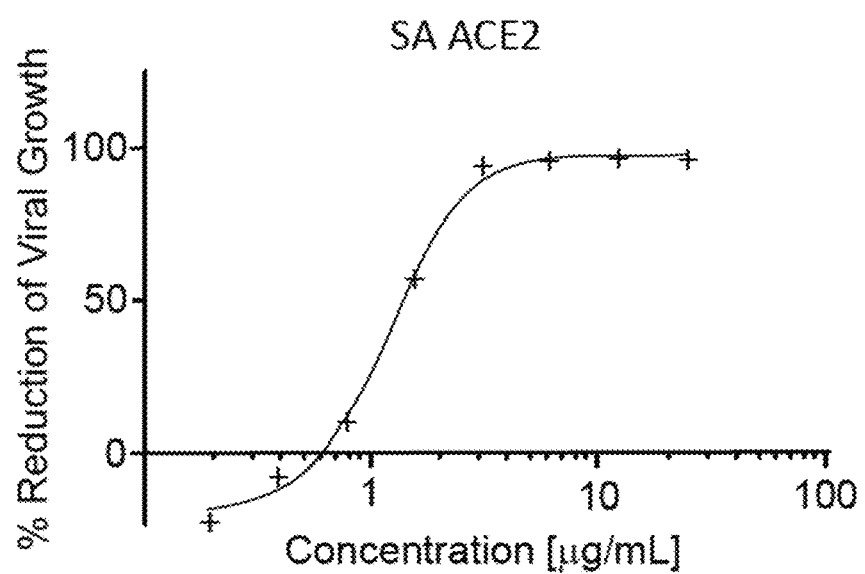
Figure 45:
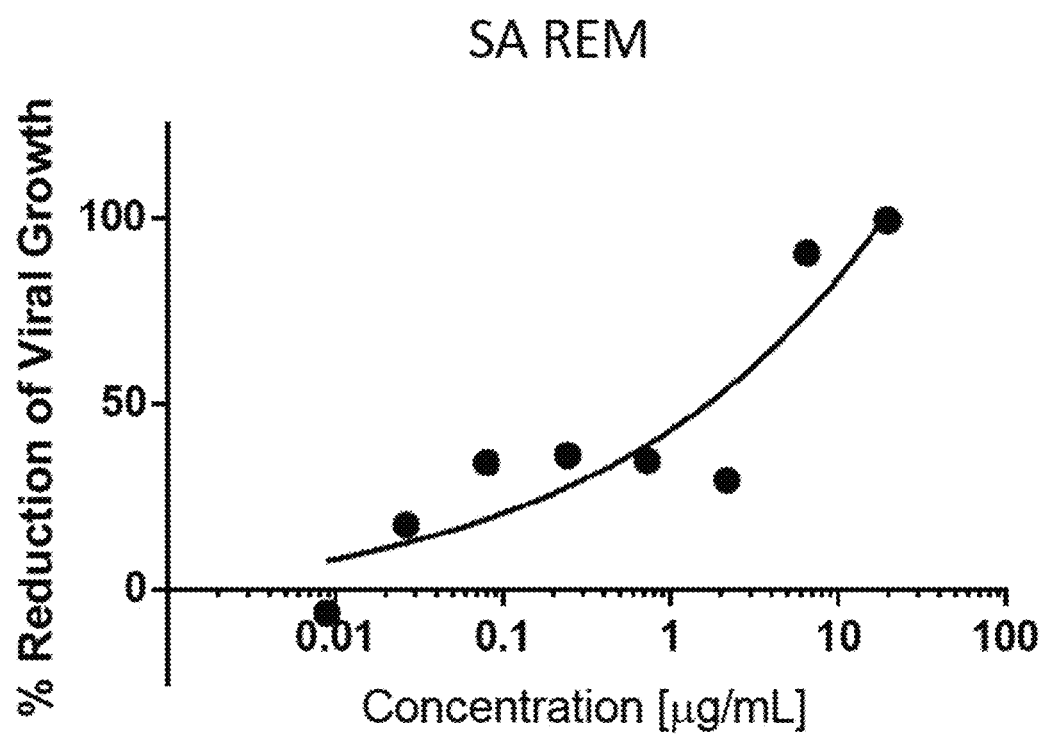
Figure 46:
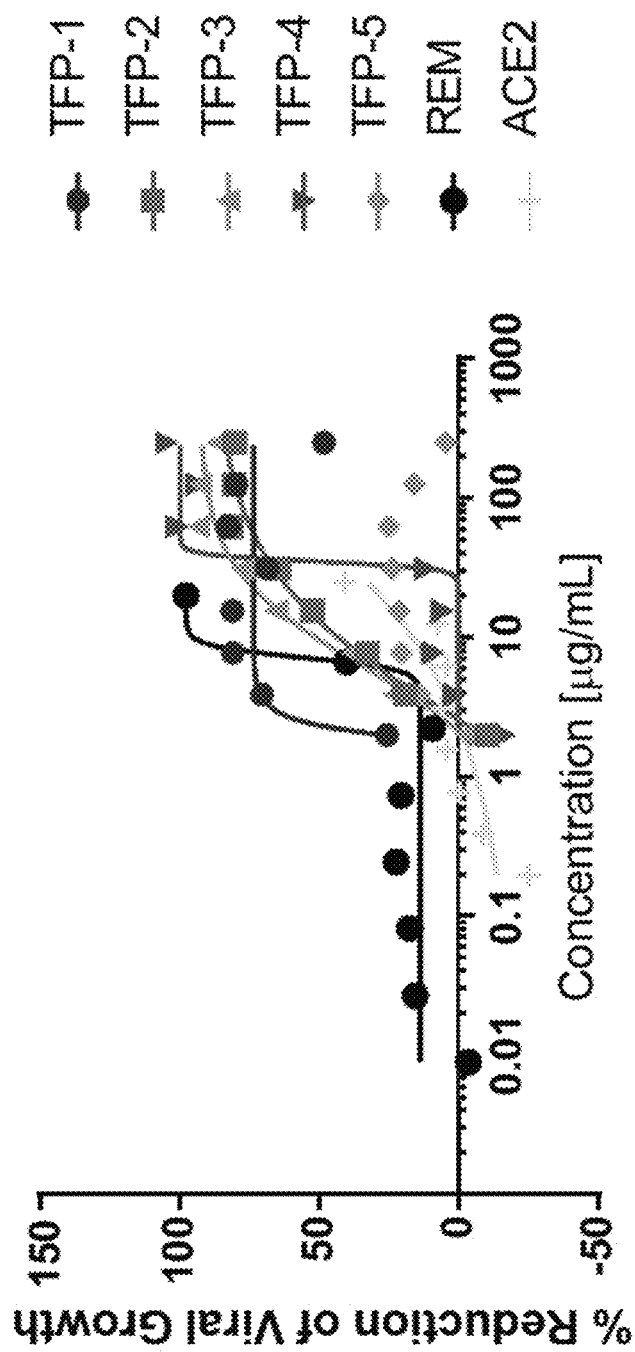
Figure 47:
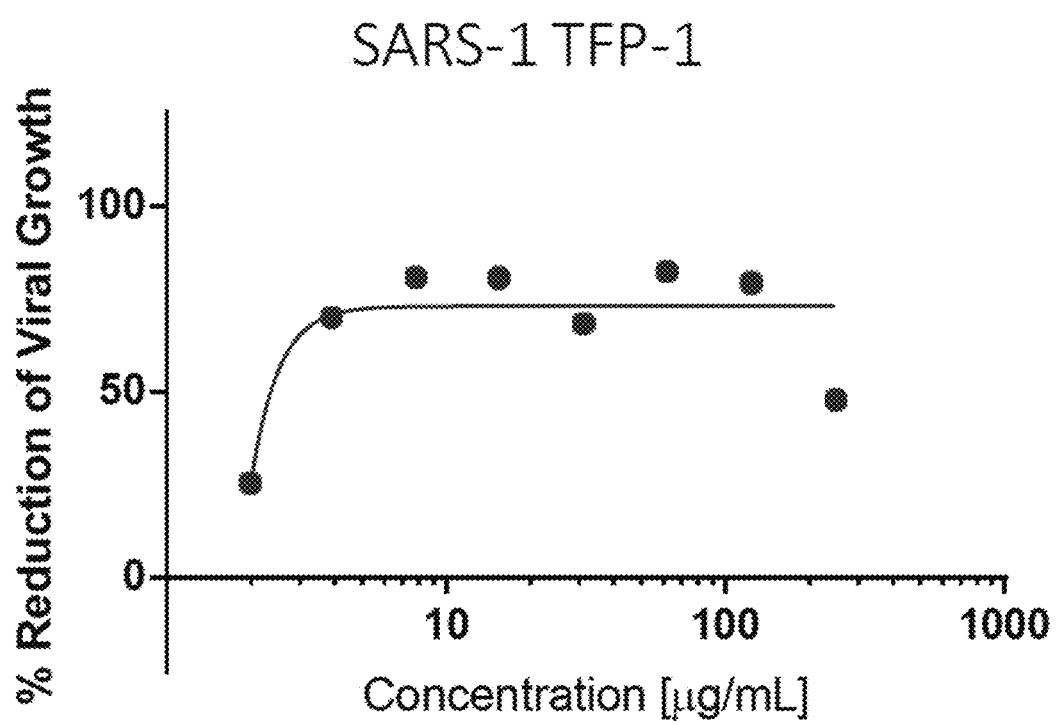
Figure 48:
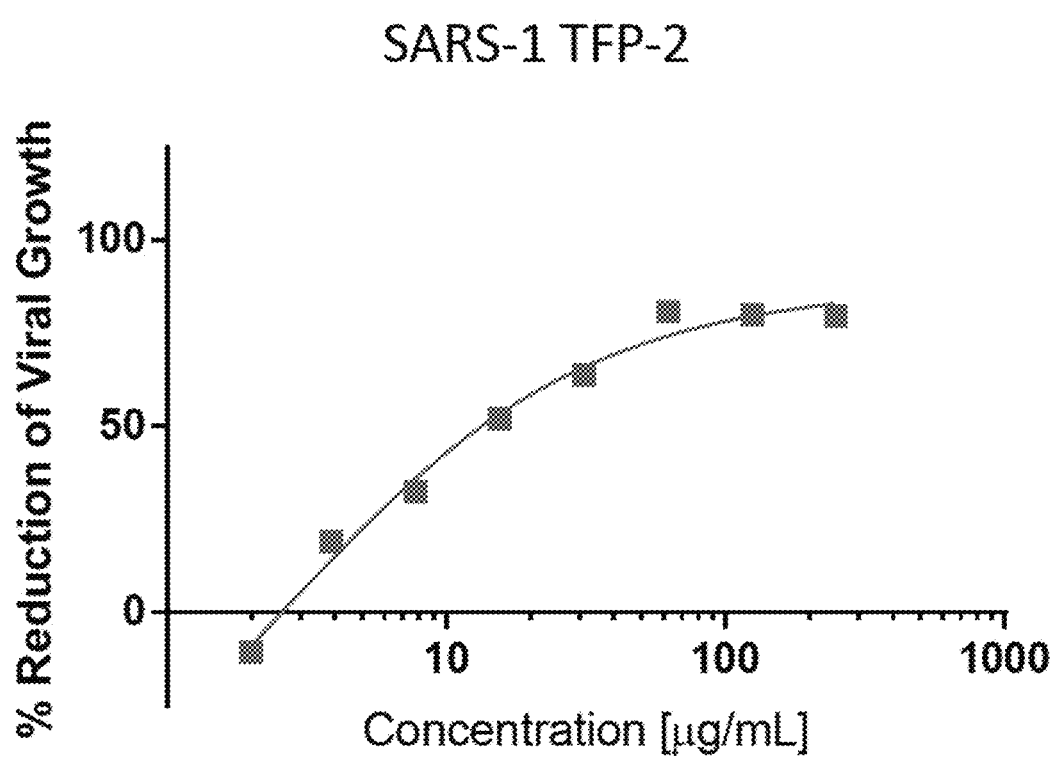
Figure 49:
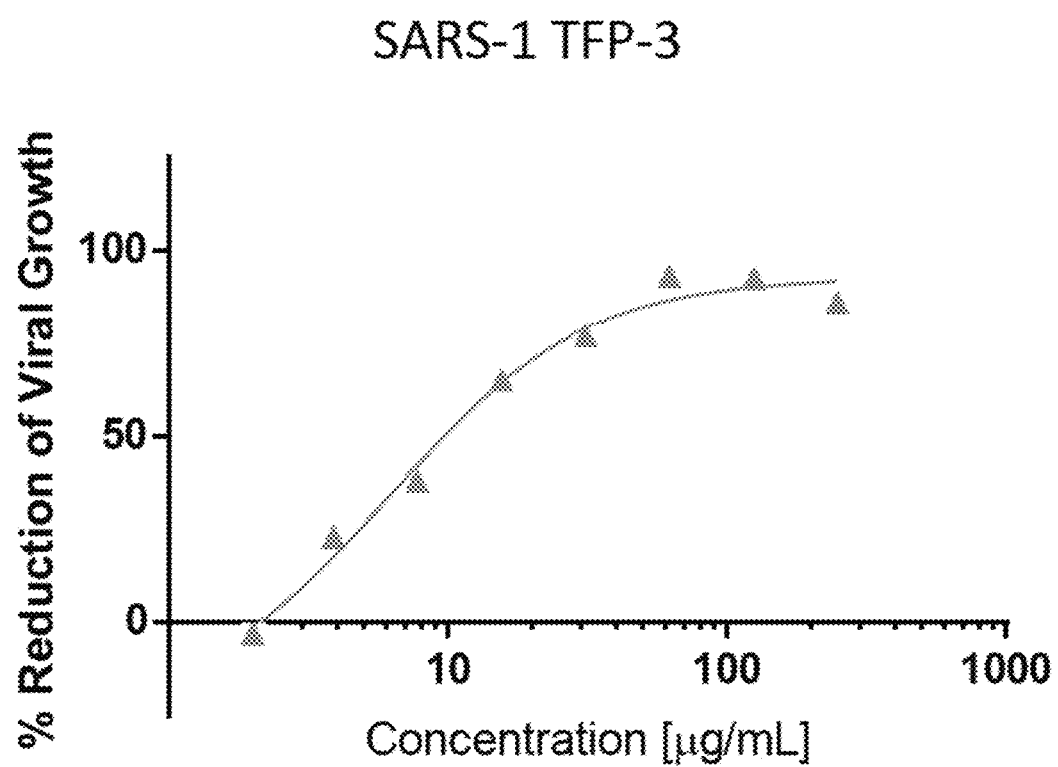
Figure 50:
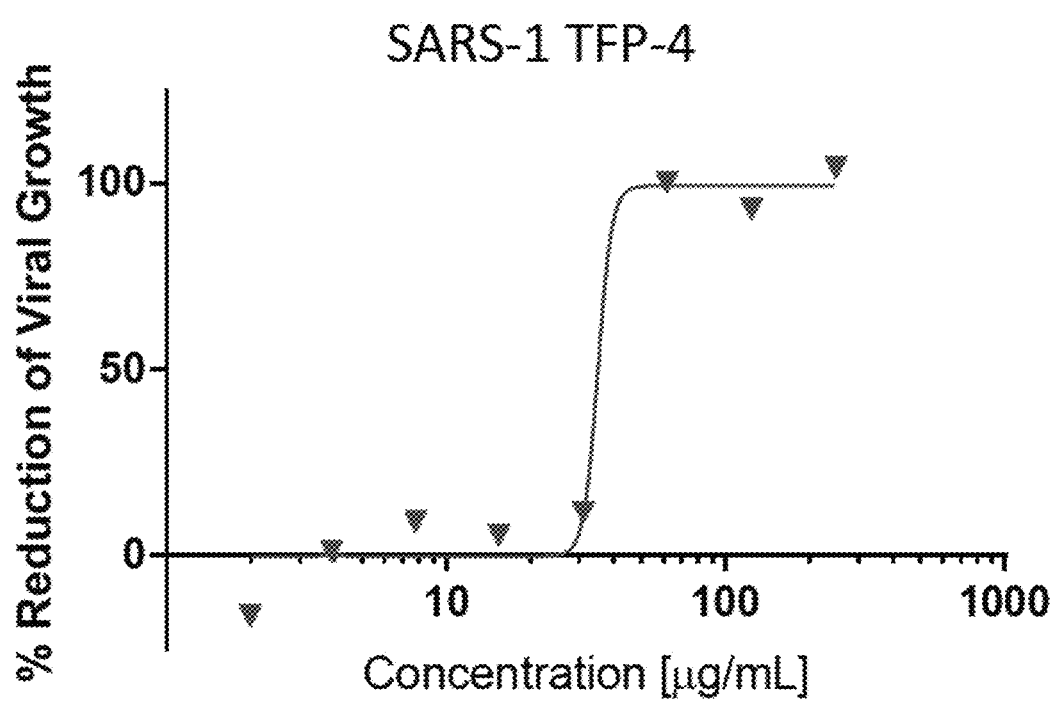
Figure 52:
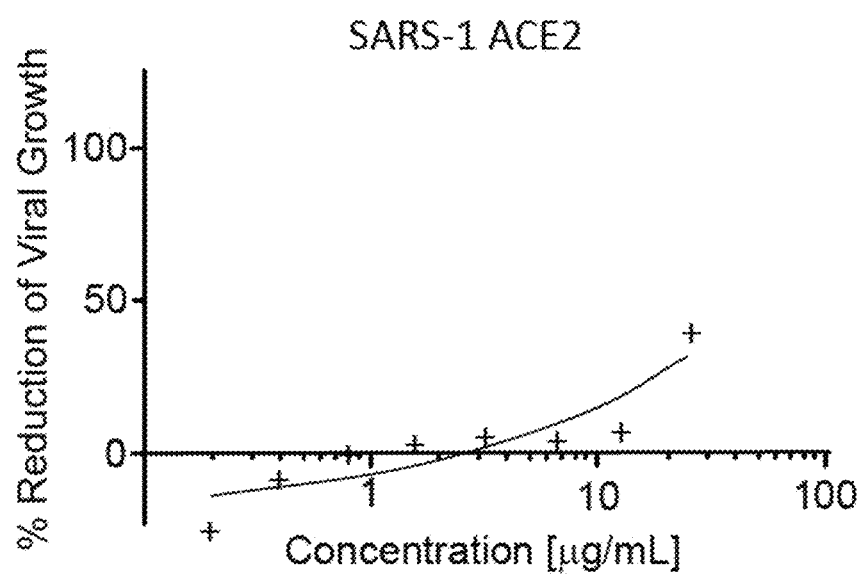

As shown in FIG. 20, MRSA growth was abrogated in test articles comprising the HPMC formulation and rhACE-2 (i.e., TFP-1 and TFP-2). Similarly, MSSA growth was decreased in cells treated with TFP-1 (but not TFP-2). See FIG. 21. These data demonstrate that the formulations comprise no anti-bacterial activity.

To measure antiviral activity, virus titer was determined. All test articles were serially diluted 2-fold, mixed with 200 TCID50 of virus, and then transferred into 3 replicate wells/dilution (2 wells/dilution for test article 6) to corresponding wells in 96-well plate which contains a monolayer of Vero E6 cells for titration. The positive control was Remdesivir. The 96-well plate was incubated in a humidified chamber at 37° C.±2° C. in 5±2% CO2. At 48 hrs±4 hrs post inoculation, wells were scored for virus replication by immunostaining with an antibody specific for the SARS-CoV-2 nucleoprotein. Data was reported as the drug concentration that results in a 50% reduction in staining intensity as compared to virus controls.

As shown in FIGS. 22-29, there was a concentration-dependent decrease in detected viral titer in the Washington variant in test articles TFP-1 and TFP-2. Further, there was a concentration-dependent decrease in detected viral titer in the United Kingdom variant (FIGS. 30-37), the South African variant (FIGS. 38-45), and SARS-CoV-1 (FIGS. 46-53) in test articles TFP-1 and TFP-2 as well. These data clearly demonstrate that the formulations comprising HPMC and rhACE-2 have antiviral activity, and that the antiviral activity is higher than Remdesivir. Finally, as shown in Table 20, for each coronavirus tested, the EC50 value for TFP-1 and TFP-2 was lower than the other test articles (TFP-3-TFP-5) demonstrating a lower half-maximal response in TFP-1 and TFP-2 compared to the other test articles.

TABLE 20

EC50 values for Test Articles for coronavirus variants

| Virus | TA | EC50 |
|---|---|---|
| WA | TFP-1 | 3.295 |
| WA | TFP-2 | 3.863 |
| WA | TFP-3 | 4.307 |
| WA | TFP-4 | 352.7 |
| WA | TFP-5 | NA |
| WA | ACE2 | 9.206 |
| WA | REM | 6 |
| UK | TFP-1 | <2 |
| UK | TFP-2 | <2 |
| UK | TFP-3 | <2 |
| UK | TFP-4 | 50 |
| UK | TFP-5 | NA |
| UK | ACE2 | 0.33 |
| UK | REM | 0.15 |
| SA | TFP-1 | <2 |
| SA | TFP-2 | <2 |
| SA | TFP-3 | <2 |
| SA | TFP-4 | 75 |
| SA | TFP-5 | NA |
| SA | ACE2 | 1.18 |
| SA | REM | 2 |
| SARS-1 | TFP-1 | 1 |
| SARS-1 | TFP-2 | 2.3 |
| SARS-1 | TFP-3 | 6.3 |
| SARS-1 | TFP-4 | 35 |
| SARS-1 | TFP-5 | NA |
| SARS-1 | ACE2 | NA |
| SARS-1 | REM | 7.2 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. Section headings, the materials, methods, and examples are illustrative only and not intended to be limiting.

SEQUENCE LISTING

```
Sequence total quantity: 2
SEQ ID NO: 1            moltype = AA  length = 805
FEATURE                 Location/Qualifiers
source                  1..805
                        mol_type = protein
                        organism = Homo sapiens
SEQUENCE: 1
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 2            moltype = AA  length = 723
FEATURE                 Location/Qualifiers
source                  1..723
                        mol_type = protein
                        organism = synthetic construct
SEQUENCE: 2
QSTIEEQAKT FLDKFNHEAE DLFYQSSLAS WNYNTNITEE NVQNMNNAGD KWSAFLKEQS  60
TLAQMYPLQE IQNLTVKLQL QALQQNGSSV LSEDKSKRLN TILNTMSTIY STGKVCNPDN  120
PQECLLLEPG LNEIMANSLD YNERLWAWES WRSEVGKQLR PLYEEYVVLK NEMARANHYE  180
DYGDYWRGDY EVNGVDGYDY SRGQLIEDVE HTFEEIKPLY EHLHAYVRAK LMNAYPSYIS  240
PIGCLPAHLL GDMWGRFWTN LYSLTVPFGQ KPNIDVTDAM VDQAWDAQRI FKEAEKFFVS  300
VGLPNMTQGF WENSMLTDPG NVQKAVCHPT AWDLGKGDFR ILMCTKVTMD DFLTAHHEMG  360
```

-continued

```
HIQYDMAYAA QPFLLRNGAN EGFHEAVGEI MSLSAATPKH LKSIGLLSPD FQEDNETEIN  420
FLLKQALTIV GTLPFTYMLE KWRWMVFKGE IPKDQWMKKW WEMKREIVGV VEPVPHDETY  480
CDPASLFHVS NDYSFIRYYT RTLYQFQFQE ALCQAAKHEG PLHKCDISNS TEAGQKLFNM  540
LRLGKSEPWT LALENVVGAK NMNVRPLLNY FEPLFTWLKD QNKNSFVGWS TDWSPYADQS  600
IKVRISLKSA LGDKAYEWND NEMYLFRSSV AYAMRQYFLK VKNQMILFGE EDVRVANLKP  660
RISFNFFVTA PKNVSDIIPR TEVEKAIRMS RSRINDAFRL NDNSLEFLGI QPTLGPPNQP  720
PVS                                                              723
```

What is claimed is:

1. A method of treating a subject infected with or at risk of being infected with a coronavirus, the method comprising administering to the subject a therapeutically effective amount of a formulation comprising:
   (a) a recombinant angiotensin converting enzyme 2 (rACE-2) protein that specifically binds to a coronavirus protein, wherein the rACE-2 protein comprises an amino acid sequence with at least 90% sequence identity to SEQ ID NO:2;
   (b) a cellulose derivative selected from hydroxypropyl cellulose (HPC), hydroxypropyl methyl cellulose (HPMC), or a combination thereof; and
   (c) an excipient selected from a glycol alcohol, a sugar alcohol, an acid, an ester, or any combination thereof, wherein the rACE-2 protein is at a concentration of about 2 percent weight/weight (w/w).

2. The method of claim 1, wherein the administering is intranasally, orally, or topically.

3. The method of claim 1, wherein the rACE-2 protein comprises the amino acid sequence of SEQ ID NO:2.

4. The method of claim 1, wherein the rACE-2 protein consists of the amino acid sequence of SEQ ID NO: 2.

5. The method of claim 1, wherein the coronavirus is an alphacoronavirus or a betacoronavirus.

6. The method of claim 5, wherein the betacoronavirus is HCoV-NL63, SARS-CoV-1, or SARS-CoV-2.

7. The method of claim 1, wherein the coronavirus is a SARS-CoV-2 coronavirus.

8. The method of claim 1, wherein the subject is a human subject.

9. A method of treating a subject infected with or at risk of being infected with a coronavirus, the method comprising administering to the subject a therapeutically effective amount of a formulation comprising:
   (a) a recombinant angiotensin converting enzyme 2 (rACE-2) protein that specifically binds to a coronavirus protein, wherein the rACE-2 protein comprises an amino acid sequence with at least 90% sequence identity to SEQ ID NO:2;
   (b) a cellulose derivative selected from hydroxypropyl cellulose (HPC), hydroxypropyl methyl cellulose (HPMC), or a combination thereof; and
   (c) a glycol alcohol at a concentration of about 1 percent w/w to about 10 percent w/w, wherein the glycol alcohol is an excipient.

10. A method of treating a subject infected with or at risk of being infected with a coronavirus, the method comprising administering to the subject a therapeutically effective amount of a formulation comprising:
    (a) a recombinant angiotensin converting enzyme 2 (rACE-2) protein that specifically binds to a coronavirus protein, wherein the rACE-2 protein comprises an amino acid sequence with at least 90% sequence identity to SEQ ID NO:2;
    (b) a cellulose derivative selected from hydroxypropyl cellulose (HPC), hydroxypropyl methyl cellulose (HPMC), or a combination thereof; and
    (c) mannitol, wherein the mannitol is an excipient.

11. The method of claim 10, wherein the mannitol is at a concentration of about 0.01 percent w/w to about 10 percent w/w.

12. A method of treating a subject infected with or at risk of being infected with a coronavirus, the method comprising administering to the subject a therapeutically effective amount of a formulation comprising:
    (a) a recombinant angiotensin converting enzyme 2 (rACE-2) protein that specifically binds to a coronavirus protein, wherein the rACE-2 protein comprises an amino acid sequence with at least 90% sequence identity to SEQ ID NO:2;
    (b) a cellulose derivative selected from hydroxypropyl cellulose (HPC), hydroxypropyl methyl cellulose (HPMC), or a combination thereof; and
    (c) sorbic acid, wherein the sorbic acid is an excipient.

13. The method of claim 12, wherein the sorbic acid is at a concentration of about 0.01 percent w/w to about 1 percent w/w.

14. A method of treating a subject infected with or at risk of being infected with a coronavirus, the method comprising administering to the subject a therapeutically effective amount of a formulation comprising:
    (a) a recombinant angiotensin converting enzyme 2 (rACE-2) protein that specifically binds to a coronavirus protein, wherein the rACE-2 protein comprises an amino acid sequence with at least 90% sequence identity to SEQ ID NO:2;
    (b) a cellulose derivative selected from hydroxypropyl cellulose (HPC), hydroxypropyl methyl cellulose (HPMC), or a combination thereof; and
    (c) polysorbate 20, wherein the polysorbate 20 is an excipient.

* * * * *